United States Patent [19]

Johnson

[11] Patent Number: 5,180,736
[45] Date of Patent: Jan. 19, 1993

[54] POLYCYCLIC AMINES USEFUL AS CEREBROVASCULAR AGENTS

[75] Inventor: Graham Johnson, Ann Arbor, Mich.

[73] Assignee: Warner-Lambert Company, Morris Plains, N.J.

[21] Appl. No.: 702,660

[22] Filed: May 17, 1991

Related U.S. Application Data

[60] Division of Ser. No. 483,482, Feb. 27, 1990, Pat. No. 5,071,853, which is a continuation-in-part of Ser. No. 327,648, Mar. 23, 1989, abandoned.

[51] Int. Cl.$^5$ .................. A61K 31/35; A61K 31/135; C07D 311/80; C07C 211/42
[52] U.S. Cl. ..................... 514/454; 514/183; 514/210; 514/212; 514/213; 514/215; 514/217; 514/280; 514/282; 514/284; 514/285; 514/287; 514/290; 514/291; 514/301; 514/302; 514/321; 514/323; 514/324; 514/325; 514/410; 514/411; 514/422; 514/428; 514/429; 514/431; 514/432; 514/437; 514/443; 514/450; 514/453; 514/455; 514/468; 514/510; 514/561; 514/562; 514/567; 514/569; 514/602; 514/603; 514/648; 514/654; 514/655; 514/656; 540/576; 540/586; 540/596; 540/597; 540/602; 540/611; 546/42; 546/47; 546/48; 546/61; 546/62; 546/64; 546/65; 546/77; 546/78; 546/79; 546/80; 546/82; 546/83; 546/89; 546/90; 546/92; 546/93; 546/101; 546/110; 546/111; 546/195; 546/196; 546/197; 546/198; 546/200; 546/203; 546/204; 548/416; 548/418; 548/421; 548/426; 548/427; 548/429; 548/430; 548/431; 548/432; 548/450; 548/451; 548/529; 548/950; 548/954; 548/962; 548/967; 548/968; 549/12; 549/23; 549/24; 549/25; 549/26; 549/27; 549/41; 549/42; 549/43; 549/44; 549/45; 549/47; 549/48; 549/348; 549/349; 549/358; 549/359; 549/360; 549/391; 549/456; 549/457; 549/458; 549/459; 549/460; 549/461; 560/10; 560/28; 560/43; 560/51; 560/56; 560/105; 560/354; 562/427; 562/457; 564/84; 564/85; 564/86; 564/88; 564/89; 564/315; 564/374; 564/387; 564/426; 564/427

[58] Field of Search ............... 549/390, 391; 514/454, 514/455

[56] References Cited

U.S. PATENT DOCUMENTS

| 3,111,527 | 11/1963 | Godefroi | 260/330.5 |
| 3,159,677 | 12/1964 | Godefroi | 260/576 |
| 3,206,480 | 9/1965 | Godefroi | 260/346.2 |
| 3,317,527 | 5/1967 | Skaletsky | 260/247.7 |
| 3,886,184 | 5/1979 | Matsumoto et al. | 549/390 |
| 4,152,450 | 5/1979 | Day et al. | 549/390 |
| 4,463,001 | 7/1984 | Melloni et al. | 549/390 |
| 4,496,557 | 1/1985 | Malen et al. | 549/390 |
| 4,668,690 | 5/1987 | Shutske | 514/320 |
| 4,876,276 | 10/1989 | Mechoulam et al. | 549/390 |

FOREIGN PATENT DOCUMENTS 893920 4/1962 United Kingdom .

OTHER PUBLICATIONS

Schwarcz et al., *The Lancet*, (1985) 140.
Meldrum et al., Neurotoxins and their pharmacological implications, (1987), Raven Press.
D. W. Choi, *Neuron* (1988) 1:623.
McDonald et al., *Eur. J. Pharmacol.*, (1987) 140:359.
Gill et al., *J. Neurosci.*, (1987) 7:3343.
Rothman et al., *Neuroscience* (1987) 21:673.
Goldberg et al., *Neurosci. Lett.* (1987) 80:11.
Copeland et al., *Soc. Neurosci. Abs.*, (1988) 14 (part 1):420.
Kemp et al., *TIPS* (1987) 8:414.
Gill et al., *Neuroscience* (1988) 25:847.
Park et al., *Am. Neurol.* (1988) 24:543.
Steinberg et al., *Stroke* (1988) 19:1112.
Church et al., *Anesthesiology* (1988) 69:702.
Godefroi et al., *J. Org. Chem.* (1963) 28:1112.
Ackland et al., *J. Chem. Soc. Perkin Trans. I* (1987) 2695.
Derwent Abstract, Japanese 506/68.
Kametani et al., *J. Org. Chem.* (1987) 52:5233.
Yardley et al., *Can. J. Chem.* (1985) 63:1013.

*Primary Examiner*—Carolyn Elmore
*Assistant Examiner*—P. O'Sullivan
*Attorney, Agent, or Firm*—Elizabeth M. Anderson

[57] ABSTRACT

A novel series of polycyclic amines, derivatives, methods of making the compounds, novel intermediates, compositions containing them, and methods for using them in the treatment and prevention of cerebrovascular disorders are disclosed.

8 Claims, No Drawings

POLYCYCLIC AMINES USEFUL AS CEREBROVASCULAR AGENTS

This application is a divisional of U.S. Ser. No. 07/483,482 filed Feb. 27, 1990, now U.S. Pat. No. 5,071,853, which is a continuation-in-part of U.S. Ser. No. 07/327,648 filed Mar. 23, 1989, now abandoned.

BACKGROUND OF THE INVENTION

Excessive excitation by neurotransmitters can cause the degeneration and death of neurons. It is believed that this excitotoxic action is mediated by the excitatory amino acids, glutamate and aspartate, acting at the N-methyl-D-aspartate (NMDA) receptor. This action is responsible for neuronal loss in cerebrovascular disorders such as: cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma.

While there are no specific therapies for these neurodegenerative disorders, compounds acting specifically to antagonize, competitively or noncompetitively, excitatory neurotransmission at NMDA receptors offer a novel therapeutic approach to these disorders: R. Schwarcz and B. Meldrum, *The Lancet* 140 (1985); B. Meldrum in "Neurotoxins and Their Pharmacological Implications" edited by P. Jenner, Raven Press, New York, 1987); D. W. Choi, Neuron 1:623 (1988). Recent literature reports have confirmed the protective action of examples of noncompetitive NMDA antagonists in pharmacological models of neuro-degenerative disorders: J. W. McDonald, F. S. Silverstein, and M. V. Johnston, *Eur. J. Pharmacol.* 140:359 (1987); R. Gill, A. C. Foster, and G. N. Woodruff, *J. Neurosci.* 7:3343 (1987); S. M. Rothman, J. H. Thurston, R. E. Hauhart, G. D. Clark, and J. S. Soloman, *Neurosci.* 21:673 (1987); M. P. Goldbert, P-C. Pham and D. W. Choi, *Neurosci. Lett.* 80:11 (1987); L. F. Copeland, P. A. Boxer, and F. W. Marcoux, *Soc. Neurosci. Abstr.* 14 (part 1):420 (1988); J. A. Kemp, A. C. Foster, R. Gill, and G. N. Woodruff, *TIPS* 8:414 (1987); R. Gill, A. C. Foster, and G. N. Woodruff, *J. Neurosci.* 25:847 (1988); C. K. Park, D. G. Nehls, D. 1. Graham, G. M. Teasdale, and J. M. McCulloch, *Ann. Neuro.* 24:543 (1988); G. K. Steinberg, C. P. George, R. DeLaPaz, D. K. Shibata, and T. Gross, *Stroke* 19:1112 (1988); J. F. Church, S. Zeman, and D. Lodge, *Anesthesiology* 69:702 (1988).

U.S. Pat. Nos. 3,159,677, 3,206,480, and 3,111,527, and British Patent 893,920 disclose certain fluorenamines, dibenzofuranamines, dibenzothiophenamines, and processes for preparing them. The compounds are disclosed as having central nervous system depressant activity. The further preparation of these compounds is described by E. Godefroi and L. Simanyi in *J. Org. Chem.* 28:1112 (1963). U.S. Pat. No. 3,317,527 and Netherlands Patent 6,415,270 disclose certain amino substituted 5- to 7[a]-benzofuranols as central nervous system stimulants. United States Patent 4,668,690 discloses hexahydro-4a-aminoalkyldibenzofurans useful as analgesics, anticonvulsants, and antidepressants. The preparation of certain aminoethyl tetrahydrodibenzofuranamines is described by D. J. Ackland and J. T. Pinhey in *J. Chem. Soc. Perkin Transl.* 2695 1987). Japanese Patent 50668 discloses certain aminoethylphenanthrenes as antihypotensives. The preparation of further aminoethyl tetrahydrophenanthreneamines are described by T. Kamatani, M. Nishimura, K. Higurashi, M. Tsbuki, and Ionda in *J. Org. Chem.* 52:5233 (1987). The preparation of certain aminomethylhexahydrophenanthrenes and a trans ring-fused octahydrophenanthreneamine is described by J. P. Yardley and R. W. Rees in *Can. J. Chem.* 63:1013 (1985). None of these publications teaches to the preparation and utility of the compounds of the present invention.

The compounds of the present invention are useful in the treatment of neurodegenerative disorders including cerebrovascular disorders. Such disorders include but are not limited to cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma. Other treatments are for schizophrenia, epilepsy, spasticity, neurodegenerative disorders such as Alzheimer's disease or Huntington's disease, Olivo-pontocerebellar atrophy, spinal cord injury, and poisoning by exogenous NMDA poisons (e.g., some forms of lathyrism). Further uses are as analgesics and anesthetics, particularly for use in surgical procedures where a finite risk of cerebrovascular damage exists.

SUMMARY OF THE INVENTION

The present invention provides compounds of formula

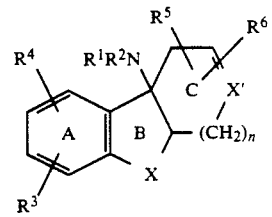

or a pharmaceutically acceptable salt thereof wherein $R^1$, $R^2$, $R^3$, $R^4$, $R^5$, $R^6$, n, X, and X' are as defined below.

Compounds of formula I above are those wherein the point of fusion of rings B and C are cis or trans. Unless otherwise stated the cis form is preferred.

Preferred compounds of the instant invention are those of formula I wherein the A ring is benzene and $R^1$ and $R^2$ are each independently hydrogen, loweralkyl or loweralkenyl, $R^3$ and $R^4$ are each independently hydrogen, halogen, hydroxy, hydroxymethyl, loweralkoxy, amino, monoloweralkylamino, 1-hydroxyethyl, $R^5$ and $R^6$ are each independently hydrogen, loweralkyl, hydroxy, hydroxymethyl, amino, aminomethyl, 1-aminoethyl, mono- and diloweralkylaminomethyl, 1-mono- and diloweralkylaminoethyl, loweralkoxy, loweralkoxymethyl, 1-loweralkoxyethyl, or when taken together $R^5$ and $R^6$ form a carbocyclic ring, n is 1, X' is —CH$_2$ or —CH—, X is —CR$^7$R$^8$—, —CHR$^7$CHR$^8$—, —CHR$^7$CR$^8$CH$_2$—, —SCHR$^7$—, —CR$^7$=CR$^8$CH$_2$—, —CHR$^7$S—, —CHR$^7$O—, —OCHR$^7$—, wherein R$^7$ and R$^8$ are each independently hydrogen, with the above proviso, or loweralkyl or aminoloweralkyl, hydroxyloweralkyl, monoloweralkylaminoloweralkyl, when taken together $R^7$ and $R^8$ may form a carbocyclic ring, the—in ring C is an optional double bond.

More preferred compounds of the instant invention are those of formula I above wherein $R^1$ and $R^2$ are each independently hydrogen, loweralkyl, or loweralkenyl, $R^3$ and $R^4$ are each independently hydrogen, halogen, hydroxy or loweralkoxy, $R^5$ and $R^6$ are each independently hydrogen, loweralkyl, or loweralkoxy, aminomethyl, mono- and diloweralkylaminomethyl, hydroxymethyl, loweralkoxymethyl, X' is —CH$_2$—, n is 1, X is —CR$^7$R$^8$—, —CHR$^7$CHR$^8$—, —CHR$^7$CHR$^8$CH$_2$—, —SCHR$^7$—, —OCHR$^7$—, wherein $R^7$ and $R^8$ are each independently hydrogen with the above proviso.

Most preferred compounds of the instant invention are those of formula I above wherein $R^1$ and $R^2$ are each independently hydrogen loweralkyl, or loweralkenyl, $R^3$ and $R^4$ are independently hydrogen, hydroxy, or methoxy, $R^5$ and $R^6$ are independently hydrogen, hydroxymethyl, or aminomethyl, X' is —CH$_2$, n is 1, X is —CR$^7$ R$^8$ —, —CHR$^7$CR$^8$—, —CHR$^7$CR$^8$CH$_2$—, or —SCHR$^7$—, —OCHR$^7$— wherein $R^7$ and $R^8$ are each hydrogen with the above proviso.

Most especially preferred compounds of the instant invention are:

(+)-1,3,4,9,10,10a-hexahydro-N-methyl-4a(2H)-phenanthrenamine, (−)-1,3,4,9,10,10a-hexahydro-N-methyl-4a(2H)-phenanthrenamine, (±)-1,3,4,9,10,10a-hexahydro-N-methyl-4a(2H)-phenanthrenamine, (+)-1,3,4,9,10,10a-hexahydro-4a(2H)-phenanthrenamine, (−)-1,3,4,9,10,10a-hexahydro-4a(2H)-phenanthrenamine, (±)-1,3,4,9,10,10a-hexahydro-4a(2H)-phenanthrenamine, 1,3,4,9,10,10a-hexahydro-6-methoxy-4a(2H)-phenanthrenamine, 1,3,4,9,10,10a-hexahydro-6-methoxy-N-methyl-4a(2H)-phenanthrenamine, 4b,5,6,7,8,8a,9,10-octahydro-4b-amino-3-phenanthrenol, 4b,5,6,7,8,8a,9,10-octahydro-4b-(methylamino)-3-phenanthrenol, 1,3,4,10a-tetrahydro-N-2-propenyl-4a(2H)-phenanthrenamine, 1,2,3,4,4a,9,10,10a-octahydro-4a-(methylamino)-2-phenanthrenemethanol, 1,2,3,4,4a,9,10,10a-octahydro-4a-(methylamino)-2-phenanthrenemethanamine, 1,2,3,4,4a,9,10,10a-octahydro-N-methyl-4a-(methylamino)-2-phenanthrenemethanamine, 1,2,3,4,4a,9,10,10a-octahydro-6-methoxy-4a-(methylamino)-2-phenanthrenemethanol, 1,2,3,4,4a,9,10,10a-octahydro-6-methoxy-4a-(methylamino)-2-phenanthrenemethanamine, 1,2,3,4,4a,9,10,10a-octahydro-6-methoxy-N-methyl-4a-(methylamino)-2-phenanthrenemethanamine, 1,2,3,4,4a,9,10,10a-octahydro-6-hydroxy-4a-(methylamino)-2-phenanthrenemethanol, 1,2,3,4,4a,9,10,10a-octahydro-6-hydroxy-4a-methylamino)-2-phenanthrenemethanamine, 1,2,3,4,4a,9,10,10a-octahydro-6-hydroxy-N-methyl-4a-(methylamino)-2-phenanthrenemethanamine, 1,3,4,10a-tetrahydro-4a(2H)-phenanthrenamine, 1,3,4,10a-tetrahydro-N-methyl-4a(2H)-phenanthrenamine, 5,6,6a,7,8,9,10,11-octahydro-N-methyl-11aHcyclohepta[a]naphthalen-11a-amine, 6,6a,7,8,9,10-hexahydro-10aH-dibenzo[b,d]pyran-10a-amine, 6,6a,7,8,9,10-hexahydro-N-methyl-10aH-dibenzo[b,d]pyran-10a-amine, 6,6a,7,10-tetrahydro-N-methyl-10aH-dibenzo[b,d]pyran-10a-amine, 1,2,3,4,9,9a-hexahydro-N,4-dimethyl-4aH-fluoren-4a-amine, 2,3,4,4a,9,9a-hexahydro-4a-(methylamino)-1H-fluorene-2-methanamine, 2,3,4,4a,9,9a-hexahydro-N-methyl-4a-(methyl-amino)-1H-fluorene-2-methanamine, 2,3,4,4a,9,9a-hexahydro-N,N-dimethyl-4a-(methylamino)-1H-fluorene-2-methanamine, 2,3,4,4a,9,9a-hexahydro-4a-(methylamino)-1H-fluorene-2-methanol, 2,3,4,4a,9,9a-hexahydro-4a-amino-1H-fluorene-2-methanol, 2,3,4,4a,9,9a-hexahydro-4a-amino-1H-fluorene-2-methanamine, 2,3,4,4a,9,9a-hexahydro-6-methoxy-4a-(methylamino)-1H-fluorene-2-methanol, 2,3,4,4a,9,9a-hexahydro-6-methoxy-4a-(methylamino)-1H-fluorene-2-methanamine, 2,3,4,4a,9,9a-hexahydro-6-methoxy-N-methyl-4a-(methylamino)-1H-fluorene-2-methanamine, 2,3,4,4a,9,9a-hexahydro-6-hydroxy-4a-(methylamino)-1H-fluorene-2-methanol, 2,3,4,4a,9,9a-hexahydro-6-hydroxy-4a-(methylamino)-1H-fluorene-2-methanamine, 2,3,4,4a,9,9a-hexahydro-6-hydroxy-N-methyl-4a-(methylamino)-1H-fluorene-2-methanamine, 1,2,3,4,9,9a-hexahydro-N-methyl-4aH-indeno[2,1-c]pyridin-4a-amine, 1,2,3,4,9,9a-hexahydro-N,2-dimethyl-4aH-indeno[2,1-c]pyridin-4a-amine, 6,6a,7,8,9,10-hexahydro--10aH-dibenzo[b,d]thiopyran-10a-amine, 6,6a,7,8,9,10-hexahydro-N-methyl-10aH-dibenzo[b,d]thiopyran-10a-amine, 6,6a,7,10-tetrahydro-10aH-dibenzo[b,d]thiopyran-10a-amine, and 6,6a,7,10-tetrahydro-N-methyl-10aH-dibenzo[b,d]-thiopyran-10a-amine.

Other preferred compounds of the instant invention are those of formula I above wherein the A ring is thiophene as in formula IA

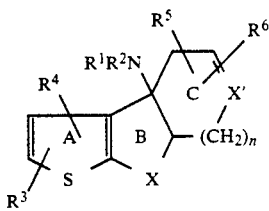

Preferred compounds of the instant invention are those wherein $R^1$ and $R^2$ are each independently hydrogen, loweralkyl or loweralkenyl, $R^3$ and $R^4$ are each independently hydrogen, halogen, hydroxy, hydroxymethyl, loweralkoxy, amino, monoloweralkylamino, 1-hydroxyethyl, $R^5$ and $R^6$ are each independently hydrogen, loweralkyl, hydroxy, hydroxymethyl, amino, aminomethyl, 1-aminoethyl, mono- and diloweralkylaminomethyl, 1-mono- and diloweralkylaminoethyl, loweralkoxy, loweralkoxymethyl, 1-loweralkoxyethyl, or when taken together $R^5$ and $R^6$ form a carbocyclic ring, n is 1, X' is —CH$_2$— or —CH—, X is —CR$^7$R$^8$—, —CHR$^7$CHR$^8$—, —CHR$^7$CR$^8$CH$_2$—, —SCHR$^7$—, —CR$^7$=CR$^8$CH$_2$—, —CHR$^7$S—, —CHR$^7$O—, —OCHR$^7$—, wherein $R^7$ and $R^8$ are each independently hydrogen, with the above proviso, or loweralkyl or aminoloweralkyl, hydroxyloweralkyl, monoloweralkylaminoloweralkyl, when taken together $R^7$ and $R^8$ may form a carbocyclic ring, the—in ring C is an optional double bond.

More preferred compounds of the instant invention are those wherein $R^1$ and $R^2$ are each independently hydrogen, lower alkyl, or lower alkenyl, $R^3$ and $R^4$ are each independently hydrogen, halogen, hydroxy or lower alkoxy, $R^5$ and $R^6$ are each independently hydrogen, loweralkyl or loweralkoxy, aminomethyl, mono- and diloweralkylaminomethyl, hydroxymethyl, loweralkoxymethyl, X' is —CH$_2$—, n is 1, X is —CR$^7$ R$^8$—, —CHR$^7$ CHR$^8$—, —CHR$^7$CHR$^8$CH$_2$—, —SCHR$^7$—, —OCHR$^7$—, wherein $R^7$ and $R^8$ are each independently hydrogen with the above proviso.

Still more preferred compounds of the instant invention are those wherein $R^1$ and $R^2$ are each independently hydrogen loweralkyl, or loweralkenyl, $R^3$ and $R^4$ are independently hydrogen, hydroxy, or methoxy, $R^5$ and $R^6$ are independently hydrogen, hydroxymethyl, or aminomethyl, X' is —CH$_2$, n is 1, X is —CR$^7$R$^8$—, —CHR$^7$CR$^8$—, —CHR$^7$CR$^8$CH$_2$—, or —SCHR$^7$—, —OCHR$^7$— wherein $R^7$ and $R^8$ are each hydrogen with the above proviso.

Most especially preferred compounds of the instant invention are selected from:

5,5a,6,7,8,9-hexahydro-9a(4H)-naphtho[2,1-b]-thiophenamine, 5,5a,6,7,8,9-hexahydro-N-methyl-9a(4H)-naphtho[2,1-b]thiophenamine, and 5,5a,6,9-tetrahydro-N-methyl-9a(4H)-naphtho[2,1-b]thiophenamine.

The present invention also covers a pharmaceutical composition comprising a therapeutically effective amount of a compound of formula I above together with a pharmaceutically acceptable carrier.

The instant invention further covers a method for treating cerebrovascular disorders which comprises administering to a patient a pharmaceutical composition as described above.

The instant invention further covers the use of the compounds of formula I above as anesthetics especially in surgical operations where risk of cerebrovascular damage exists.

The instant invention further covers processes for preparing compounds of formula I above and novel intermediates useful in the production thereof.

DETAILED DESCRIPTION

The present invention provides compounds of formula

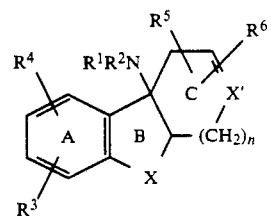

or a pharmaceutically acceptable salt thereof wherein:

$R^1$ and $R^2$ are each independently hydrogen, loweralkyl, loweralkenyl, arylloweralkyl, or a pharmaceutically acceptable labile group, or when taken together $R^1$ and $R^2$ form a heterocyclic ring;

$R^3$ and $R^4$ are each independently hydrogen, loweralkyl, hydroxy, loweralkoxy, loweralkylthio, halogen, trifluoromethyl, amino, monoloweralkylamino, diloweralkylamino; aminomethyl, hydroxymethyl, methoxymethyl, 1-hydroxyethyl, 1-methoxyethyl, hydroxyphenylmethyl, methoxyphenylmethyl, 1-aminoethyl, aminophenylmethyl, 1-loweralkylaminoethyl, or lowerakylaminophenylmethyl, Ring A is also thiophene;

$R^5$ and $R^6$ are each independently hydrogen, loweralkyl, loweralkenyl, hydroxy, loweralkoxy, loweralkylthio, aldehyde, loweralkylcarbonyl, hydroxymethyl, loweralkoxymethyl, 1- or 2-hydroxyethyl, 1- or 2-loweralkoxyethyl, amino, monoloweralkylamino, diloweralkylamino, aminomethyl, loweralkylaminomethyl, di-loweralkylaminomethyl, 1- or 2-aminoethyl, 1- or 2-loweralkylaminoethyl, 1- or 2-diloweralkylaminoethyl, or when taken together $R^5$ and $R^5$ form a carbocyclic or a heterocyclic ring; the—in ring C is an optional double bond, X' is —CH$_2$—, —CH—, O, NR, S, or SO wherein R is hydrogen, loweralkyl, alkenyl, or arylalkyl and n is 0, 1, or 2

X is —CR$^7$R$^8$—, —C$^7$R$^8$CH$_2$—, —CH$_2$CR$^7$R$^8$—, —CHR$^7$CHR$^8$—, —CR$^7$=CR$^8$—, —CR$^7$R$^8$CH$_2$CH$_2$—, —CH$_2$CH$_2$CR$^7$R$^8$—CH$_2$CR$^7$R$^8$CH$_2$—, —CHR$^7$CHR$^8$CH$_2$—,

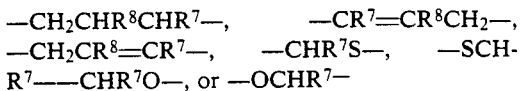

wherein $R^7$ and $R^8$ are each independently
hydrogen, loweralkyl, hydroxy, methoxy, methoxyloweralkyl, hydroxyloweralkyl, aminoloweralkyl, mono- and diloweralkylaminoloweralkyl, fluorosubstituted loweralkyl, or when taken together $R^7$ and $R^8$ form a carbocyclic ring, with the proviso that when $R^1$ and $R^2$ are hydrogen or alkyl, $R^3$ and $R^4$ are hydrogen, $R^5$ and $R^6$ are hydrogen or methyl and are at position 2 or 3 and n is 1, X cannot be —CH$_2$—, with the further proviso that for substituents α to ring A only one of $R^7$ and $R^8$ is alkyl, and with the further proviso that when $R^7$ and $R^8$ are on the same carbon atom only one of $R^7$ or $R^8$ can be a heteroatom.

Novel intermediates useful in the preparation of compounds of formula 1 are those of formulae II-VII below.

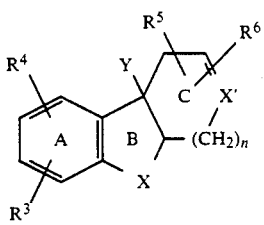

wherein Y is —NCO,
—COOR$^9$ wherein R$^9$ is hydrogen, alkyl or arylalkyl,
—NHCOR$^{10}$ wherein R$^{10}$ is hydrogen, alkyl or the amide is a physiologically labile group,
—NHCOOR$^{11}$ wherein R$^{11}$ is substituted or unsubstituted alkyl, cycloalkyl, arylalkyl, or a physiologically labile group,
—NHSO$_2$R$^{13}$ wherein R$^{13}$ is substituted or unsubstituted alkyl or aryl, and the other terms are as defined above. Other novel intermediates are those of formula

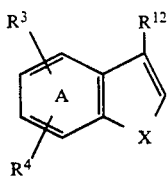

excluding A is phenyl and X is —CH$_2$CH$_2$— wherein R$^{12}$ is an acid, ester or nitrile and the other terms are as defined above.

Other novel intermediates are:

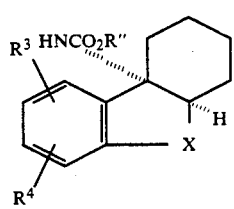

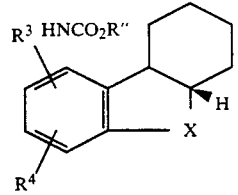

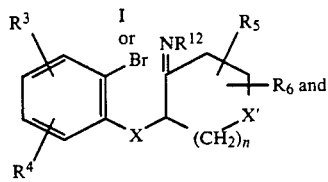

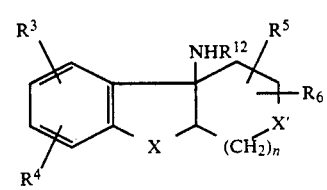

wherein X, X', R$^3$, R$^4$ are as defined above,
R$^{12}$ may be substituted or unsubstituted alkyl, cycloalkyl or arylalkyl, or
R$^{12}$ is SO$_2$R wherein R is (substituted or unsubstituted) alkyl, for example,

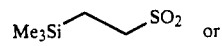

cycloalkyl (for example, a chiral residue such as camphor), arylalkyl (for example, benzyl),
aryl, for example

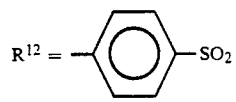

R$^{12}$ is CO$_2$R wherein R is (substituted or unsubstituted), alkyl, cycloalkyl, for example, a chiral residue such as menthol, arylalkyl, or aryl.

Compounds of the instant invention include solvates, hydrates, and salts of the compound of formula I above.

The term lower in connection with organic groups, radical or compounds includes such with up to and including seven members, preferably up to and including four and most preferably one, two, or three carbon atoms except as otherwise specifically described.

Loweralkyl means a straight or branched chain of from one to four carbon atoms including but not limited to methyl, ethyl, propyl, butyl; methyl is the preferred.

Loweralkylene means a group of from one to four carbon atoms, for example, but not limited to methylene, ethylene, 1,2- or 1,3-propylene, 1,2-, 1,3—, or 1,4-butylene.

Loweralkoxy means a group of from one to four carbon atoms, for example, but not limited to methoxy, ethoxy, propoxy; methoxy is the preferred group.

Loweralkylthio means a group of from one to four carbon atoms, for example, but not limited to methylthio, ethylthio, propylthio; methylthio is the preferred group.

A carbocyclic ring means a ring of from three to eight carbon atoms, for example but not limited to cycloheptyl, cyclohexyl, cyclopentyl, cyclobutyl, and cyclopropyl.

Halogen is fluorine, chlorine, bromine, or iodine; fluorine and chlorine are the preferred groups.

Arylloweralkyl means aryl-$C_{1-4}$-alkyl, meaning, for example, benzyl, 2-phenylethyl or 3-phenylpropyl; preferred groups are benzyl.

Monoloweralkylamino means groups containing from one to four carbon atoms, for example, methylamino, ethylamino, n- or i-(propylamino or butylamino).

Diloweralkylamino means a group containing from one to four carbon atoms in each lower alkyl group. For example, dimethylamino, diethylamino, di-(n-propyl)-amino and di-(n-butyl)-amino, or may represent a fused ring, for example, piperidine.

Heterocyclic ring means a bridged or fused di- or tetrahydrothiophene or corresponding di- or tetrahydrofuran.

Physiologically labile group includes but is not limited to such derivatives as are described by; I. H. Pitman in *Med. Chem. Rev.* 2:189 (1981); J. Alexander, R. Cargill, S. R. Michelson and H. Schwam in *J. Med. Chem.* 31:318 (1988); V. H. Naringrekar and V. J. Stella in European Patent Application 214,009-A2 and include certain amides, enaminone derivatives and (acyloxy)alkylcarbamates. Although not limited to these illustrated examples, physiologically labile amine derivatives of the compounds of the instant invention are also disclosed herein.

Salts of the compounds of the invention are preferably pharmaceutically acceptable salts. The compounds of the invention are basic amines from which acid addition salts of pharmaceutically acceptable inorganic or organic acids such as strong mineral acids, for example, hydrohalic, e.g., hydrochloric or hydrobromic acid; sulfuric, phosphoric or nitric acid; aliphatic or aromatic carboxylic or sulfonic acids, e.g., acetic, propionic, succinic, glycolic, lactic, malic, tartaric, gluconic, citric, ascorbic, maleic, fumaric, pyruvic, pamoic, nicotinic, methanesulfonic, ethanesulfonic, hydroxyethanesulfonic, benzenesulfonic, p-toluenesufonic or naphthalenesulfonic acid can be prepared.

For isolation or purification purposes, salts may be obtained which might not be useful for pharmaceutical purposes. However, only pharmaceutically acceptable salts are used for therapeutic purposes and these salts, therefore, are preferred.

The compounds of the present invention may contain asymmetric carbon atoms. The instant invention includes the individual enantiomers, diastereomers, or mixtures thereof which may be prepared or isolated by methods known in the art.

The relative stereochemistry of the fusion of rings B and C may be cis or trans; both are included.

The compounds of the instant invention exhibit valuable pharmacological properties by selectively blocking the N-methyl-D-aspartate sensitive excitatory amino acid receptors in mammals. The compounds are thus useful for treating diseases responsive to excitatory amino acid blockade in mammals.

The effects are demonstrable in in vitro tests or in vivo animal tests using mammals or tissues or enzyme preparations thereof, e.g., mice, rats, or monkeys. The compounds are administered enterally or parenterally, for example, orally, transdermally, subcutaneously, intravenously or intraperitoneally. Forms include but are not limited to gelatin capsules or aqueous suspensions or solutions. The applied in vivo dosage may range between about 0.01 to 100 mg/kg, preferably between about 0.05 and 50 mg/kg, most preferably between about 0.1 and 10 mg/kg.

The ability of the compounds of the instant invention to interact with phencyclidine (PCP) receptors which represents a noncompetitive NMDA antagonist binding site, is shown in Table 1. Tritiated 1[1-(2-thienyl)cyclohexyl]piperidine (TCP) binding, designated RBS1, was carried out essentially as described in *J. Pharmacol. Exp Ther.*, 238, 739–749 (1986).

Since the influx of calcium is thought to be central to the damage resulting from ischemia, the ability of the compounds of the instant invention to inhibit the hypoxia and glutamate-stimulated influx of calcium into cultured rat cortical neurons (an assay representative of cerebrovascular disorders resulting from stroke or brain injury) is shown in Table 2 and Table 3, respectively. The methodology for determining the ability of the compounds of the instant invention to inhibit the glutamate-stimulated Calcium influx (GCI) into cultured rat cortical neurons is to be found in: A. W. Probert and F W. Marcoux. *Soc. Neurosoi. Abstr.* 13, Part II, 754 (1987). Using a similar culture system, the ability of the compounds of the instant invention to inhibit the hypoxia-stimulated influx of calcium (HCI) was determined by incubating cultured cells in an atmosphere of nitrogen (95%) and $CO_2$(5%) at 37° C. for a period of four hours. Calcium influx was determined by subtraction of the stimulated influx in the presence of tetrodotoxin (3 μM) and magnesium (10 mM) from that found in the absence (control) and in the presence of the test substance.

Other compounds of the instant invention show inhibition of [$^3$H]TCP receptor binding with an $IC_{50}$ of less than 200 nM.

TABLE 1

| | | Inhibition of [$^3$H]TCP Receptor Binding | | | | | | | | |
|---|---|---|---|---|---|---|---|---|---|---|
| Example | X | R1 | R2 | R3 | R4 | R5 | R6 | R7 | R8 | RBS1 $IC_{50}$ |
| * | $CH_2$ | $CH_3$ | H | H | H | H | H | — | — | 16 nM |
| * | S | $CH_3$ | H | H | H | H | H | — | — | 10 nM |
| 2 | $CH_2CH_2$ | H | H | H | H | H | H | — | — | 20 nM |
| 4 | $CH_2CH_2$ | $CH_3$ | H | H | H | H | H | — | — | 15 nM |
| 5 | $CH_2CH_2$ | $CH_2CH=CH_2$ | H | H | H | H | H | — | — | 100 nM |
| PCP | — | (reference standard) | | | — | | | | | 40 nM |
| TCP | — | (reference standard) | | | — | | | | | 9 nM |
| ketamine | — | (reference standard) | | | — | | | | | 860 nM |
| MK-801 | — | (reference standard) | | | — | | | | | 3 nM |

TABLE 2

Inhibition of Glutamate Stimulated [$^{45}$Ca] Influx (CGCI)

| Example | X | R1 | R2 | R3 | R4 | R5 | R6 | R7 | R8 | CGCI IC$_{50}$ |
|---|---|---|---|---|---|---|---|---|---|---|
| * | CH$_2$ | CH$_3$ | H | H | H | H | H | — | — | 304 nM |
| * | S | CH$_3$ | H | H | H | H | H | — | — | 210 nM |
| 2 | CH$_2$CH$_2$ | H | H | H | H | H | H | — | — | 100 nM |
| 4 | CH$_2$CH$_2$ | CH$_3$ | H | H | H | H | H | — | — | 410 nM |
| 5 | CH$_2$CH$_2$ | CH$_2$CH=CH$_2$ | H | H | H | H | H | — | — | 902 nM |
| — | PCP | (reference standard) | | | | — | | | | 160 nM |
| — | ketamine | (reference standard) | | | | — | | | | 5500 nM |
| — | MK-801 | (reference standard) | | | | — | | | | 51 nM |

TABLE 3

Inhibition of Hypoxia Stimulated [$^{45}$Ca] Influx (CHCI)

| Example | X | R1 | R2 | R3 | R4 | R5 | R6 | R7 | R8 | CGCI IC$_{50}$ |
|---|---|---|---|---|---|---|---|---|---|---|
| * | CH$_2$ | CH$_3$ | H | H | H | H | H | — | — | — |
| * | S | CH$_3$ | H | H | H | H | H | — | — | 180 nM |
| 2 | CH$_2$CH$_2$ | H | H | H | H | H | H | — | — | 50 nM |
| 4 | CH$_2$CH$_2$ | CH$_3$ | H | H | H | H | H | — | — | 180 nM |
| 5 | CH$_2$CH$_2$ | CH$_2$CH=CH$_2$ | H | H | H | H | H | — | — | 660 nM |
| — | PCP | (reference standard) | | | | — | | | | 45 nM |
| — | ketamine | (reference standard) | | | | — | | | | 1900 nM |
| — | MK-801 | (reference standard) | | | | — | | | | 34 nm |

Methods of synthesis of compounds of the instant invention are discussed in *J. Org. Chem.*, 28, 1112 (1963). These methods may be adapted to provide the new compounds of the instant invention. These and additional methods of preparation are illustrated in Schemes I-X following.

The saturated intermediate tricyclic acids (7) are available through an annulation procedure outlined by G. Sinha et al, in *J. Chem. Soc. Perkin. Trans.* 1, 2519 (1983). Alternately, the unsaturated tricyclic acids (6) are available through the Diels-Alder addition of dienes, for example butadiene, to the unsaturated acids, esters or nitriles (5,24,4) as illustrated in Schemes I and IV. These unsaturated acids and esters may be prepared from the ketones, as illustrated in Schemes I and VII. These Diels-Alder reactions may be carried out neat or in a solvent, for example, toluene or more preferably water and over a range of temperatures, for example, 100°-200°, preferably 120°14 180°. They may also be carried out, where appropriate, in the presence or absence of a catalyst, for example, trimethylaluminum or diethylaluminum chloride, and with the addition of butylated hydroxytoluene which acts as a radical scavenger to suppress undesirable polymerization reactions. The ring C unsaturation may be removed at this point by catalytic hydrogenation over palladium catalyst to yield the saturated acids (7).

The transformation of the acid moieties of 6 or 7 into the isocyanate (8) may be carried out by heating the free acids with diphenylphosphoryl azide and base, for example, triethylamine, or conversely, may be achieved by heating the corresponding acid chloride with sodium azide in a solvent such as benzene in the presence of a catalytic amount of a phase transfer catalyst, for example, 18-crown-6 or 15-crown-5 crown ethers. The compounds of the instant invention may be derived from the isocyanates (8) by basic hydrolysis or by reduction by, for example, lithium aluminum hydride, of the corresponding carbamates. This compound is prepared in turn from the isocyanate (8) by heating with an anhydrous alcohol. An additional aspect of this invention involves the use of alcohols which afford carbamates which may be degraded by mild methods which are shown in Scheme I. Such alcohols include, for example, 2-trimethylsilylethanol, or 2,2,2-trichloroethanol.

A further aspect of the invention involves the use of chiral alcohols to afford diastereomeric carbamates. Such alcohols include α-methylbenzyl alcohol or menthol. Such diastereomeric carbamates may, in certain instances, permit the chromatographic resolution of diastereomeric pairs to afford optically pure diastereomers, thus allowing resolution of the disclosed amines into pure optical isomers. Additional compounds of the instant invention may be further prepared by acylation, carbamoylation, or alkylation of the free or substituted amine. This transformation may be carried out using an alkyl halide, for example allyl bromide and a base, for example triethylamine in a solvent, for example, ethanol or, for example, by reductive amination of an aldehyde such as formaldehyde or acetaldehyde.

Unsaturation may be introduced into the B ring as illustrated in Scheme II. Bromination of the acid or ester (13) may be carried out by heating the unsaturated precursor with a brominating agent, for example N-bromosuccinimide in the presence of a radical initiator, for example azoisobutyronitrile. Elimination of the bromide may be achieved by heating with a base, for example triethylamine or 1,8-diazabicyclo[5.4.0]undec-7-ene (DBU). Alternatively, 15 may be prepared from the ketone which is available by chromium trioxide oxidation of 7 or its ester, 13. Reduction of the ketone to the alcohol, for example, with sodium borohydride in methanol followed by acid catalyzed dehydration also affords the unsaturated ester, 15. Transformation of these intermediates into compounds of the instant invention is carried out as previously described.

In addition to Diels-Alder cycloaddition methodology, (summarized in Scheme IV), compounds of the instant invention, where X is, for example, —CHR$^7$S— and —SCHR$^7$— may also be prepared by a routes illustrated in Scheme V. Alkylation of the enolate anion, for example, sodium enolate, of cyclohexanone or an enamine, for example, 1-pyrrolidino-1-cyclohexene, with an alkyl halide, for example, 2-(chloromethylthio)-bromobenzene gives the corresponding ketone (27).

Methodology for the cyclization of imines derived from the ketones (27) to compounds of the instant invention is illustrated in Scheme IX.

The compounds of the instant invention where Ring A is a thiophene can be prepared as shown in Scheme VII and by methods similar to that shown in Scheme I. The synthesis of 4,5-dihydrobenzo[b]thiophen-6(7)-one, (38a), 6,7-dihydrobenzo[b]thiophen5(4)-one (38b), and 6,7-dihydrobenzo[c]thiophen5(4)-one (38c) are described by Padwa et al in *J. Org. Chem.*, 54, 299 (1989). An alkoxy carbonyl group, for example, methoxycarbonyl, can be introduced into each of these compounds by the simultaneous action of a strong anhydrous base, for example, sodium hydride and a dialkylcarbonate group, for example, dimethylcarbonate. The dimethylcarbonate may be used as the solvent. Using the route shown in Scheme VII, the alkoxycarbonylated intermediates are reduced, for example, with sodium borohydride in an alcohol, for example, methyl alcohol to the corresponding alcohols (40a,b,c). Dehydration of (40a,b,c), which may be achieved by heating in the presence of an acid, for example, toluene sulfonic acid with continuous removal of water, using, for example, a Dean and Stark trap gives the unsaturated esters (41a,b,c). These unsaturated esters may be transformed into the compounds of the instant invention by a Diels-Alder cycloaddition reaction. Such a reaction is carried out by heating the substrate in the presence of a diene, for example, butadiene, in the absence or presence of a solvent, for example, toluene, or water in a manner similar to that shown in Schemes I and IV. Hydrolysis of the ester group may be carried out by treating the substrate with alkalie, for example, aqueous or alcoholic sodium hydroxide or anhydrous potassium trimethylsilanolate. Rearrangement of the acid into the required isocyanate may be carried out by heating the acid in the presence of diphenylphosphoryl azide and triethylamine in a solvent, for example, benzene. Alternatively, activation of the acid, for example, by the generation of an acid chloride, for example, by heating the acid in the presence of thionyl chloride, followed by heating with sodium azide in the presence or absence of a phase transfer catalyst, for example, 18-crown-6 or 15-crown-5 crown ethers in a nonprotic solvent, for example, benzene also affords the intermediate isocyanates (46a,b,c). The isocyanates (46a,b,c) may be transformed into the compounds of the instant invention by hydrolysis in the presence of a strong base, for example, aqueous sodium hydroxide followed by acidification with, for example, hydrochloric acid to give the compounds in which $R^1$ and $R^2$ are both hydrogen. The free amino may be further alkylated by an alkyl halide, for example, benzyl bromide or allyl bromide in the presence of a base, for example, triethylamine or DBU to give further compounds of the instant invention. Alternatively, the isocyanate may be transformed further by the addition of an alcohol, for example, ethyl alcohol to give a carbamate. Reduction of the resultant carbamate with a strong reducing agent, for example, lithium aluminum hydride, gives the compounds of the instant invention wherein $R^1$ is methyl and $R^2$ is hydrogen.

Alternatively, to assemble Ring C, the saturated acids (45a,b,c) may be prepared from compounds 39a,b,c by a Robinson annulation in a manner similar to that described by Sinha et al in *J. Chem. Soc. Perkin Trans. I*, 2519 (1983). In this (Scheme VIII), in the presence of a strong base, for example, Triton-B methoxide in a protic solvent, for example, methyl alcohol, methyl vinyl ketone is added to the compounds 39a,b,c to give the tricyclic intermediates 42a,b,c. Dehydration of 42a,b,c, which may be achieved by heating in the presence of an acid, for example, toluene sulfonic acid with continuous removal of water, using, for example, a Dean and Stark trap gives the unsaturated esters 43a,b,c. Reduction with a hydride reducing agent, for example, diisobutylaluminum hydride or catalytic hydrogenation or a dissolving metal reduction, for example, lithium in liquid ammonia, followed by Wolff Kishner deoxygenation gives the acids 45a, b, or c. This deoxygenation may be carried out by heating the substrate with hydrazine and potassium hydroxide in a solvent, for example, diethylene glycol at elevated temperatures, for example, 200°–270°, preferably 220°–245°. These are transformed further into the compounds of the instant invention in a manner similar to that described above.

Alternatively, as may be required by the nature of the substituents, the hydroxyl group of the intermediates 42a,b,c may be removed by an alternate dissolving metal reduction of a derived ester according to the method of Boar et al, *J. Chem. Soc. Chem. Comm.* 68 (1978). Prior to this reduction, protection of the existing ketone residue may be required, this may be achieved, for example, by the formation of a silyloxy derivative, for example, a t-butyldimethylsilyl group. Alternatively, the ketone may be protected as a ketal, for example, an ethylene ketal.

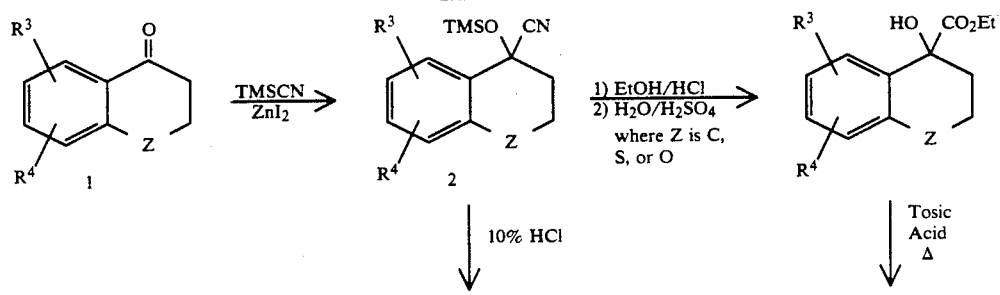

SCHEME I

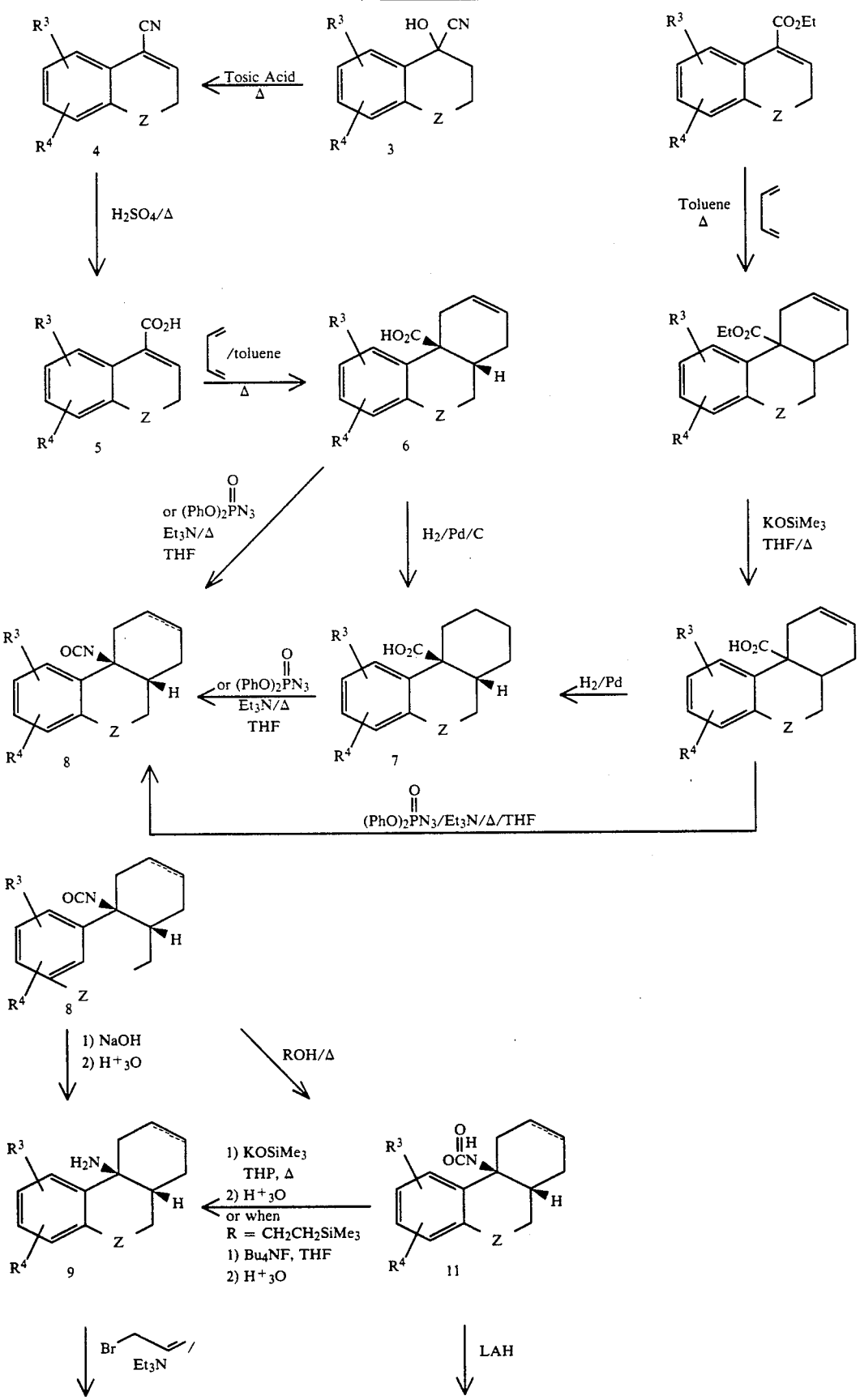

-continued
SCHEME I
where R is substituted or unsubstituted alkyl, cycloalkyl, aryl or arylalkyl, where the substitutent may be further selected to aid in chiral resolution or facilitate deprotection of the carbamate.
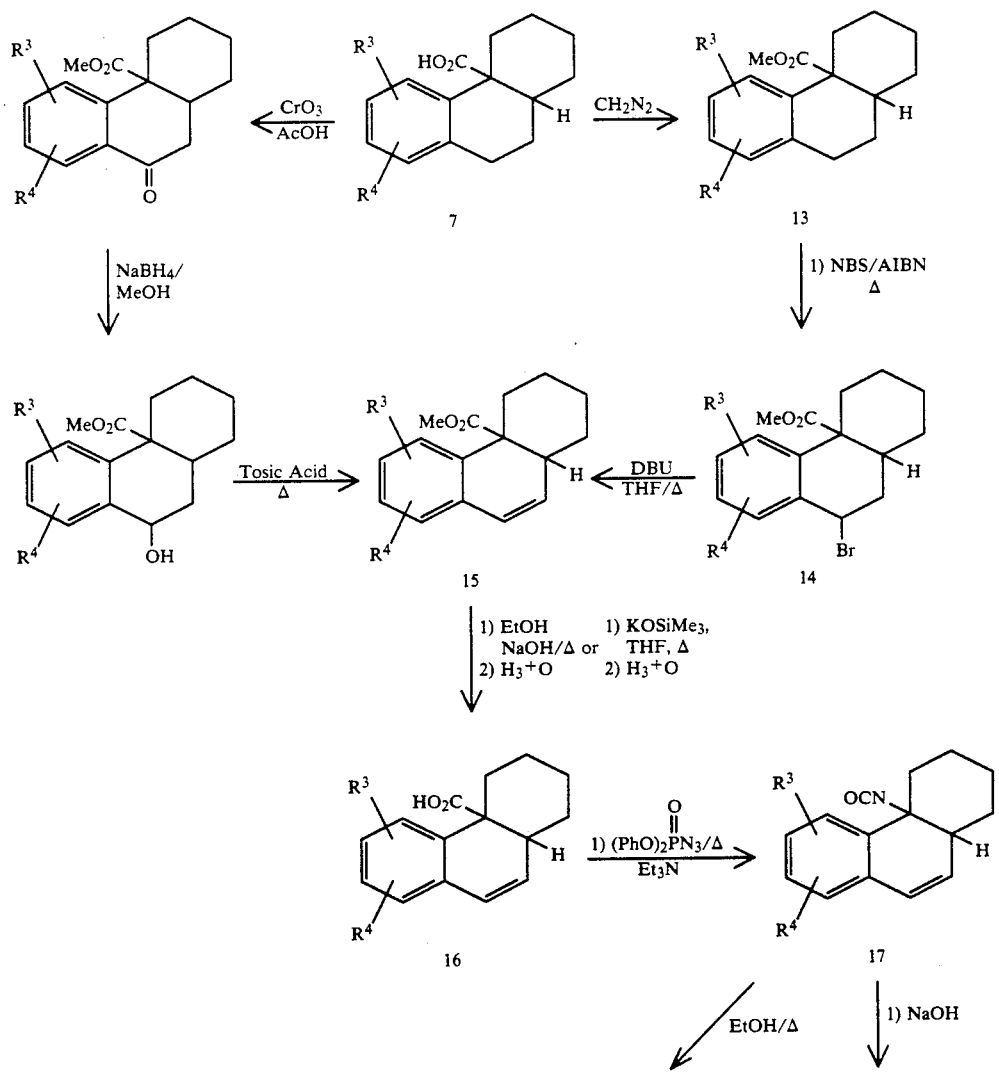

-continued
SCHEME II
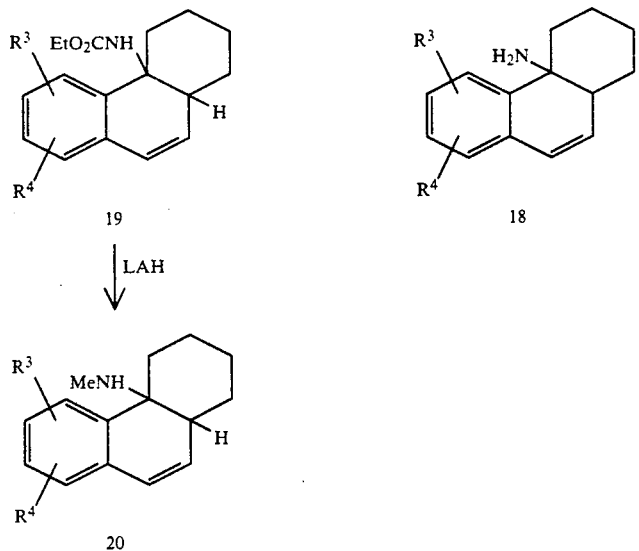
SCHEME IV
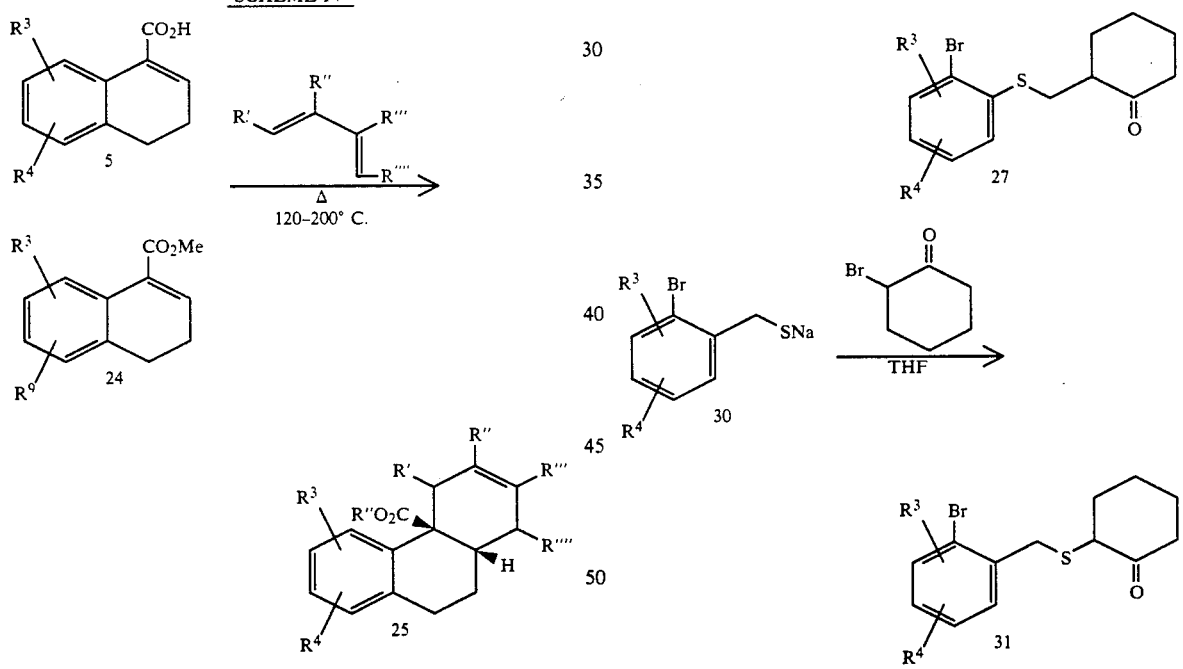
and R'R"R'"R"" may be independently H, alkyl, OMe, OSiMe₃
R'—R"" may be part of a ring.
SCHEME V
SCHEME VI
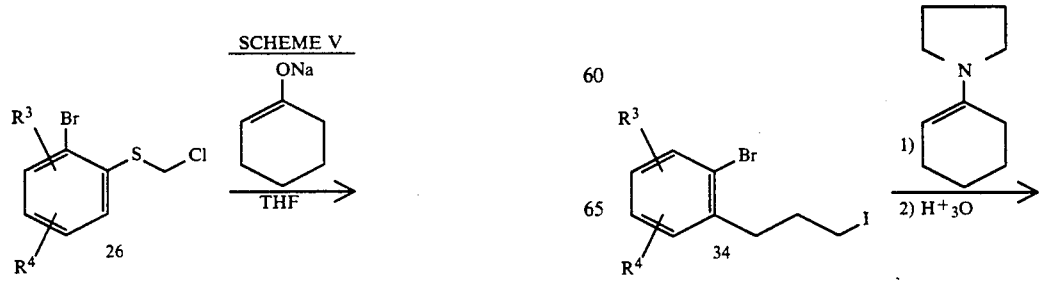

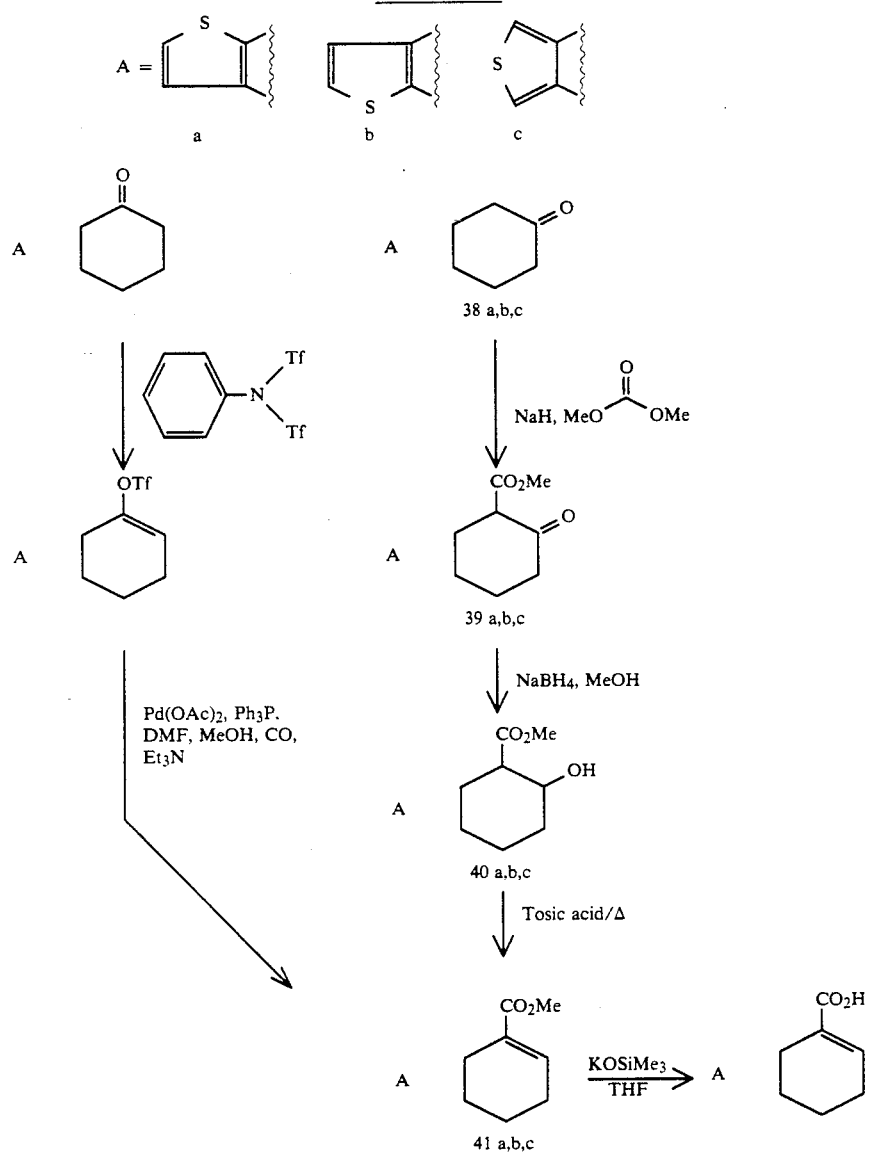
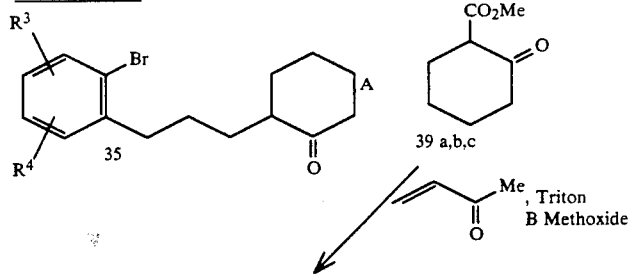

5,180,736
-continued
SCHEME VIII
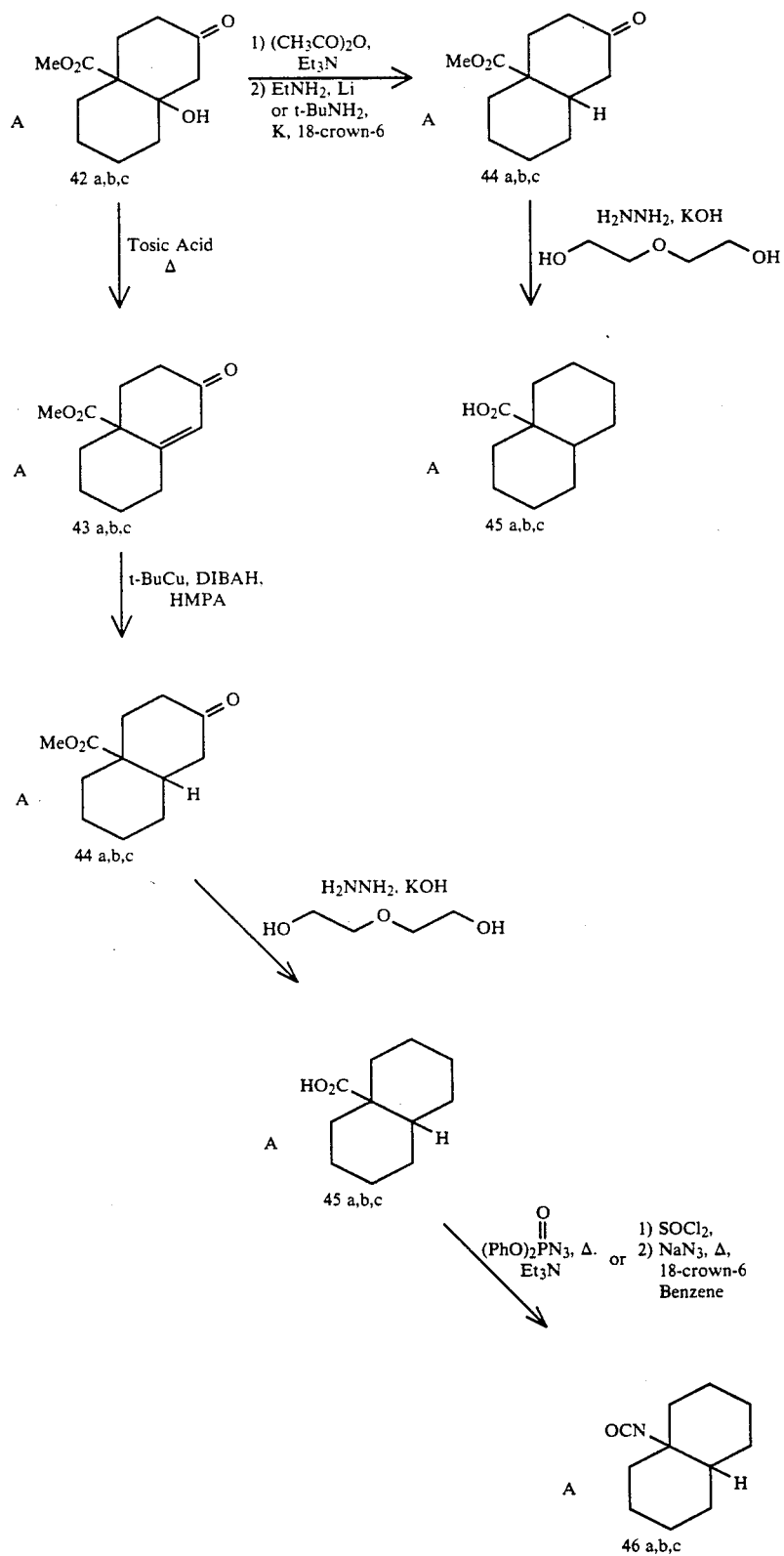

SCHEME IX

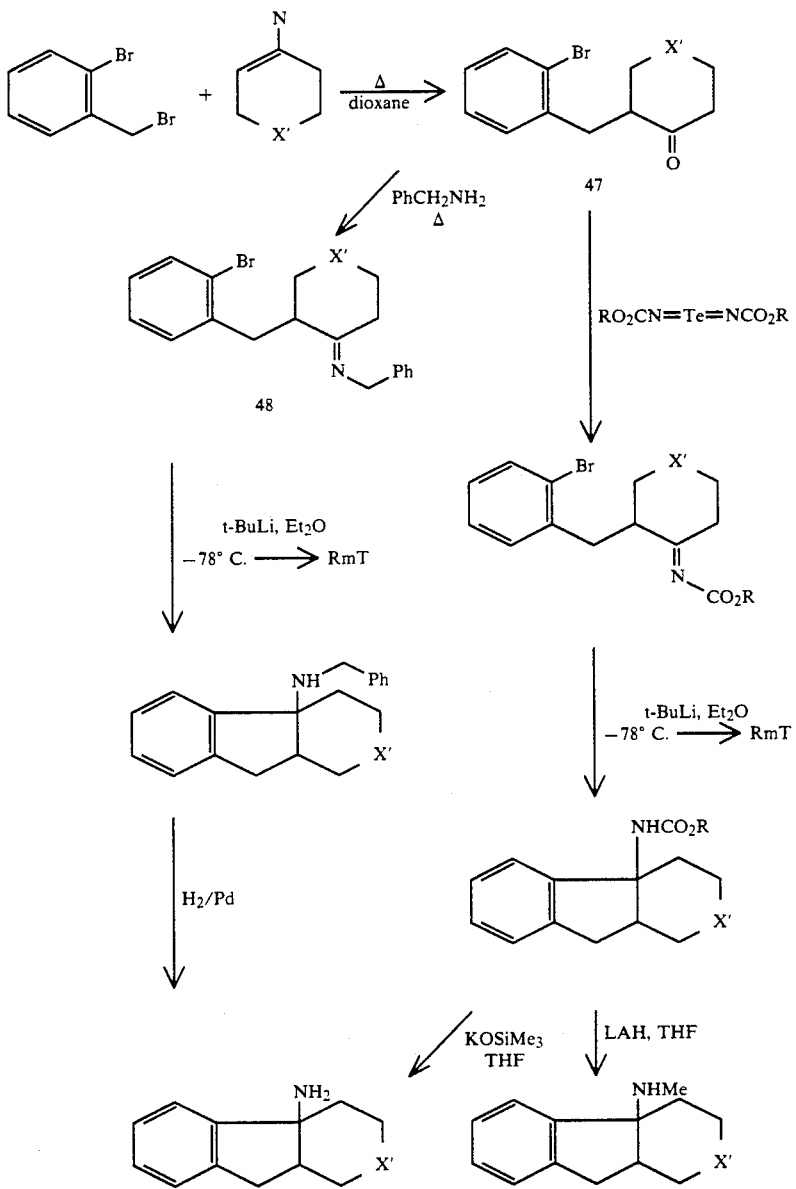

SCHEME X

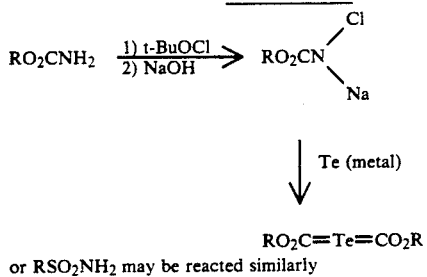

or RSO$_2$NH$_2$ may be reacted similarly
to give RSO$_2$N=Te=NSO$_2$R

The compounds of the instant invention may also be prepared by cyclization of an aromatic anion onto a preformed imine as shown in Scheme IX. Coupling of an ortho substituted haloalkyl aromatic bromide with a cycloalkyl enamine in a solvent such as dioxane at elevated temperature, for example, at reflux, affords the arylalkylcycloalkylketone (47). Alternatively (47) may be prepared by the reaction of a haloalkylaromatic bromide with the preformed cycloalkyl ketone enolate anion. Treatment of the ketone (47) with an amine under dehydrating conditions, for example, heating the ketone with an amine in a solvent, for example, toluene, at elevated temperatures, for example, at reflux in the presence of a catalyzing amount of an acid, for example, toluenesulfonic acid, with the simultaneous removal of water, for example, by the use of a Dean and Stark trap, affords the imine (48). Alternatively, an imine may be prepared by an aza Wittig reaction. That is, by treating the ketone with a phosphonoimine derived from the reaction of an azide, for example, benzylazide with a triaryl or trialkylphosphine, for example, triphenylphosphine to give

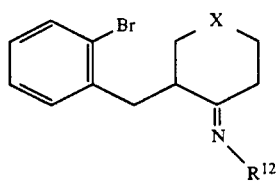

wherein $R^{12}$ is alkyl, cycloalkyl, arylalkyl, aryl, $SO_2R$, or $CO_2R$.

Alternatively, an imine may be prepared by method described in J. Org. Chem. 1990, 55, 393 or by the treatment of the ketone with a telluriodiimide derived from the reaction of an N-chloro-N-sodiocarbamate or sulfonamide with tellurium metal (Scheme X). Alternatively, the equivalent seleniodiimide may also be used. This imination reaction may be carried out in an inert solvent such as dichloromethane or acetonitrile. The by-products of tellurium or selenium dioxide may be optionally removed by filtration prior to cyclization of the derived alkyl or arylsulphonyl or alkoxycarbonyl substituted imine.

Cyclization of the bromoarylcycloalkyl imines is achieved by treating the substrate with a strong base, for example, t-butyllithium, in an anhydrous inert solvent such as ether, or tetrahydrofuran at reduced temperatures, for example, $-78°$ C. Following the addition of base at low temperatures and subsequent stirring, the reaction is warmed to room temperature before quenching. Quenching may be achieved by the addition of an aqueous ammonium chloride solution followed by extraction of the product with a solvent such as dichloromethane. The product of cyclization may be isolated and purified by methods known to those skilled in the art.

Following cyclization, the alkyl or aryl sulfonyl residue may be removed from the amino group by methods known to those skilled in the art. Alternatively, the product of cyclization onto an alkoxycarbonylimine is a carbamate. Further reactions of such a substrate are developed in Schemes I and II.

It will be apparent to those skilled in the art that the methods described above are illustrative only and are not meant to limit the scope of the instant invention. Alternate transformations and reagents to those disclosed above by which the compounds of the instant invention may also be prepared will be apparent to those skilled in the art.

In starting compounds and intermediates which are converted to the compounds of the instant invention, functional groups such as carboxy, amino and hydroxy groups are optionally protected by conventional protecting groups that are common in preparative organic chemistry. Protected carboxy, amino, and hydroxy groups are those that can be converted under mild conditions into free carboxy, amino, and hydroxy groups without the molecular framework being destroyed or other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxy group, amino group, etc), the structure and stability of the molecule of which the substituent is a part, and the reaction conditions.

Well-known protecting groups that meet these conditions and their introduction and removal are described, for example, in J. F. W. McOmie, Protective Groups in Organic Chemistry, Plenum Press, London, New York (1973), T. W. Greene, Protective Groups in Organic Synthesis, Wiley, New York (1981), and also in The Peptides, Vol. I, Schroeder and Luebke, Academic Press, London, New York (1965), as well as in Houben-Weyl, Methoden der Organischen Chemie, Vol. 15/1, Georg Thieme Verlag, Stuttgart (1974).

Terms used in the processes of the instant invention are defined below.

A diene means a group containing two alkene bonds in conjugation such a group contains a least four contiguous carbon atoms but may also contain a greater number of additional carbon or heteroatoms. An alicyclic diene is for example, butadiene, 2,3-dimethylbutadiene or chlorobutadiene. A cyclic butadiene is, for example, cyclohexadiene, cycloheptadiene or thiophene.

The conversion of cyano to carboxy may be carried out directly by treatment with a strong aqueous acid, for example 40% sulfuric acid. The conversion of cyano to a carboxylic acid may also be carried out in several steps, for example by treatment first with a lower alkanol, e.g., anhydrous ethanol, in the presence of a strong acid, e.g., hydrochloric acid, to give an alkoxyimidate when carried out at reduced temperature, for example, $5°$ C. or, when carried out at elevated temperature the alkoxycarbonyl intermediate may be obtained directly. This intermediate may be subsequently hydrolyzed further with acid or base.

Alternatively, a cyano group may be first transformed into a amide, this is preferably carried out by treatment with an alkali metal hydroxide, e.g., dilute sodium hydroxide and hydrogen peroxide, preferably at room temperature. The resultant amide may be further hydrolyzed with acid or base into the carboxylic acid. Alternatively, the intermediate amide may be transformed directly into an isocyanate, this is preferably carried out by treatment of the amide with a positive halogen source, for example bromine or sodium hypochlorite in the presence of a base, for example sodium hydroxide. The isocyanate may be hydrolyzed directly to the amines of the instant invention, preferably by treatment with a strong base for example sodium hydroxide.

The compounds of the invention may thus also be converted to other compounds of the invention by functional group transformations well known in the art.

For example, conversion of carboxylic acid esters and amides to carboxylic acids is advantageously carried out by hydrolysis with inorganic acids such as a hydrohalic or sulfuric acid or with aqueous alkalies, preferably alkali metal hydroxides such as lithium or sodium hydroxide.

Free carboxylic acid may be esterified with lower alkanols, such as ethanol, in the presence of a strong acid, e.g., sulfuric acid, or with diazo (lower) alkanes, e.g., diazomethane, in a solvent such as ethyl ether, advantageously at room temperature, to give the corresponding lower alkyl esters.

The above-mentioned reactions are carried out according to standard methods, in the presence or absence of diluents, preferably such that are inert to the reagents and are solvents thereof, of catalysts, of condensing or said other agents respectively and/or in inert atmospheres, at low temperatures, room temperature or elevated temperatures, preferably at the boiling point of the solvents used, and at atmospheric or super-atmospheric pressure. The preferred solvents, catalysts, and reaction conditions are set forth in the appended illustrative examples.

The invention further includes any variation of the present processes in which an intermediate product obtainable at any stage is used as starting material and the remaining steps are carried out, or the process is discontinued at any stage. The reaction components may be used in the form of their salts or optically pure antipodes.

The following examples are illustrative of the instant invention and are not intended to limit the scope. All evaporations are performed under reduced pressure, preferably between about 2 and about 13KPa.

EXAMPLE 1

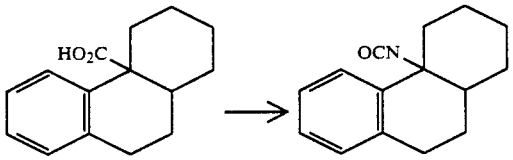

Cis-1,2,3,4,4a,9,10,10a-octahydro-4a-isocyanato-phenanthrene

A solution of cis-1,3,4,9,10,10a-hexahydro-4a(2H)-phenanthrene-carboxylic acid, (3.22 g, 1.42 mmol), (prepared by the method of G. Sinha, et al, *J. Chem. Soc. Perkin. Trans.* 1:2519 (1983)), in fresh thionyl chloride (25 ml) was refluxed for one hour. The solvent was evaporated and the crude product was dissolved in dry benzene (25 ml). Sodium azide (1 g) and 18-crown-6 crown ether (0.06 g) was added and the solution was refluxed for 18 hours. The solution was filtered and evaporated in vacuo to yield a mobile light brown oil which was chromatographed to yield the title compound as a pale yellow oil (2.9 g, 90%).

EXAMPLE 2

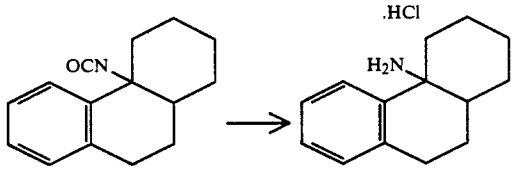

Cis-1,3,4,9-10,10a-hexahydro-4a(2H)-phenanthrenamine monohydrochloride

To a solution of the compound from Example 1 (0.92 g, 4.05 mmol) in benzene (15 ml) was added a solution of potassium hydroxide in water (5 g in 5 ml). The mixture was stirred vigorously and to it was added 18-crown-6 crown ether (0.01 g). The solution was stirred for 18 hours and then diluted with benzene and acidified to pH 1 with hydrochloric acid. The aqueous acidic solution was layered with ether and basified with sodium hydroxide and extracted with ether. The ether solution was washed with water and then dried (MgSO₄), filtered, and evaporated to give a pale oil. The oil was taken up in fresh ether and treated with dry isopropanolic HCl. The white solid which formed was filtered and dried in vacuo to yield the title compound (0.55 g) which could be recrystallized from methanol/ether to give a white solid, mp 223°-225° C. (dec).

EXAMPLE 3

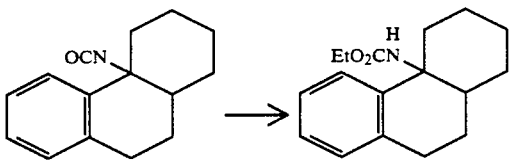

Ethyl cis-(1,3,4,9,10,10a-hexahydrophenanthren-4a(2H)-yl)-carbamic acid

A solution of crude compound from Example 1 (0.57 g, 2.50 mmol) was dissolved in absolute ethanol (10 ml) and refluxed for 18 hours. The solution was evaporated in vacuo and chromatographed on silica gel eluting with ethyl acetate/heptane to yield the title compound as a colorless oil (0.46 g, 67%).

EXAMPLE 4

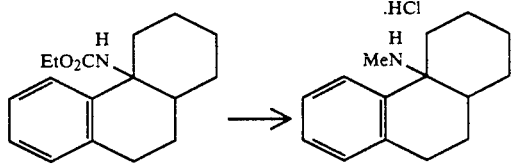

Cis-1,3,4,9,10,10a-hexahydro-N-methyl-4a(2H)-phenanthrenamine monohydrochloride

A solution of compound of Example 3 (0.4 g, 1.5 mmol) in dry ether (5 ml) was added slowly to a stirred solution of lithium aluminum hydride (0.54 g, 14.0 mmol) in ether (30 ml). The solution was stirred for 24 hours and then quenched by the careful addition of water (1 ml), sodium hydroxide (25%, 1 ml), and water (5 ml). The suspension was filtered through Hyflow. The ether solution was concentrated to 10 ml and treated with isopropanolic HCl. The white solid obtained was dried in vacuo to give the title compound (0.26 g, 70%), mp 227°-282° C. (dec).

EXAMPLE 5

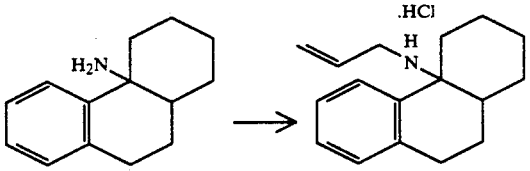

N-Allyl-cis-1,3,4,9,10,10a-hexahydro-4a(2H)-phenanthrenamine monohydrochloride

To a solution of the compound of Example 2 (free amine) (0.57 g) in ethanol (8 ml) was added allyl bromide (0.34 g) and triethylamine (0.27 g). The solution was stirred for 56 hours. The solution was evaporated in vacuo and taken up in ether and washed with dilute hydrochloric acid. The aqueous solution was layered

EXAMPLE 6

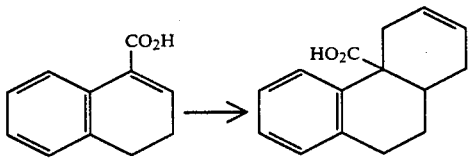

Cis-1,9,10,10a-tetrahydro-4a(4H)-phenanthrenecarboxylic acid

To a solution of 3,4-dihydronaphthalene-1-carboxylic acid (29.7 g) in toluene (75 ml) was added butadiene (16 g) and a trace of butyrated hydroxy toluene (BHT). The solution was heated to 180° for 18 hours in a sealed reactor, then chromatographed twice over silica gel. Recrystallization from ethyl acetate/heptane affords the title compound as a colorless crystalline solid (10.5 g). The recovered starting material was reereacted with butadiene to afford, after workup, additional title product (8.0 g).

EXAMPLE 7

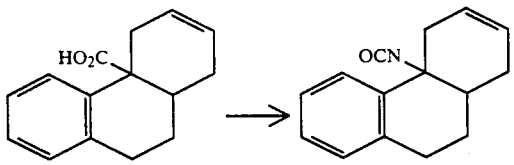

Cis-1,4,4a,9,10,10a-hexahydro-4a-isocyanatophenanthrene

A solution of the compound of Example 6 (2.0 g) in fresh thionyl chloride (25 ml) was refluxed for 1 hour. The thionyl chloride was evaporated in vacuo and the residue taken up in benzene to which sodium azide (0.85 g) and 18-crown-6 crown ether (0.06 g) was added. The suspension was refluxed overnight, then filtered through Hyflo, reduced in volume and chromatographed over silica gel to afford the title compound as a colorless oil (1.45 g, 74%).

EXAMPLE 8

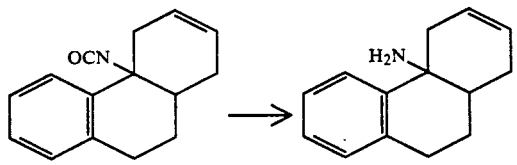

Cis-4,9,10,10a-tetrahydro-4a(2H)-phenanthrenamine

Using the method outlined in Example 2, the compound of Example 7 (0.73 g) was transformed into the title compound (0.64 g, 83%), mp 247°-248° C. (dec).

EXAMPLE 9

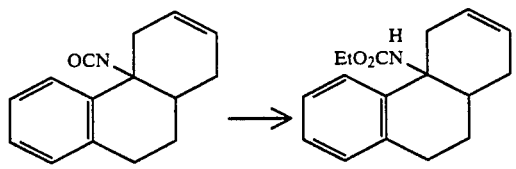

Ethyl cis-(1,9,10,10a-tetrahydrophenanthren-4a(4H)-yl)carbamic acid

Using the method outlined in Example 3, the compound of Example 7 (0.72 g) was transformed into the title compound. This material was taken on without further purification.

EXAMPLE 10

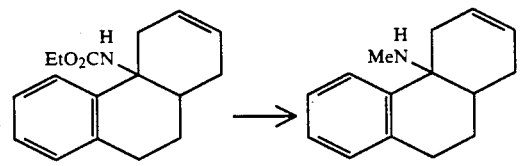

Cis-1,9,10,10a-tetrahydro-N-methyl-4a(4H)-phenanthrenamine

Using the method outlined in Example 4, the compound of Example 9 was transformed into the title compound (0.70 g, 87% overall yield from Example 7), 224°-227° C. (dec).

In a similar manner to Examples 29, 30, 1, 3, and 4, cis-1,9,10,10a-tetrahydro-N-methyl-9-methyl-4a(4H)-fluorenamine is prepared from 3-carboxy-1-methylindene.

EXAMPLE 14a

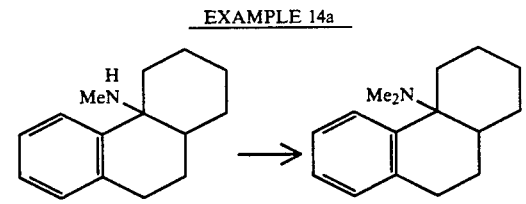

1,3,4,9,10,10a-Hexahydro-N,N-dimethyl-4a(2H)-phenanthrenamine

To a solution of the compound obtained in Example 4 (1.0 g) in methanol (15 ml) was added aqueous formaldehyde (5 ml, 35%) and in one batch sodium cyanoborohydride (1 g). The reaction was stirred overnight then the solvent removed in vacuo. The residue was taken up in ether and washed with dilute sodium hydroxide, water and finally 2N HCl. The aqueous acid solution was layered with fresh ether and basified with sodium hydroxide solution. The ether layer was washed with water and brine then dried (NaSO4). The ether layer was reduced in volume then to was added slowly an

--- with fresh ether, basified with sodium hydroxide, and extracted. The ether layer was washed with water and then brine, dried (MgSO4) and evaporated to a colorless oil. The oil was chromatographed over silica gel, eluting with ethyl acetate/heptane mixtures to afford on evaporation a colorless oil. The oil was taken up with ether (15 ml) and treated with isopropanolic HCl to afford a white solid which was dried in vacuo to give the title compound (0.17 g, 25%), mp 211°-213° C. (dec).

EXAMPLE 15

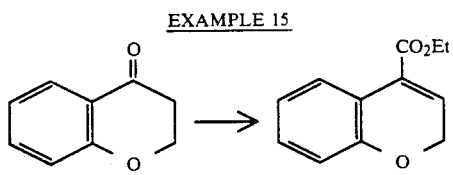

Ethyl 2H-1-benzopyran-4-carboxylate

To a solution of chromanone (31.1 g, 210 mmol) in dichloromethane (200 ml) was added trimethylsilylcyanide (25 g, 250 mmol), potassium cyanide (2.0 g) and 18-crown-6 crown ether (0.5 g). The solution was stirred overnight then evaporated to a dark oil. The oil was dissolved in dichloromethane (100 ml) and added slowly to a cooled (5° C. saturated ethanolic HCl solution (500 ml) such that the temperature remained between 5°-6° C. The solution was set aside for 18 hours at 5° C. Then the solvent was evaporated in vacuo to leave a red oil which was layered with ether (550 ml) and to it was added 1N sulfuric acid (250 ml) followed by water (250 ml). The mixture was stirred for 2.5 hr then organic phase was washed with water then brine and dried (Na2SO4). The solvent was evaporated in vacuo to afford a red/brown oil (40 g) which was dissolved in benzene (500 ml) to which toluene sulfonic acid (3 g) had been added. The solution was refluxed with removal of water (Dean-Stark trap) for 1.5 hours. The solution was cooled and washed with water, saturated sodium bicarbonate and finally brine. The solution was dried (Na2SO4) and concentrated in vacuo diluted with heptane and chromatographed on silica gel to give the title product as a oil (20.57 g, 48%).

EXAMPLE 16

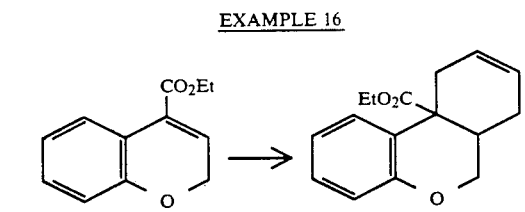

Ethyl 6,6a,7,10-tetrahydro-10aH-dibenzo[b,d]pyran-10a-carboxylate

A solution of the product of Example 15 (20.3 g) was dissolved in toluene (100 ml) and to it was added BHT (0.5 g) and butadiene (73 g) the reaction vessal was pressurized with nitrogen (1900 psi) and heated to 50° C. for 6 days. The resulting syrup (40 g) was partitioned between heptane and acetonitrile. The acetonitrile solution was washed with fresh heptane then evaporated in vacuo. The heptane phase was extracted with fresh acetonitrile which was evaporated to give a further recovery of crude product. The resulting oils were chromatographed on silical gel (eluting with ethyl acetate:heptane (1:60)), to give the title compound as a crystalline solid (10.1 g, 38%), mp 88° C.

EXAMPLE 17

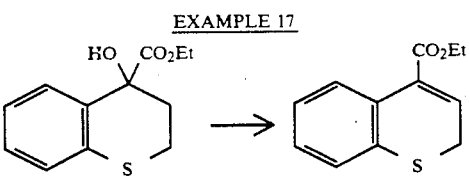

Ethyl 2H-1-benzothiopyran-4-carboxylate

In a manner similar to that described in Example 15, ethyl 3,4-dihydro-4-hydroxy-2H-1-benzothiopyran-4-carboxylate (16 g) was dehydrated in refluxing toluene to give in quantitative yield after chromatography the title compound as a mobil oil (15.4 g).

EXAMPLE 18

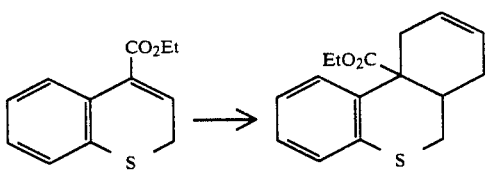

Ethyl 6,6a,7,10-tetrahydro-10aH-dibenzo[b,d]thiopyran-10a-carboxylate

In an manner similar to that described in Example 16 the product of Example 17 was reacted with butadiene to give the title compound as a yellow oil (8.57 g, 44%).

EXAMPLE 19

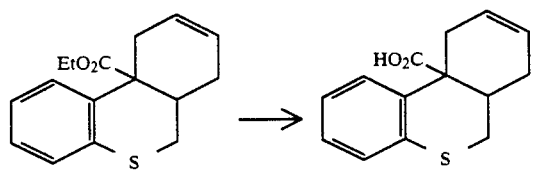

6,6a,7,10-Tetrahydro-10aH-dibenzo[b,d]thiopyran-10a-carboxylic acid

To a solution of the product from Example 18 (7.36 g) in tetrahydrofuran (200 ml) was added potassium trimethylsilanolate (5.30 g). The solution was refluxed for 7 hours then diluted with heptane and filtered. The precipitated solid was dissolved in water/ethyl acetate and acidified with dilute hydrochloric acid. The organic phase was washed with water then extracted with dilute sodium hydroxide (x2). The aqueous layer was washed with ethyl acetate then layered with fresh ethyl acetate and acidified. The solution was washed with water and dried (Na2SO4) and evaporated to a oil which was triturated with ethyl acetate/heptane to give the title compound as a cream colored solid (4.5 g), mp 152°-155° C. and a darker colored second crop (1.7 g) combined yield 94%.

EXAMPLE 20

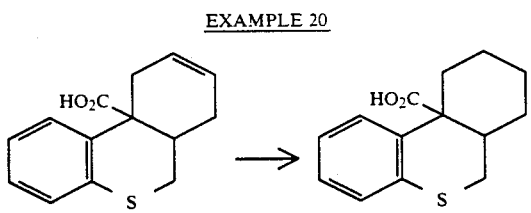

6,6a,7,8,9,10-hexahydro-10aH-dibenzo[b,d]thiopyran-10a-carboxylic acid

To a solution of the product from Example 19 (4.35 g) in methanol (100 ml) was added palladium on charcoal 5%, 0.5 g). The solution was hydrogenated (50 psi) and the suspension filtered through Hyflo. Evaporation of solvent gave the title compound as a colorless crystalline solid (3.5 g). Treatment of the catalyst residue with hot methanol afforded the remaining of the title compound (0.8 g), mp 200°-203° C.

EXAMPLE 21

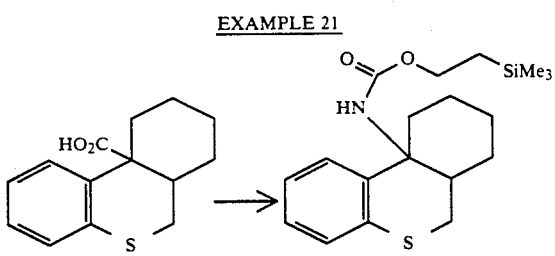

2-(Trimethylsilyl)ethyl 6,6a,7,8,9,10-hexahydro-10aH-dibenzo[b,d]thiopyran-10a-yl carbamate To a solution of the product from Example 20 (4.03 g) in dry toluene (125 ml) was added diphenylphosphoryl azide (4.6 g) and triethylamine (1.8 g). The solution was refluxed under a nitrogen atmosphere for 1 hour, cooled and washed with water then dried ($Na_2SO_4$). Evaporation of the solvent in vacuo afforded a pale yellow oil (4.5 g) which was dissolved in trimethylsilylethanol (15 ml) and heated to 100° C. for 1 hour then 95° C. for 20 hours. The solvent was evaporated in vacuo and the residue was chromatographed on silica gel to afford the title compound as a colorless oil which crystallized on standing (5.24 g, 88%).

EXAMPLE 22

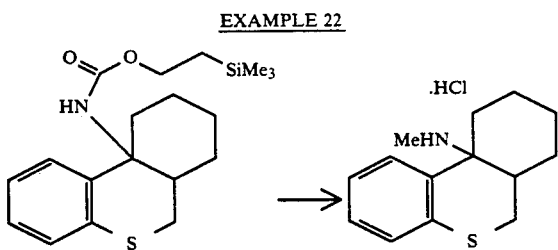

6,6a,7,8,9,10-Hexadydro-N-methyl-10aH-dibenzo[b,d]thio pyran-10a-amine monohydrochloride In a manner similar to that described in Example 4 the product of Example 21 (1.5 g) was reduced to give the title compound as a white solid (1.0 g, 91%), mp 211°-218° C.

EXAMPLE 23

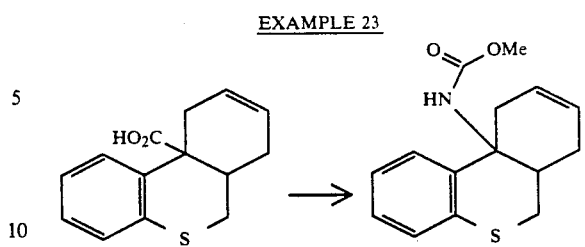

Methyl 6,6a,7,10-tetrahydro-10aH-dibenzo[b,d]thiopyran-10a-ylcarbamate

To a solution of the product from Example 19 (1.73 g) in dry toluene was added triphenylphosphoryl azide (2.03 g) and triethylamine (0.83 g). The solution was refluxed for 1 hour then cooled and washed with water and dried ($Na_2SO_4$) and evaporated in vacuo. The residue was taken up in methanol and refluxed for 14 hours then the solvent evaporated in vacuo to give the title compound as an off white solid (0.89 g). Chromatography of the residue afforded an addition lot of the title compound (0.4 g). Total recovered title compound was 1.47 g, mp 150.5°-151.5° C.

EXAMPLE 24

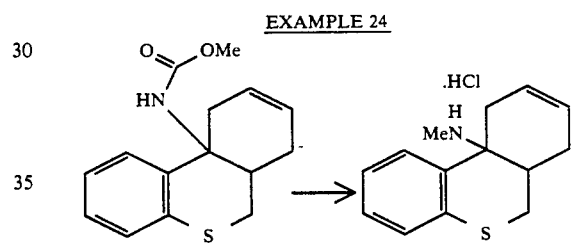

6,6a,7,10-Tetrahydro-N-methyl-10aH-dibenzo[b,d]thio pyran-10a-amine monohydrochloride In a manner similar to that described in Example 4, the product of Example 23 was reduced to give the title compound as a white solid (1.21 g, 72%).

EXAMPLE 25

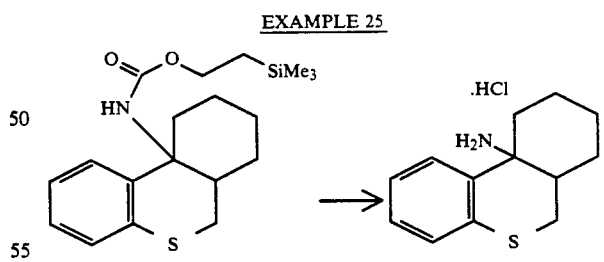

6,6a,7,8,9,10-Hexahydro-10aH-dibenzo[b,d]thiopyran-10a-amine monohydrochloride

To a solution of the product of Example 21 (1 g) in dry THF (10 ml) was added a solution of tetrabutylammonium fluoride (0.72 g) in THF (2.75 ml). The solution was refluxed for 15 minutes then cooled and diluted with ether. The ether solution acidified with 2N HCl and the aqueous layer was washed with ether. The aqueous phase was layered with fresh ether and basified with 12% sodium hydroxide. The aqueous layer was extracted with additional ether and the ether solutions were combined and washed twice with saturated brine and dried (Na2SO4). Evaporation of the ether solution afforded a clear oil which was taken up in dry ether and treated with isopropanolic HCl to afford the title compound as a white solid (0.6 g, 85%), mp 244°-246° C. (dec).

EXAMPLE 26

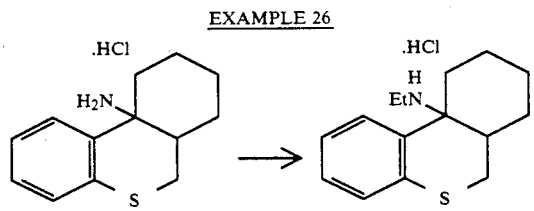

N-ethyl-6,6a,7,8,9,10-hexahydro-10aH-dibenzo[b,d]thiopyran-10a-amine monohydrochloride To a solution of the product of Example 25 (0.79 g) in dichloromethane (25 ml) was added triethylamine (0.75 g) and dimethylaminopyridine (0.05 g) followed by dropwise addition of acetic anhydride (0.63 g). After 1.45 hours the solution was diluted with dichloromethane and washed with dilute HCl, water and then dried (Na2SO4). Evaporation of the solvent in vacuo gave a white crystalline solid (1.04 g) which was dissolved in dry THF (12 ml) diluted with ether and reduced in a manner similar to that described in Example 4 to give the title compound as a white solid (0.74 g, 72%), mp 213°-216° C. (dec).

EXAMPLE 27

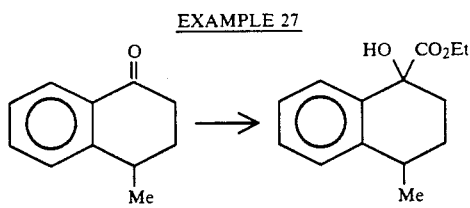

Ethyl 1,2,3,4-tetrahydro-1-hydroxy-4-methyl-1-naphthalenecarboxylate

A solution of 4-methyltetralone (29.1 g, 0.18 mole) in 100 ml of methylene chloride was treated with zinc iodide (0.1 g), and then trimethylsilylcyanide was added slowly via a dropping funnel. After stirring 15 hours, the solution was evaporated. The residual syrup was dissolved in 100 ml ethanol and added to a 5° C. saturated solution of HCl in 500 ml ethanol, with continued addition of HCl (g). The reaction mixture was warmed to ambient temperature overnight, was filtered, and the filtrate evaporated to give the amidate hydrochloride as a brown syrup. The syrup was dissolved in 100 ml 1N sulfuric acid and was covered with 200 ml diethyl ether and stirred vigorously for 3 days. The ether layer was separated and dried over sodium sulfate, filtered and evaporated. Chromatography on silica gel (1% ethyl acetate in heptane) gave the title compound in 50% overall yield.

EXAMPLE 28

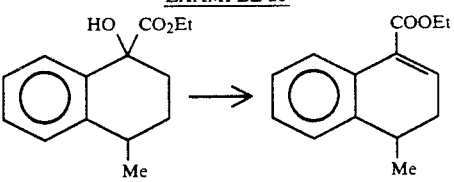

Ethyl 3,4-dihydro-4-methyl-1-naphthalenecarboxylate

The compound from Example 27 (42 g, 0.18 mole) and p-toluenesulfonic acid (6 g) were dissolved in 500 mL toluene and heated at reflux for 30 minutes with removal of water (Dean-Stark trap). The solution was cooled and washed with saturated sodium bicarbonate, dried over sodium sulfate, filtered and evaporated. The residual syrup was chromatographed on silica gel (0-3% ethyl acetate in heptane) to give the title compound in 93% yield.

EXAMPLE 29

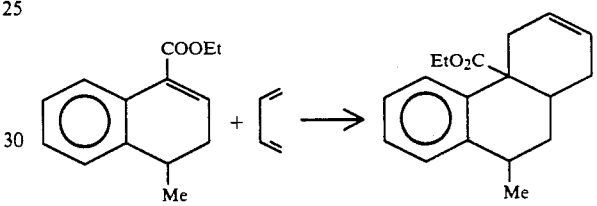

Ethyl 1,9,10,10a-Tetrahydro-4a(4H)-phenanthrene carboxylate

A Diels-Alder condensation between the vinyl ester (35 g, 0.16 mole) and 1,3-butadiene was carried out as before. The reaction mixture was concentrated, and the residue was distilled in vacuo to give a syrup (20 g). The syrup was refluxed in 1N KOH for 20 hours (no starting material left by GC), cooled and then extracted with diethyl ether. The ether solution was dried over sodium sulfate, filtered and evaporated to give the title compound (5.18 g, 13% yield). Starting material was recovered as the vinyl carboxylic acid (14 g, 46% recovery).

EXAMPLE 30

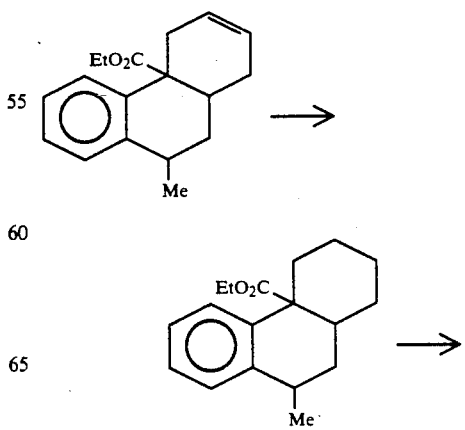

EXAMPLE 30

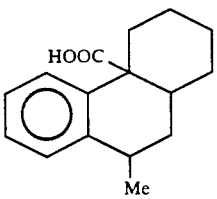

1,3,4,9,10,10a-Hexahydro-9-methyl-4a(2H)-phenanthrene carboxylic acid

The compound from Example 29 (5.08 g, 18.8 mmol) was hydrogenated according to the procedure described in Example 20. The filtrate was evaporated and the residue was purified on silica gel (1% ethyl acetate in heptane as eluant) to give the desired ester (4.75 g, 93% yield). A solution of the ester (2 g, 7.4 mmol) and potassium trimethylsilanolate (1.88 g, 14.7 mmol) in tetrahydrofuran was refluxed 24 hours. After removing the solvent the residue was dissolved in water and washed with methylene chloride. The aqueous phase was acidified with 2N HCl and extracted with methylene chloride. The organic solution was dried over sodium sulfate, filtered and evaporated to give the title compound as a white solid (1.6 g, 89% yield).

EXAMPLE 31

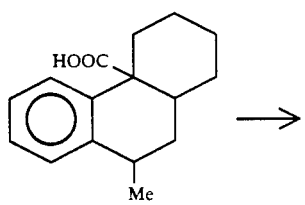

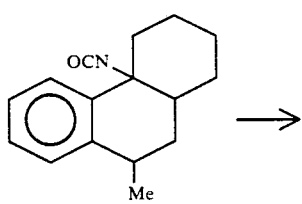

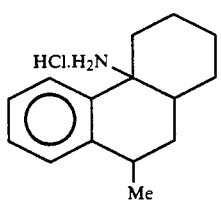

1,3,4,9,10,10a-Hexahydro-9-methyl-4a(2H)-phenanthrenanine monohydrochloride

A solution of the compound from Example 30 (1.5 g, 6.1 mmol), diphenylphosphorylazide (1.86 g, 6.7 mmol) and 1.5 ml triethylamine in 20 ml toluene was heated at 110° C. for 30 minutes under nitrogen. The reaction mixture was cooled and washed successively with water and saturated sodium chloride solution, dried over sodium sulfate, filtered and evaporated. The residue was chromatographed on silica gel (heptane as eluant) to give the isocyanate as a clear syrup. The isocyanate (0.7 g, 2.8 mmol) was dissolved in 15 ml benzene and then treated with a 50% aqueous potassium hydroxide solution (10 g). (Method of Example 2) After stirring vigorously overnight, the phases were separated and the aqueous phase was acidified with 2N HCl and washed with ether. The aqueous phase was basified with 1N NaOH and extracted with methylene chloride. The organic layer was dried and evaporated to give the amine as an oil (0.75 g). An ethereal solution of the amine was treated with isopropanolic HCl to give the title compound, mp 110° C.

Anal. (C$_{15}$H$_{21}$N.HCl).

Calc'd —C, 71.55; H, 8.81; N, 5.56;

Found—C, 70.82; H, 8.51; N, 5.05.

EXAMPLE 32

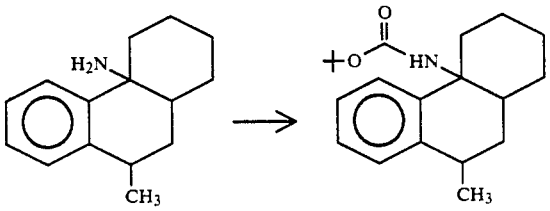

1,1-Dimethylethyl(1,3,4,9,10,10a-hexahydro-4a(2H)-phenanthrenyl)carbamate

A solution of the compound from Example 31 (0.75 g, 3.5 mmol) and di-tert-butyl dicarbonate (1.52 g, 6.98 mmol) in 25 ml methylene chloride and triethylamine was refluxed 3 hours. After evaporation of the solvent, the residue was chromatographed on silica gel (2% ethyl acetate in heptane as eluant) to give the title compound (0.53 g, 49%).

EXAMPLE 33

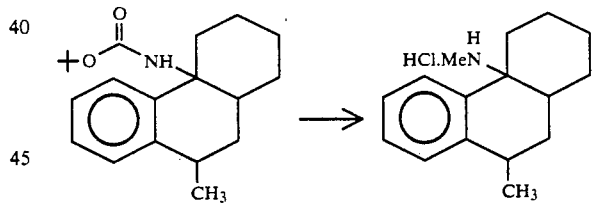

1,3,4,9,10,10a-Hexahydro-N,9-dimethyl-4a(2H)-phenanthrenamine monohydrochloride A solution of the compound from Example 32 (0.5 g, 1.58 mmol) in 5 ml diethyl ether was added to a suspension of lithium aluminum hydride in 10 ml diethyl ether cooled in an ice bath. (Method of Example 4) After stirring overnight the reaction mixture was quenched consecutively with 0.5 ml water, 0.4 ml 12.5% sodium hydroxide solution, and 1 ml water. The white precipitate was removed by filtration and washed with ether. The filtrate was extracted with 2N HCl, and the aqueous phase was basified and extracted with diethyl ether. After drying over sodium sulfate, the ether solution was treated with a solution of HCl in isopropyl alcohol to give the title compound as a white precipitate (0.17 g, 42%), mp 235°-237° C.

Anal. (C$_{16}$H$_{23}$N.HCl).

Calc'd—C, 72.29; H, 9.10; N, 5.27; Cl, 13.34;

Found—C, 71.85; H, 9.23; N, 5.00; Cl, 13.18.

EXAMPLE 34

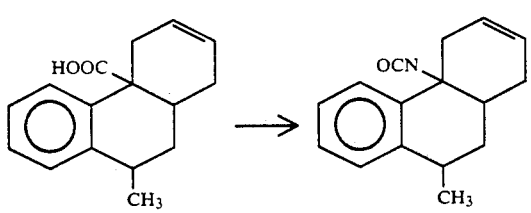

1,4,4a,9,10,10a-Hexahydro-4a-isocyanato-9-methyl-phenanthrene

The unsaturated carboxylic acid (1.5 g, 6.2 mmol) derived from hydrolysis of the product from Example 29 was converted to the isocyanate with diphenylphosphorylazide (1.87 g, 6.8 mmol) according to the method used in Example 31. Purification by silica gel chromatography gave the title compound as a clear oil (1.1 g, 74%).

EXAMPLE 35

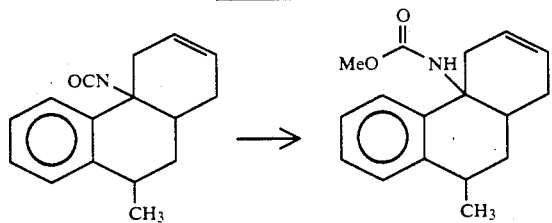

Methyl (1,9,10,10a-tetrahydro-9-methyl-4a(4H)-phenanthrenyl)carbamate

A solution of the compound of Example 34 (1.1 g, 4.6 mmol) in 20 ml methanol was refluxed for 24 hours. Evaporation gave the title compound (1.2 g, 96% yield).

EXAMPLE 36

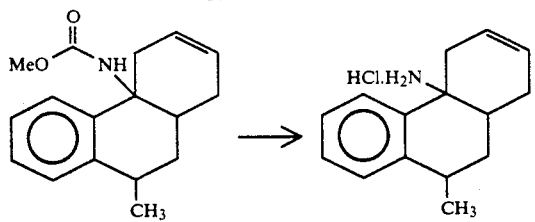

1,9,10,10a-Tetrahydro-9-methyl-4a(4H)-phenanthrenamine monohydrochloride

A solution of the compound of Example 35 (0.5 g, 1.85 mmol) and potassium trimethylsilanolate (0.47 g, 3.69 mmol) in 20 ml THF was refluxed overnight. The reaction was worked up as previously described, and the ethereal solution of the free amine was treated with isopropanolic HCl to give the title compound (0.25 g, 54%), mp 234°–236° C.

Anal. ($C_{15}H_{19}N \cdot HCl$).

Calc'd—C, 72.13; H, 8.07; N, 5.61;
Found—C, 71.95; H, 7.77; N, 5.27.

EXAMPLE 37

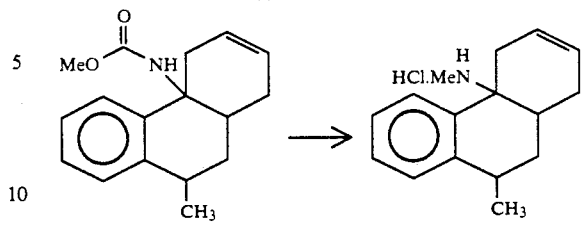

1,9,10,10a-Tetrahydro-N,9-dimethyl-4a(4H)-phenanthrenamine monohydrochloride A solution of the compound from Example 36 (0.65 g, 2.4 mmol) was reduced in a suspension of lithium aluminum hydride in ether as described in Example 33. A solution of the free amine in diethyl ether was treated with isopropanolic HCl to give the title compound (0.51 g, 81%), mp 248°–249° C.

Anal. ($C_{16}H_{21}N \cdot HCl$).

Calc'd—C, 72.85; H, 8.41; N, 5.31;
Found—C, 72.67; H, 8.49; N, 5.01.

EXAMPLE 38

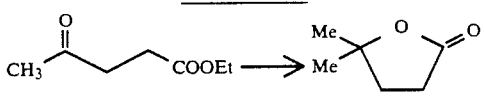

4,5-Dihydro-5,5-dimethyl-2(3H)-furanone

A solution of ethyl levulinate (130.2 g, 0.9 mole) in 400 ml ether and 500 ml benzene was cooled in an ice bath and treated with the slow addition of methylmagnesium iodide (1 mole in 500 ml ether). The ether was removed by distillation, and the remaining solution was refluxed for 3 hours. After cooling the reaction mixture was quenched with 1N sulfuric acid. The aqueous phase was washed with diethyl ether, and then the combined organic solutions were treated with aqueous potassium hydroxide (40 g in 200 ml water) and stirred for 1 hour. The aqueous layer was acidified with 50% sulfuric acid and extracted with ether. The ether layer was dried over sodium sulfate, filtered and evaporated to a brown syrup, which was distilled to give the title compound (50 g, 49%).

EXAMPLE 39

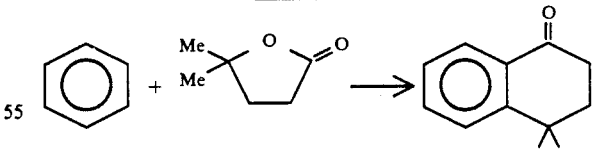

3,4-Dihydro-4,4-dimethyl-1(2H)-naphthalenone

A solution of aluminum chloride (150 g) in 230 ml benzene was cooled in an ice bath and treated via a dropping funnel with a solution of the compound from Example 38 (40 g, 0.35 mole) in 70 ml benzene. After addition was completed, the reaction mixture was refluxed for 3 hours, then cooled and added slowly to conc. HCl in ice. The organic layer was separated, combined with an ether wash of the aqueous phase, and

EXAMPLE 40

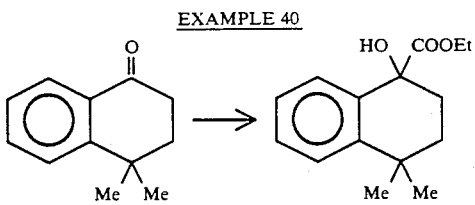

Ethyl 1,2,3,4-tetrahydro-1-hydroxy-4,4-dimethyl-1-naphthalenecarboxylate

A solution of the compound from Example 39 (39.5 g, 0.227 mole) in 50 ml methylene chloride was treated with trimethylsilylcyanide (25 g, 0.25 mole) and zinc iodide (50 mg) as before to give the protected cyanohydrin. Without further purification a solution of the cyanohydrin in 100 ml of ethanol was added to a cold solution of saturated hydrochloric acid in 500 ml ethanol. After standing overnight, the ethanol was evaporated and the syrup was dissolved in ether and stirred vigorously with 300 ml 1N sulfuric acid for 48 hours. Workup as before and chromatography on silica gel gave the title compound (20 g, 35%).

EXAMPLE 41

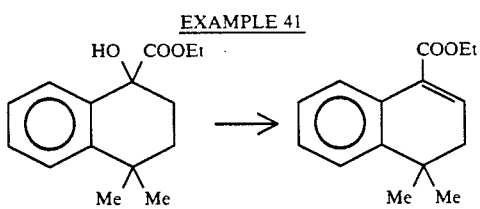

Ethyl 3,4-dihydro-4,4-dimethyl-1-naphthalenecarboxylate

A solution of the compound from Example 40 (20 g, 80 mmol) and tosic acid (3 g) in 300 ml toluene was refluxed for 45 minutes. After workup and silica gel chromatography, the title compound (15.6 g, 84%) was obtained.

EXAMPLE 42

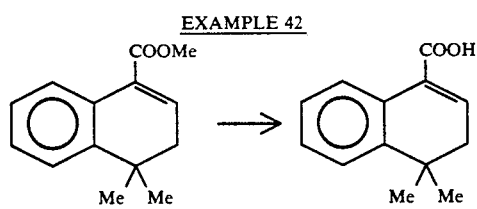

3,4-Dihydro-4,4-dimethyl-1-naphthalene-carboxylic acid

A solution of the compound from Example 41 (15.5 g, 71.7 mmol) and potassium trimethylsilanolate (17.4 g) in 100 ml of THF was refluxed for 24 hours. After workup the title compound (8.7 g, 52%) was obtained as a white solid.

EXAMPLE 43

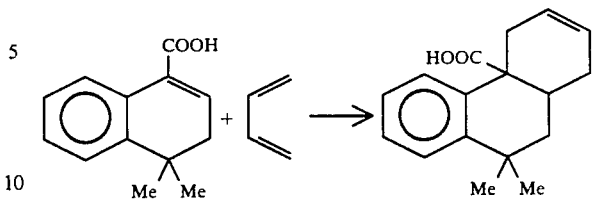

1,9,10,10a-Tetrahydro-9,9-dimethyl-4a(4H)-phenanthrenecarboxylic acid

The compound from Example 42 (8.5 g, 36.7 mmol) and butadiene were reacted in a Diels-Alder condensation as previously described to give after silica gel chromatography the title compound (3 g, 32% yield).

EXAMPLE 44

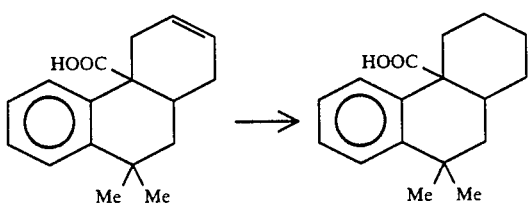

1,3,4,9,10,10a-Hexahydro-9,9-dimethyl-4a(2H)-phenanthrenecarboxylic acid

The compound from Example 45 (1.5 g, 5.86 mmol) was reduced with hydrogen over Pd/C as described in Example 20 to give the title compound (0.63 g, 42%).

EXAMPLE 45

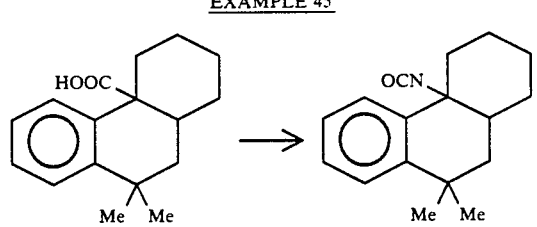

1,2,3,4,4a,9,10,10a-Octahydro-4a-isocyanato-9,9-dimethylphenanthrene

A solution of the compound from Example 44 (0.62 g, 2.4 mmol) and diphenylphosphorylazide (0.73 g, 2.64 mmol) in triethylamine (0.36 g) and 10 ml toluene was refluxed at 110° C. for 30 minutes. Workup and purification on silica gel gave the title compound (0.53 g, 86%).

EXAMPLE 46

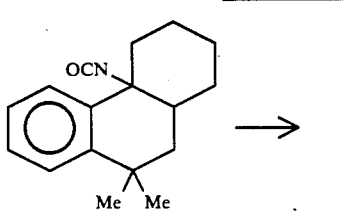

-continued
EXAMPLE 46

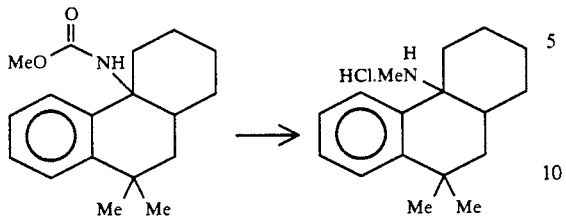

1,3,4,9,10,10a-Hexahydro-N,9,9-trimethyl-4a(2H)-phenanthrenamide monohydrochloride A solution of the compound from Example 45 (0.52 g, 2.04 mmol) in 10 ml methanol was refluxed overnight. Evaporation of the solvent gave the methyl carbamate. A solution of the methyl carbamate (0.2 g) in diethyl ether was added to a slurry of lithium aluminum hydride (0.5 g) and stirred overnight. Following workup as described in Example 33, an ethereal solution of the free amine was treated with isopropanolic HCl to give the title compound (0.18 g, 33%), mp 258°–259° C.

Anal. ($C_{17}H_{25}N.HCl$).
Calc'd—C, 72.96; H, 9.36; N, 5.01;
Found—C, 72.42; H, 9.56; N, 4.77.

EXAMPLE 47

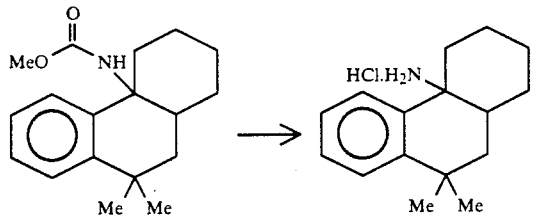

1,3,4,9,10,10a-Hexahydro-9,9-dimethyl-4a(2H)-phenanthrenamine monohydrochloride

A solution of the methyl carbamate (0.25 g, 0.87 mmol) obtained by the method described in Example 46 and potassium trimethylsilanolate (0.34 g, 2.6 mmol) in 15 ml THF was refluxed for 24 hours. Workup followed by treatment with isopropanolic HCl gave the title compound (0.075 g, 31%), mp 250°–252° C.

Anal. ($C_{16}H_{23}N.HCl$).
Calc'd—C, 72.29; H, 9.10; N, 5.27;
Found—C, 71.39; H, 8.07; N, 4.89.

EXAMPLE 48

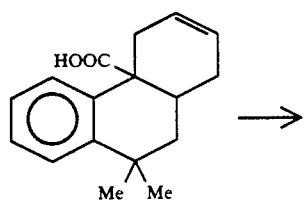

-continued
EXAMPLE 48

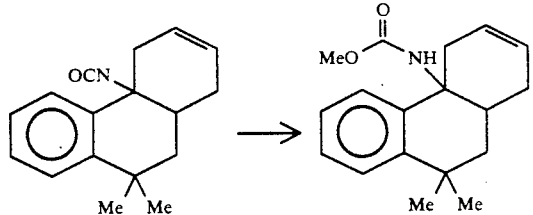

Methyl(1,9,10,10a-tetrahydro-9,9-dimethyl-4a(4H)-phenanthrenyl]carbamate

A solution of the compound from Example 43 (1.5 g, 5.86 mmol) and diphenylphosphorylazide in triethylamine (0.9 g) and 20 ml toluene was heated at 110° C. for 30 minutes. Workup and silica gel chromatography gave the isocyanate. A solution of the isocyanate (0.5 g) in 20 ml methanol was refluxed for 24 hours. Evaporation and purification on silica gel gave the title compound (0.15 g, 8%).

EXAMPLE 49

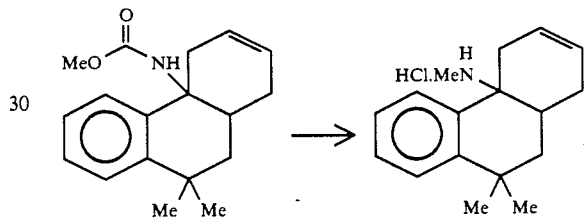

1,9,10,10a-Tetrahydro-9,9-dimethyl-4a(4H)-phenanthren amine monohydrochloride

A solution of the compound from Example 48 (0.15 g, 0.53 mmol) in 5 ml ether was added to a slurry of lithium aluminum hydride (0.5 g) in 5 ml ether and stirred overnight. Workup and treatment with isopropanolic HCl gave the title compound (0.075 g, 51%), mp 256°–258° C.

Anal. ($C_{17}H_{23}N.HCl$).
Calc'd—C, 73.49; H, 8.71; N, 5.04;
Found—C, 71.76; H, 8.75; N, 4.69.

EXAMPLE 50

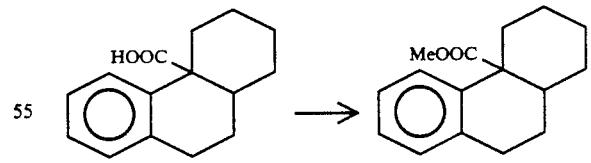

Methyl 1,3,4,9,10,10a-hexahydro-4a(2H)-phenanthrene carboxylate

A solution of cis-1,9,10,10a-tetrahydro-4a(4H)-phenanthrenecarboxylic acid (25 g, 0.11 mole) and dimethylsulfate (11.4 ml, 0.12 mole) in 75 ml acetone was treated with potassium carbonate (20.7 g, 0.15 mole) and stirred overnight. An additional 5 ml dimethylsulfate was added and the reaction mixture was refluxed for 1 hour. After cooling the potassium carbonate was removed by filtration and the filtrate evaporated to give the title compound (27 g, quantitative).

EXAMPLE 51

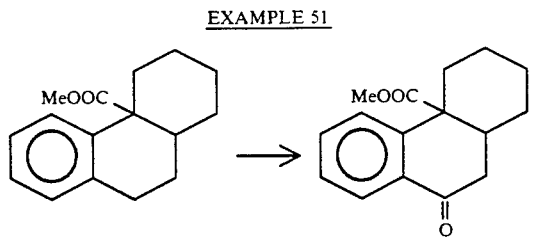

Methyl 1,3,4,9,10,10a-hexahydro-9-oxo-4a(2H)-phenanthrenecarboxylate

A solution of the compound from Example 50 (10 g, 41 mmol) in 500 ml acetic acid was cooled in an ice bath and treated dropwise with a solution of chromium trioxide in 100 ml acetic acid and 10 ml water. The reaction mixture was removed from the ice bath and stirred for 4 hours, and then poured into 1 L water and extracted with ether (2×1 L). The ether layer was washed with saturated sodium bicarbonate, dried over sodium sulfate, filtered and evaporated. The residue was purified over silica gel to give the title compound (5.5 g, 52%) and recovered starting material (4 g).

EXAMPLE 52

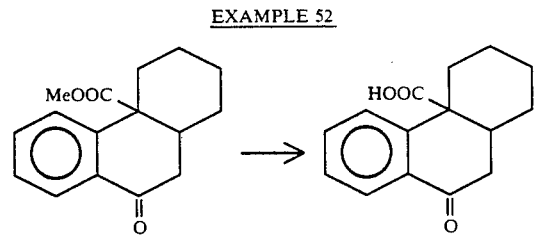

1,3,4,9,10,10a-Hexahydro-9-oxo-4a(2H)-phenanthrene carboxylic acid

A solution of the compound from Example 51 (1.5 g, 5.8 mmol) and potassium trimethylsilanolate (1.5 g, 11.6 mmol) in 25 ml THF was refluxed 60 hours. Workup as before and chromatography on silica gel gave the title compound (1.1 g, 78%).

EXAMPLE 53

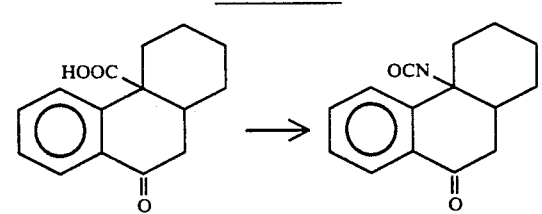

2,3,4,4a,10,10a-Hexahydro-4a-isocyanato-9(1H)-phenanthrenone

A solution of the compound from Example 52 (1 g, 4.1 mmol) and diphenylphosphorylazide (1.25 g, 4.5 mmol) in triethylamine (0.6 g) and 30 ml toluene was heated at 110° C. for 30 minutes. Workup and silica gel chromatography gave the title compound (0.65 g, 66%) as a yellow syrup.

EXAMPLE 54

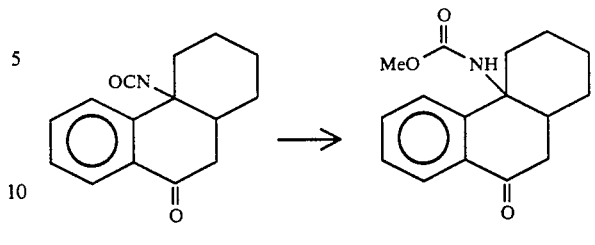

Methyl(1,3,4,9,10,10a-hexahydro-9-oxo-4a(2H)-phenanthrenyl) carbamate

A solution of the compound from Example 53 (0.44 g, 1.82 mmol) in 15 ml methanol was heated at reflux for 24 hours. Evaporation of the solvent and chromatography on silica gel gave the title compound (0.42 g, 90%).

EXAMPLE 55

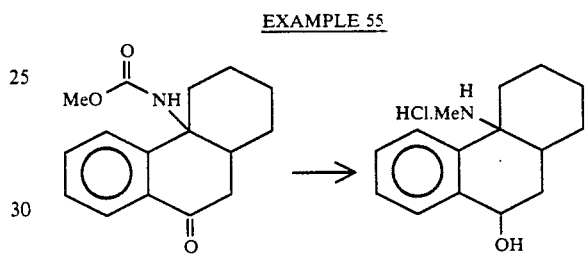

1,2,3,4,4a,9,10,10a-Octahydro-4a-(methylamino)-9-phenanthrenol monohydrochloride A solution of the compound from Example 54 (0.39 g, 1.52 mmol) in 10 ml diethyl ether and 5 ml tetrahydrofuran was added to a slurry of lithium aluminum hydride (0.5 g) in 10 ml diethyl ether and stirred overnight. Workup followed by treatment with isopropanolic HCl in ether gave the title compound (0.12 g, 29%), mp 201°–205° C.

Anal. ($C_{15}H_{21}NO \cdot HCl$).

Calc'd—C, 67.28; H, 8.28; N, 5.23;

Found—C, 67.18; H, 8.25; N, 4.84.

EXAMPLE 56

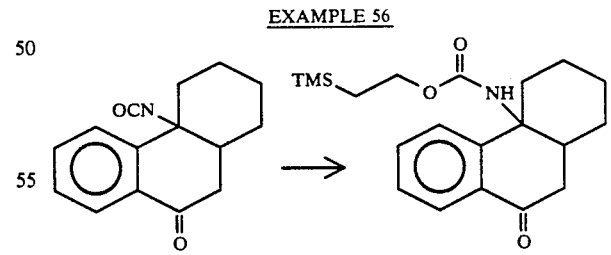

2-(Trimethylsilyl)ethyl (1,3,4,9,10,10a-hexahydro-9-oxo-4a(2H)-phenanthrenyl carbamate A solution of the compound from Example 54 (0.6 g, 2.5 mmol) and trimethylsilylethanol (10 ml) was heated at 60° C. overnight. The solvent was removed in vacuo and the residue purified over silica gel to give the title compound (0.54 g, 60% yield).

EXAMPLE 57

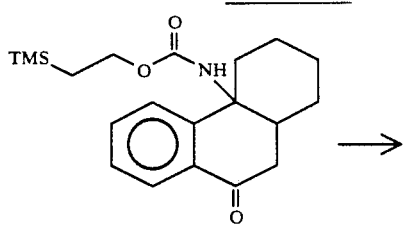

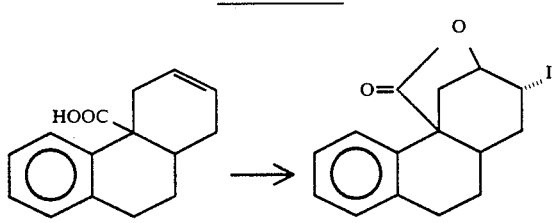

4a-Amino-2,3,4,4a,10,10a-hexahydro-9(1H)-phenanthrenone monohydrochloride

A solution of the compound from Example 56 (0.54 g, 1.5 mmol) in 20 ml THF was cooled in an ice bath and treated dropwise with tetra-N-butylammonium fluoride (1.88 ml, 1.88 mmol), and then refluxed for 30 minutes. Solvent was evaporated and the residue was dissolved in ether and treated with an acid/base workup and extracted from aqueous base with methylene chloride. The organic solution was dried over sodium sulfate, filtered and evaporated, and an ethereal solution of the residue was treated with isopropanolic HCl to give the title compound (0.14 g, 37%), mp 252°-254° C.
Anal. ($C_{14}H_{17}NO \cdot HCl$)
Calc'd—C, 66.79; H, 7.21; N, 5.56;
Found—C, 66.23; H, 7.67; N, 5.34.

EXAMPLE 58

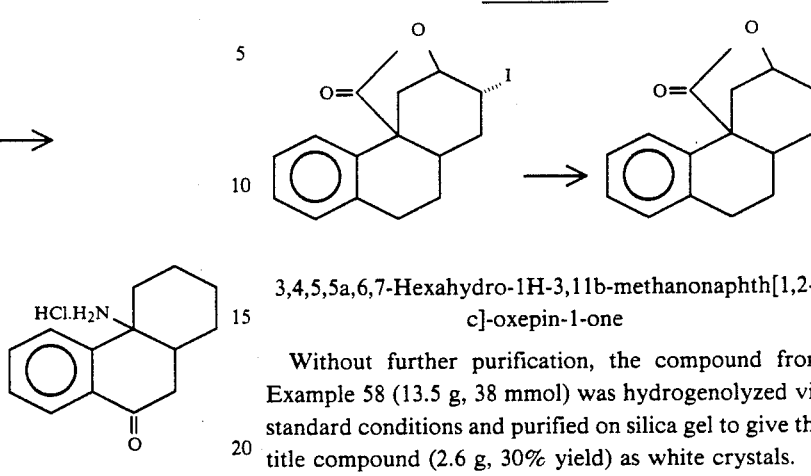

3,4,5,5a6,7-Hexahydro-4-iodo-1H-3,11b-methanonaphth-1,2-c]oxepin-1-one

A mixture of the compound from Example 6 (10 g, 44 mmol) and sodium bicarbonate (4 g, 48 mmol) in 150 ml water was heated on a steam bath until a solution was obtained. Potassium iodide (14.6 g, 88 mmol) and iodine (22.4 g, 88 mmol) were dissolved in 150 ml water and added to the reaction mixture via an addition funnel. The reaction mixture was placed in a separatory funnel and shaken with sodium bisulfite and then extracted with methylene chloride. The organic phase was dried over sodium sulfate, filtered and evaporated to give the title compound as a yellow solid (13.7 g, 88% yield).

EXAMPLE 59

3,4,5,5a,6,7-Hexahydro-1H-3,11b-methanonaphth[1,2-c]-oxepin-1-one

Without further purification, the compound from Example 58 (13.5 g, 38 mmol) was hydrogenolyzed via standard conditions and purified on silica gel to give the title compound (2.6 g, 30% yield) as white crystals.

EXAMPLE 60

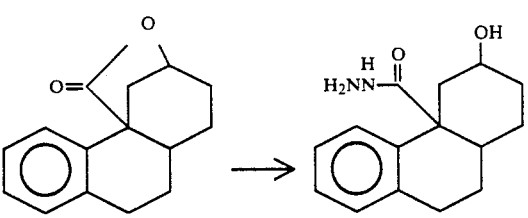

1,3,4,9,10,10a-Hexahydro-3-hydroxy-4a(2H)-phenanthrene-4a-carboxylic acid hydrazide A solution of the compound from Example 59 (6 g, 26 mmol) in 15 ml hydrazine, 15 ml acetic acid and 150 ml methanol was heated at reflux 56 hours. An additional 15 ml hydrazine was added and the mixture refluxed for 24 hours. The solvent was evaporated and the residue was dissolved in methylene chloride/water. The organic phase was dried over sodium sulfate, filtered and evaporated to give the title compound (6.3 g, 93%).

EXAMPLE 61

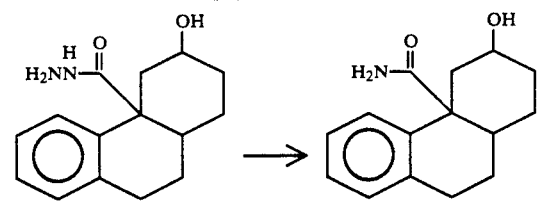

1,3,4,9,10,10a-Hexahydro-3-hydroxy-4a(2H)-phenanthrenecarboxamide

A solution of the compound from Example 60 (5 g, 19 mmol) and Raney nickel (10 g) in 200 ml ethanol was refluxed overnight. The catalyst was removed by filtration and the filtrate was evaporated to give a syrup, which was crystallized in heptane and toluene to give the pure title compound (3.4 g, 73% yield).

EXAMPLE 62

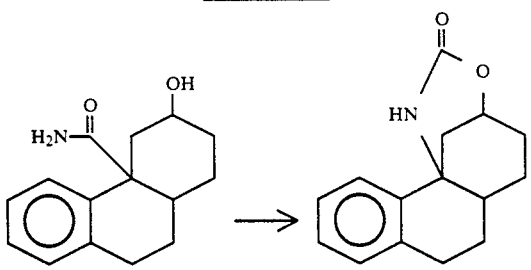

4,5,6,6a,7,8-Hexahydro-4,12b-methano-12bH-naphth-(1,2-d][1,3]oxazocin 2(1H)-one

A solution of the compound from Example 61 (2.44 g, 10 mmol) in 30 ml methanol was cooled in an ice bath, and treated with sodium metal (0.46 g, 20 mmol). After dissolution, the reaction mixture was treated with bromine (1.6 g, 10 mmol) in three portions. After stirring overnight at room temperature, the reaction mixture was treated with sodium bisulfite, stirred 10 minutes, and then extracted with methylene chloride. The organic layer was dried over sodium sulfate, filtered and evaporated. The residue was purified over silica gel to give the title compound (1.4 g, 58%) as a white solid.

EXAMPLE 63

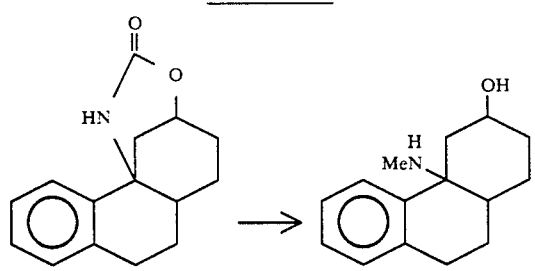

1,2,3,4,4a,9,10,10a-Octahydro-4a-(methylamino)-3-phenanthrenol

A solution of the compound from Example 62 (1.4 g, 5.75 mmol) in 20 ml THF was added to a slurry of lithium aluminum hydride (1 g) in 30 ml THF. After stirring overnight, additional lithium aluminum hydride was added (1 g) and stirring continued 3 hours. Workup afforded the title compound as a white solid (1.1 g, 83%), mp 141°–143° C.

Anal. ($C_{15}H_{21}$ NO.0.1$H_2O$)
Calc'd—C, 77.27; H, 9.17; N, 5.98;
Found—C, 77.06; H, 9.10; N, 5.81.

EXAMPLE 64

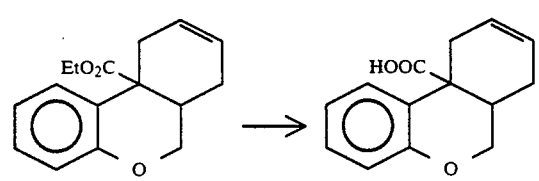

Ethyl 6,6a,7,10-tetrahydro-10aH-dibenzo[b,d]pyran-10a-carboxylic acid

A solution of the compound from Example 16 (4.4 g, 17 mmol) and potassium trimethylsilanolate (4.36 g, 34 mmol) in 50 ml THF was refluxed for 2 hours. The precipitate was collected by filtration, dissolved in water and acidified with 1N HCl. After further workup, the title compound was obtained as a white solid (3.9 g, 99%).

EXAMPLE 65

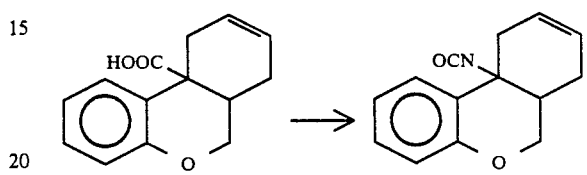

6a,7,8,9,10,10a-Hexahydro-10a-isocyanato-6H-dibenzo[b,d]pyran.

A solution of the compound from Example 64 (1.5 g, 6.51 mmol) and diphenylphosphorylazide (1.98 g, 7.2 mmol) in 2 ml triethylamine and 25 ml toluene was refluxed for 16 hours. Workup followed by silica gel chromatography gave the title compound as a clear oil (1.08 g, 73%).

EXAMPLE 66

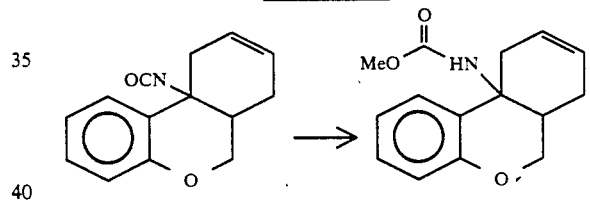

Methyl (6,6a,7,10-tetrahydro-10aH-dibenzo[b,d]pyran-10a-yl) carbamate

A solution of the compound from Example 65 (0.95 g, 4.18 mmol) in 70 ml methanol was refluxed overnight. Evaporation of the solvent gave the title compound as a white solid (1.1 g).

Anal ($C_{15}H_{17}NO_3$)
Calc'd—C, 69.48; H, 6.61; N, 5.40;
Found—C, 69.28; H, 6.68; N, 5.22.

EXAMPLE 67

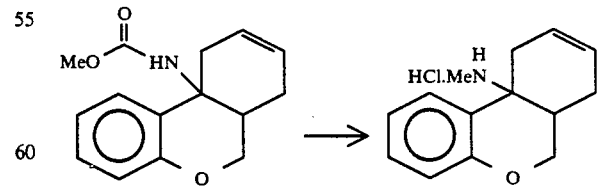

6,6a,7,8,9,10-Hexahydro-N-methyl-10aH-dibenzo[b,d]-pyran-10a-amine monohydrochloride A solution of the compound from Example 66 (0.5 g, 1.93 mmol) in 3 ml THF and 7 ml diethyl ether was added to a suspension of lithium aluminum hydride (0.5 g) in 20 ml diethyl ether and stirred for 2 hours. Workup and treatment of an ethereal solution of the amine with isopropanolic HCl gave the title compound (0.4 g, 88%), mp 210°–213° C.

Anal. (C$_{14}$H$_{17}$NO.HCl),
Calc'd—C, 66.79; H, 7.21; N, 5.56; Cl, 14.08;
Found—C, 66.81; H, 7.29; N, 5.46; Cl, 14.02.

EXAMPLE 68

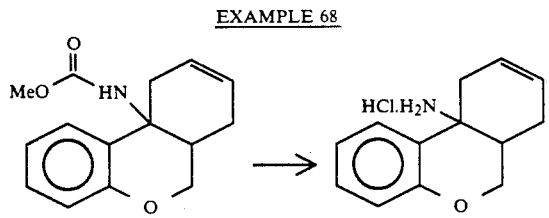

6,6a,7,10-Tetrahydro-10aH-dibenzo[b,d]pyran-10a-amine hydrochloride

A solution of the compound from Example 67 (0.51 g, 1.97 mmol) and potassium trimethylsilanolate in 50 ml THF was refluxed for 2 hours. The solution was diluted with diethyl ether and extracted with water. The aqueous phase was acidified with stirring to pH 1 with 1N HCl (gas evolution), and then basified and extracted with diethyl ether. An ethereal solution of the free base was treated with isopropanolic HCl to give the title compound (0.436 g), mp 215°–217° C.

Anal. (C$_{13}$H$_{15}$NO.HCl.0.2H$_2$O).
Calc'd—C, 64.70; H, 6.85; N, 5.80; Cl, 14.69;
Found—C, 64.91; H, 6.90; N, 5.80; Cl 14.56.

EXAMPLE 69

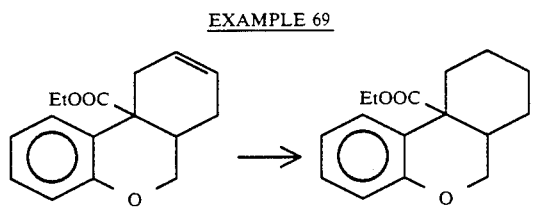

Ethyl 6,6a,7,8,9,10-hexahydro-10aH-dibenzo[b,d]pyran-10a-carboxylate

A mixture of the compound from Example 64 (4.8 g, 18.6 mmol) and 5% palladium on carbon in 100 ml ethanol was shaken under a hydrogen atmosphere for 19 hours. The title compound was obtained in quantitative yield.

EXAMPLE 70

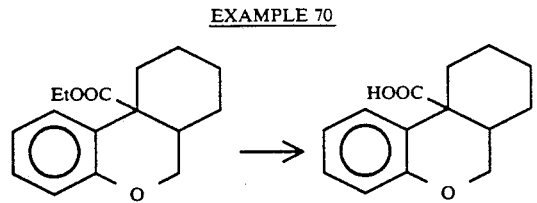

6,6a,7,8,9,10-Hexahydro-10aH-dibenz[b,d]pyran-10a-carboxylic acid

A solution of the compound from Example 69 (4.9 g, 18.6 mmol) and potassium trimethylsilanolate (4.5 g) in 75 ml THF was refluxed for 23 hours. Workup as previously described gave the title compound as a white solid (4.25 g).

EXAMPLE 71

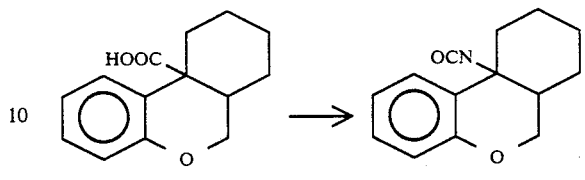

6a,7,8,9,10,10a-Hexahydro-10a-isocyanato-6H-dibenzo[b,d]pyran

A solution of the compound from Example 70 (1.0 g, 4.30 mmol) and diphenylphosphorylazide (1.3 g, 4.7 mmol) in 1.1 ml triethylamine and toluene was refluxed for 15 hours. Workup and silica gel chromatography gave the title compound (0.71 g) as a clear oil.

EXAMPLE 72

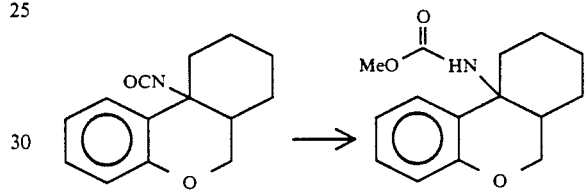

Methyl(6,6a,7,8,9,10-hexahydro-10aH-dibenzo[b,d]-pyran-10a-yl)carbamate

A solution of the product from Example 71 (0.66 g, 2.88 mmol) in 20 ml methanol was refluxed 18 hours. Evaporation and chromatography gave the title compound (0.75 g).

Anal. (C$_{15}$H$_{19}$NO$_3$).
Calc'd—C, 68.94; H, 7.33; N, 5.36;
Found—C, 68.77; H, 7.38; N, 5.22.

EXAMPLE 73

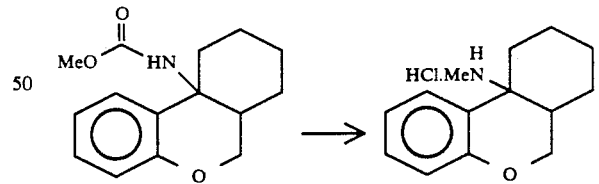

6,6a,7,8,9,10-Hexahydro-N-methyl-10aH-dibenzo[b,d]-pyran-10a-amine monohydrochloride A suspension of lithium aluminum hydride (0.5 g) in 10 ml diethyl ether was treated dropwise with a solution of the compound from Example 72 (0.34 g, 1.31 mmol) and stirred for 3 hours. Workup and treatment of the free methylamine with isopropanolic HCl gave the title compound (0.27 g), mp 219°–221° C.

Anal. (C$_{14}$H$_{19}$NO.HCl).
Calc'd—C, 66.26; H, 7.94; N, 5.52; Cl, 13.97;
Found—C, 66.43; H, 7.98; N, 5.33; Cl, 13.82.

EXAMPLE 74

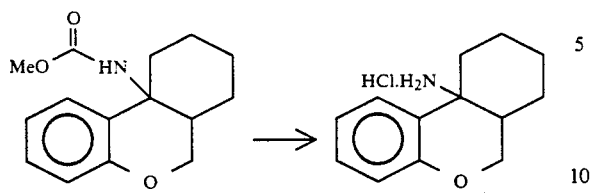

6,6a,7,8,9,10-Hexahydro-10aH-dibenzo[b,d]pyran-10a-amine monohydrochloride

A solution of the compound from Example 72 (0.3 g, 1.15 mmol) and potassium trimethylsilanolate (0.3 g, 2.34 mmol) was refluxed for 21 hours. Workup followed by treatment of the free amine with isopropanolic HCl gave the title compound (0.24 g), mp 230°–232° C.

Anal. ($C_{13}H_{17}NO·HCl·0.25H_2O$).

Calc'd—C, 63.92; H, 7.63; N, 5.73; Cl, 14.51;
Found—C, 63.59; H, 7.73; N, 5.54; Cl, 14.24.

EXAMPLE 75

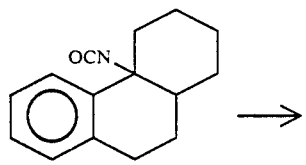

Preparation of the Menthol Carbamate

A solution of the compound from Example 1 (0.5 g, 2.2 mmol) and 1R,2S,5R-(−)-menthol (0.39 g, 2.5 mmol) in 10 ml toluene was refluxed for 12 hours. The solvent was evaporated and the residue was purified by silica gel chromatography to give a white solid (0.56 g).

Anal. ($C_{25}H_{37}NO_2$).

Calc'd—C, 78.28; H, 9.72; N, 3.65;
Found—C, 77.76; H, 9.54; N, 3.36.

EXAMPLE 76

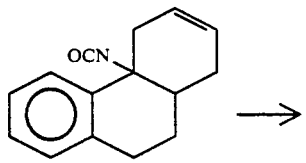

-continued
EXAMPLE 76

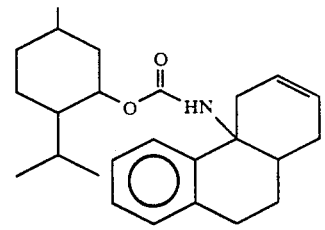

5-Methyl-2-(1-methylethyl)cyclohexyl (1,9,10,10a-tetrahydro-4a(2H)-phenanthrenyl carbamate Isomers A and B A solution of the compound from Example 7 (14 g, 62.1 mmol) and 1R,2S,5R-(−)-menthol (10.67 g, 68 mmol) in 200 ml toluene was refluxed 22 hours. Chromatography yielded unreacted isocyanate and a mixture of the isocyanate and product. These were recombined and treated with additional menthol (9 g) and 4-dimethylaminopyridine (0.12 g) in toluene and refluxed overnight. More menthol (1.13 g) was added and refluxing continued for 7 hours. The solvent was evaporated and the residue was purified on silica gel chromatography to give separation of the diastereomers A & B. Fraction A was rechromatographed to give pure title compound (4.87 g), mp 155°–158° C., $[\alpha]_D^{25} = +15.4°$. (C=1.025,CHCl$_3$).

Anal ($C_{25}H_{35}NO_2$).

Calc'd—C, 78.70; H, 9.25; N, 3.67;
Found—C, 78.67; H, 9.31; N, 3.38.

EXAMPLE 77

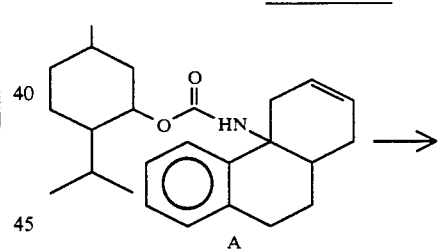

A

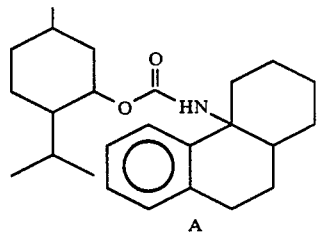

A

5-Methyl-2-(1-methylethyl)cyclohexyl (1,3,4,9,10,10a-hexahydro-4a(2H)-phenanthrenyl carbamate A solution of the unsaturated menthol carbamate A (4.87 g, 12.8 mmol) in 100 ml THF was hydrogenated under a hydrogen atmosphere (50.8 psi, 21°–23° C.) with 5% Pd/C (0.5 g) as catalyst for 24 hours. Filtration and evaporation gave as a white solid the title compound (4.21 g), mp 206°–210° C., $[\alpha]_D^{25} = -42.1°$ . (C=1.055, CHCl$_3$).

Anal. (C$_{25}$H$_{37}$NO$_2$).
Calc'd—C, 78.28; H, 9.72; N, 3.65;
Found—C, 78.39; H, 9.91; N, 3.31.

EXAMPLE 78

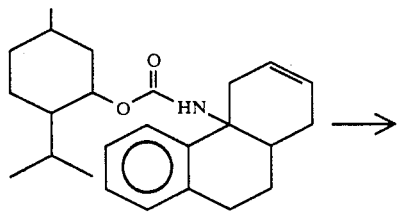

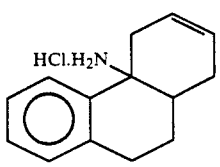

1,9,10,10a-Tetrahydro-4a(4H)-phenanthrenamine monohydrochloride

A solution of the unsaturated menthol carbamate from Example 76 (mixture of diastereomers, 0.83 g, 2.17 mmol) and potassium trimethylsilanolate in 30 ml THF was refluxed 20 hours. Standard aqueous acid/base workup followed by treatment of an ethereal solution of the amine with isopropanolic HCl gave the salt (0.22 g), mp 247°-248.5° C. Anal. C, H, N.

EXAMPLE 79

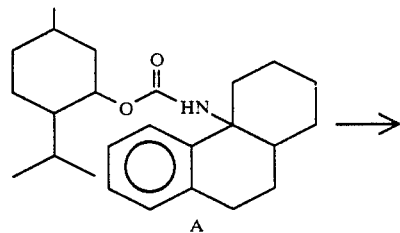

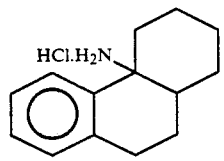

1,3,4,9,10,10a-Hexahydro-4a(2H)-phenanthrenamine monohydrochloride, Isomer A

A solution of the saturated menthol carbamate from Example 77 (A, 2.01 g, 5.24 mmol) and potassium trimethylsilanolate (1.35 g, 10.5 mmol) in 200 ml THF was refluxed under a nitrogen atmosphere for 22 hours. Standard workup followed by treatment of an ethereal solution of the primary amine with isopropanolic HCl and evaporation gave the salt (61% yield). [α]$_D^{25}$ = +34.2° (C=0.99, CHCl$_3$).
Anal. (C$_{14}$H$_{19}$N.HCl)
Calc'd—C, 70.72; H, 8.48; N, 5.89, Cl, 14.91;
Found—C, 70.59; H, 8.32; N, 5.22; Cl, 14.39.

EXAMPLE 80

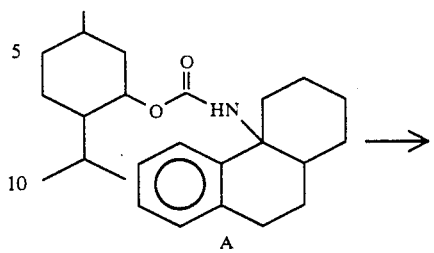

1,3,4,9,10-Hexahydro-N-methyl-4a(2H)-phenanthrenamine monohydrochloride, Isomer A A suspension of lithium aluminum hydride (0.25 g) in diethyl ether was treated with a suspension of the saturated menthol carbamate from Example 77 (A, 0.5 g, 1.3 mmol) and stirred for 5 hours. Standard workup followed by treatment of an ethereal solution of the amine with an HCl/ether solution gave the title compound as white needles (0.28 g), mp 235°-236.5° C. [α]$_D^{25}$= +14.7° (C=1.02 MeOH).
Anal. (C$_{15}$H$_{21}$N.HCl),
Calc'd—C, 71.55; H, 8.81; N, 5.56;
Found—C, 71.56; H, 8.80; N, 5.39.

EXAMPLE 81

Preparation of the Mosher Amide of the Primary Amine

A solution of R-(+)-α-methoxy-α-(trifluoromethyl)-phenylacetic acid (1 g, 4.27 mmol) and thionyl chloride (5 ml) was refluxed under a nitrogen atmosphere for 2 hours. After removal of the excess thionyl chloride by rotoevaporation, the residue was dissolved in 5 ml methylene chloride and treated with a solution of the primary amine obtained from Example 2 (0.9 g, 4.48 mmol) and triethylamine (1.5 ml) in 4 ml methylene chloride. An exothermic reaction resulted. Upon cooling, the reaction mixture was quenched with water, followed by a standard acid/base workup. Silica gel chromatography gave separation of the diastereomers (A and B). An HPLC analysis of enantiomeric purity of the primary amine has been developed using the Mosher Amide (silica gel column, 100:3 hexane:ethyl acetate).

EXAMPLE 82

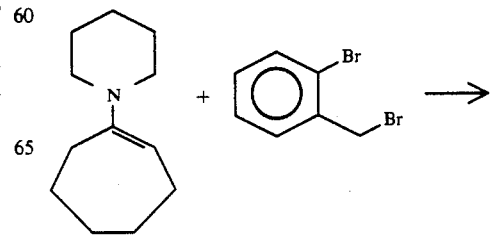

EXAMPLE 82

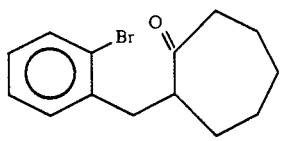

2-[(2-Bromophenyl)methyl]cycloheptanone

To a solution of cycloheptanone (56.1 g, 0.5 mol) in toluene (500 ml) was added morpholine (65.3 g, 0.75 mol) and tosic acid (100 mg). The reaction vessel was fitted with a Dean-Stark condenser and the reaction was refluxed for 24 hours. The toluene was removed in vacuo and the enamine was vacuum distilled. The enamine was collected as a pale yellow oil (46.5 g, 51%). To a solution of the enamine (10.0 g, 0.055 mol) in dioxane (50 ml) was added 2-bromobenzyl bromide and the reaction was refluxed overnight. Water (10 ml) was then added and the mixture was refluxed an additional 2 hours. The reaction was cooled and the solvent was removed in vacuo. The residue was partitioned between dichloromethane and 1N hydrochloric acid. The dichloromethane layer was washed with additional 1N hydrochloric acid (50 ml) and water (50 ml), dried (MgSO₄), filtered, and reduced in volume to yield a crude orange oil (15.9 g). The mixture was vacuum distilled to yield the title compound as a clear oil (8.5 g, 55%) that was a semisolid at 23° C.

EXAMPLE 83

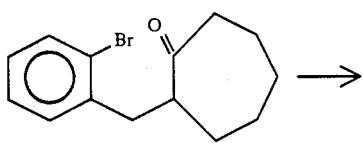

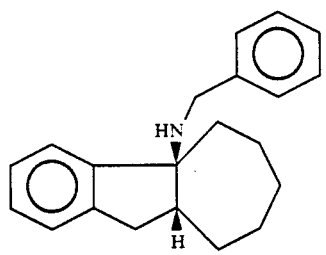

(±)-Cis-6,7,8,9,9a,10-hexahydro-N-(phenylmethyl)b-enz-[a]azul-en-4b(5H)-amine monohydrochloride To a solution of the ketone from Example 82 (8.75 g, 0.031 mol) in toluene (200 ml) was added benzyl amine (4.32 g, 0.04 mol) and tosic acid (100 mg). The reaction was refluxed for 24 hours and water was collected in a Dean-Stark condenser. The reaction was monitored by gas chromatography for completion. The reaction was cooled to 25° C., filtered and the solvent was evaporated in vacuo. The excess benzylamine was removed by heating the crude product at 75° C. under high vacuum. The imine was isolated as a yellow oil (11.4 g, 99%) which was used without additional purification. To a solution of the imine (8.94 g, 0.025 mol) in tetrahydrofuran at −78° C. was added t-butyllithium (1.7M in pentane) (14.7 ml, 0.025 mol). The reaction was stirred at −78° C. for 30 minutes, warmed to 25° C. and worked up immediately. The solvent was removed in vacuo and the crude residue partitioned between saturated ammonium chloride and dichloromethane. The dichloromethane layer was dried (MgSO₄), filtered and concentrated to yield a crude yellow oil. The oil was chromatographed on a silica gel column eluted initially with petroleum ether followed by ethyl acetate/petroleum ether (1:9). The product was eluted as a yellow oil (4.8 g, 66%), which was taken up in anhydrous ether and treated with isopropanolic HCl to afford the title compound as a white solid, mp 192°–194° C.

EXAMPLE 84

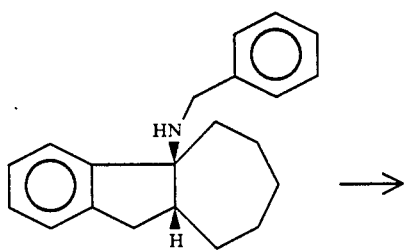

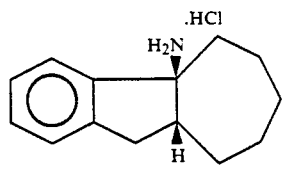

(±)-Cis-6,7,8,9,9a,10-hexahydrobenz[a]azulen-4b(5H)-amine monohydrochloride

To a solution of the benzylamine from Example 83 in methanol (50 ml) and tetrahydrofuran (50 ml) was added 0.5 g of 20% palladium on carbon. The reaction was hydrogenated for 18 minutes and stopped. The catalyst was removed by filtration and the solvent was concentrated under reduced pressure. The residue was partitioned between 0.1N hydrochloric acid and dichloromethane. The dichloromethane was dried (MgSO₄), filtered and concentrated in vacuo to yield a brown oil. The oil was slurried with ether and ethyl acetate and a white solid precipitated to afford the title compound (2.5 g, 54%), mp 224°–226° C.

EXAMPLE 85

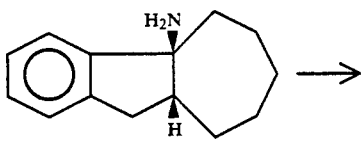

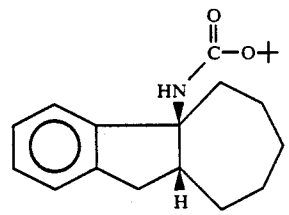

1,1-Dimethylethyl (±)-cis-(6,7,8,9,9a,10-hexhydrobenz[a]-azulen-4b(5H)-yl)carbamate To a solution of the free base of the amine described in Example 84 (0.48 mol, 2.4 mmol) in dichloromethane (20 ml) was added di-t-butyl dicarbonate (0.62 9, 3.6 mmol). The reaction was refluxed for 20 hours and additional carbonate (180 mg) was added and the reaction was refluxed another 4 hours. The reaction was cooled and the dichloromethane solution was washed with 5% sodium bicarbonate. The dichloromethane layer was separated, dried (MgSO4), filtered and concentrated in vacuo. The crude residue was chromatographed on a silica gel column eluted initially with petroleum ether with increasing amounts of ethyl acetate up to 20%. The title compound was isolated as a clear oil (0.65 g, 90%).

EXAMPLE 87A

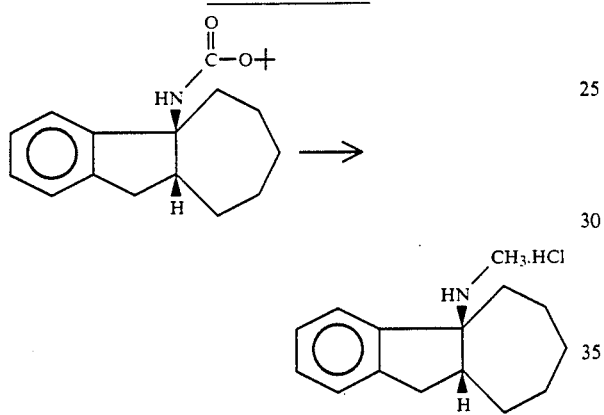

(±)-Cis-6,7,8,9,9a,10-hexahydrobenz[a]azulen-4b(5H)amine monohydrochloride

To a slurry of lithium aluminum hydride (0.91 g, 24 mmol) in ether (10 ml) was added an ether solution (5 ml) of the carbamate (0.72 g, 2.4 mmol) described in Example 85 over a 5 minute period. The reaction was stirred at 25° C. for 3 days. The reaction was quenched by adding water (0.9 ml), followed by sodium hydroxide (12.5% aqueous solution, 0.8 ml), followed by water (2.0 ml). The aluminum salts were slurried in additional ether and filtered. The ether solution was dried (MgSO4), filtered and concentrated in vacuo to yield the targeted methylamine as a clear oil. The oil was dissolved in ether and treated with isopropanolic hydrochloride to afford the title compound as a white solid (0.47 g, 78%) mp 207°-208° C.

EXAMPLE 87B

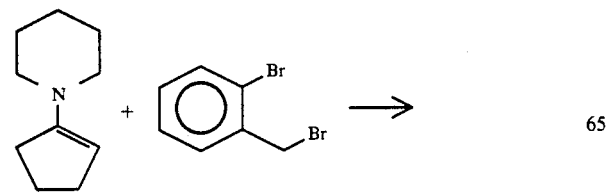

-continued
EXAMPLE 87B

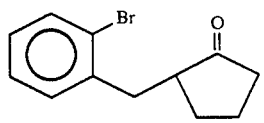

2-[(2-bromophenyl)methyl]cyclopentanone

In a manner similar to that described in Example 82, 1-pyrrolidino-1-cyclopentane (15.1 g, 0.11 mole) in dioxane (100 ml) was treated with 2-bromobenzyl bromide (30.0 g, 0.12 mol) to give the title compound as a clear oil (12.5 g, 45%).

EXAMPLE 88

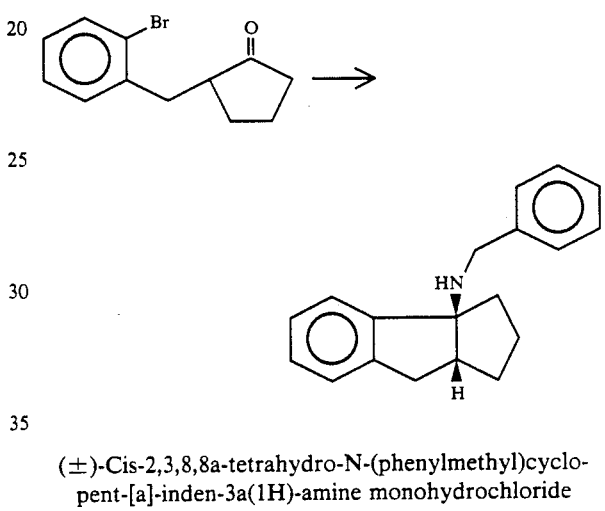

(±)-Cis-2,3,8,8a-tetrahydro-N-(phenylmethyl)cyclopent-[a]-inden-3a(1H)-amine monohydrochloride In a manner similar to that described in Example 83 the product of Example 87B (8.0 g, 32 mmol) in toluene (200 ml) was treated with benzylamine (4.5 g, 38 mmol) and tosic acid (75 mg) to produce the imine (10.55 g). To a solution of the imine (10.55 g, 31 mmol) in tetrahydrofuran (150 ml) was added n-BuLi (2.2M in hexane) (14.3 ml) to produce the free base of the amine as a yellow oil (3.49 g, 43%). A sample was converted to the title compound as a white solid, mp 266°-268° C.

EXAMPLE 89

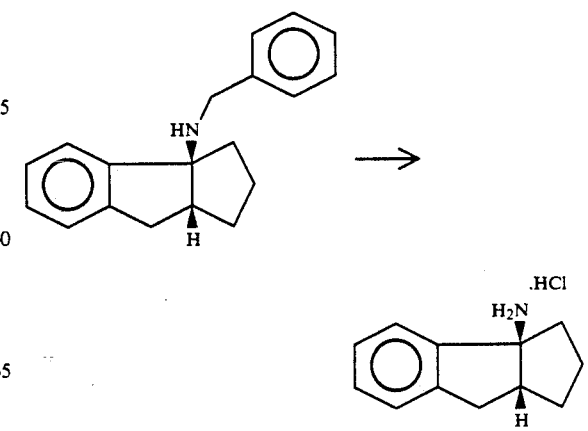

(±)-2,3,8,8a-Tetrahydrocyclopent[a]inden-3a(1H)-amine monohydrochloride

In a manner similar to that described in Example 84 the benzylamine product of Example 88 (2.67 g, 10 mmol) was reduced to give the title compound as a white solid (1.5 g, 71%), mp 270°–271° C.

EXAMPLE 90

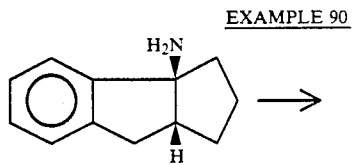

1,1-dimethylethyl (±)-cis-(2,3,8,8a-tetrahydrocyclopent[a]-inden-3a(1H)-yl)carbamate In a manner similar to that described in Example 85 the free amine of Example 89 (0.23 g, 1.3 mmol) was acylated to afford the title compound as a thick oil (0.36 g, >99%).

EXAMPLE 91

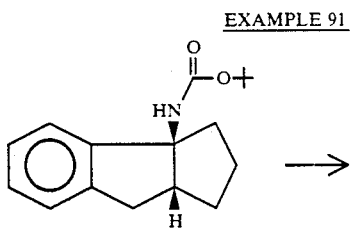

(±)-Cis-2,3,8,8a-tetrahydro-N-methylcyclopent[a]inden-3a(1H)-amine monohydrochloride In a manner similar to that described in Example 86 the carbamate product of Example 88 (0.38 g, 1.4 mmol) was reduced to give the title compound as a white solid (0.16 g, 51%), mp 202°–203° C.

EXAMPLE 92

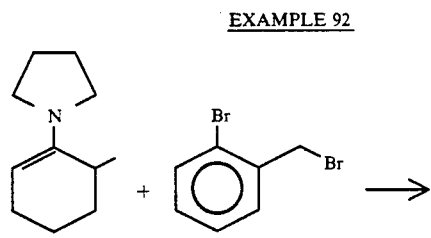

-continued
EXAMPLE 92

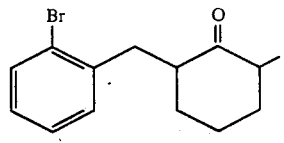

2-Methyl-6-(2-(bromophenyl)methyl)-cyclohexanone

A solution of orthobromobenzylbromide (17.0 g, 68 mmol) and 2-methyl-1-pyrrolidino-1-cyclohexene, (12.5 g, 75 mmol), (prepared by the method of G. Stork, et al, *J. Am. Chem. Soc.*, 85, 207 (1963)) in 100 ml dioxane was refluxed for 72 hours. Water (30 ml) was added and refluxing continued for 3 hours. The organics were extracted with ether, dried (MgSO$_4$), filtered, and evaporated in vacuo to give a pale oil. The oil was chromatographed to give the title compound as a colorless oil (15.7 g, 74%).

EXAMPLE 93

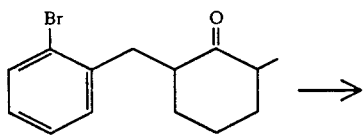

Cis-(±)-1,2,3,4,9,9a-hexahydro-4-methyl-N-phenylmethyl-4aH-fluorene-4a-amine To a solution of the compound from Example 92 (4.9 g, 18 mmol) in toluene (60 ml) was added benzylamine (2.5 ml, 0.023 mol) and p-toluenesulfonic acid (50 mg). The mixture was heated to reflux for 48 hours removing the water formed using a Dean-Stark apparatus. The solution was concentrated in vacuo to give a thick pale oil. The pale oil was dissoled in tetrahydrofuran (75 ml) and cooled to −78° C. A solution of t-butyllithium (1.7M in pentane), (15.4 ml, 0.026 mol) was added dropwise. The temperature of the deep red solution was maintained at −78° C. for 2 hours then allowed to warm to 0° C. and stirred for 24 hours. The reaction was partitioned between ether (500 ml) and water. The ether layer was dried (MgSO$_4$), evaporated in vacuo, then chromatographed to give the title compound as a colorless oil (3.9 g, 60%).

EXAMPLE 94

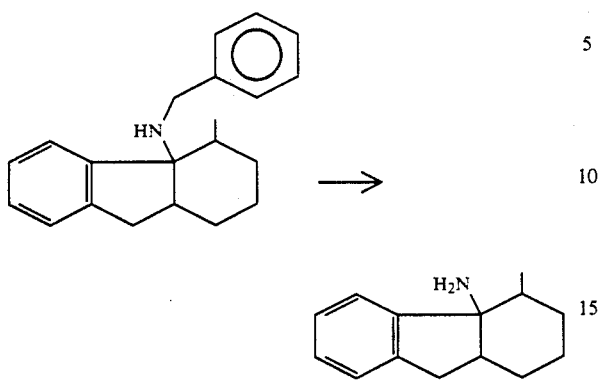

Cis-[±]-1,2,3,4,9,9a-hexahydro-4-methyl-4aH-fluoren-4a-amine monohydrochloride

Using the method of the Example 84, the compound of Example 93 was transformed into the title compound. The compound was chromatographed to give a colorless oil (2.9 g, 64%). To the oil (1.0 g) in fresh ether was added an isopropanolic HCl solution. The white solid was filtered and dried under vacuo to yield the title compound, (1.0 g, 87%), mp 270° C.

EXAMPLE 95

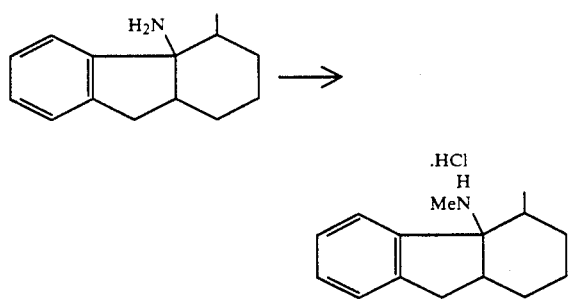

Cis-(±)-1,2,3,4,9,9a-hexahydro-N,4-dimethyl-4aH-fluoren-4a-amine monohydrochloride To a solution of the free base of the compound prepared in Example 94 (0.77 g, 4 mmol) in dichloromethane (10 ml) was added di-tert-butyl-dicarbonate (1.33 g, 8 mmol). The mixture was heated to reflux for 24 hours. The solution was evaporated in vacuo to yield a brown oil which was chromatographed to give a pale oil (0.96 g, 83%). The oil (0.93 g) was dissolved in diethyl ether (5.0 ml) and added to a solution of lithium aluminum hydride (1.7 g, 30 mmol) in diethyl ether (50 ml). The mixture was stirred for 24 hours then poured onto a saturated aqueous potassium sodium tartarate solution. The solution was layered with ethyl acetate. The ethyl acetate layer was dried (MgSO$_4$), concentrated in vacuo, then chromatographed to yield a colorless oil (0.62 g, 93%). The oil (0.49 g) was taken up with ether and treated with isopropanolic HCl. The white solid was dried in vacuo to give the title compound, (0.47 g, 82%), mp 242° C.

EXAMPLE 96

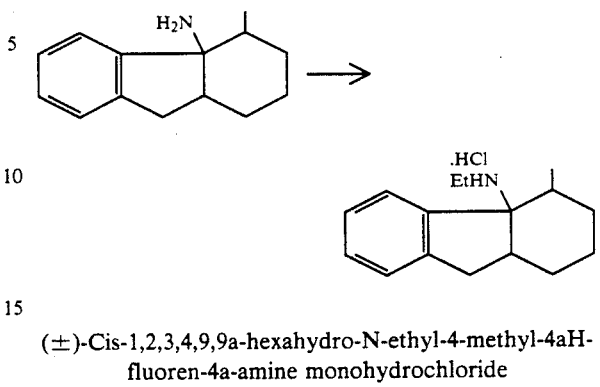

(±)-Cis-1,2,3,4,9,9a-hexahydro-N-ethyl-4-methyl-4aH-fluoren-4a-amine monohydrochloride To a solution of the free base of the compound prepared in Example 94 (1.1 g, 5.5 mmol) in dichloromethane (15 ml) was added triethylamine (0.57 ml, 6.0 mmol), acetic anhydride (2.3 ml, 16 mmol), and dimethylformamide (0.5 ml). The mixture was heated to reflux for 24 hours. The solution was diluted with dichloromethane (200 ml) and washed with water. The dichloromethane layer was dried (MgSO$_4$), concentrated in vacuo, then chromatographed to give a colorless oil (1.0 g, 75%). The oil was dissolved in tetrahydrofuran (10 ml) and added to a solution of lithium aluminum hydride (1.43 g, 38 mmol) in tetrahydrofuran (10 ml). After stirring 24 hours the solution was poured onto a saturated aqueous potassium sodium tartrate solution. The solution was layered with ethyl acetate. The ethyl acetate layer was dried (MgSO$_4$), concentrated in vacuo, then chromatographed to give a colorless oil (0.74 g, 85%). The oil was taken up with ether and treated with isopropanolic HCl. The white solid obtained was dried in vacuo to give the title compound, (0.59 g, 69%), mp 204° C.

EXAMPLE 97

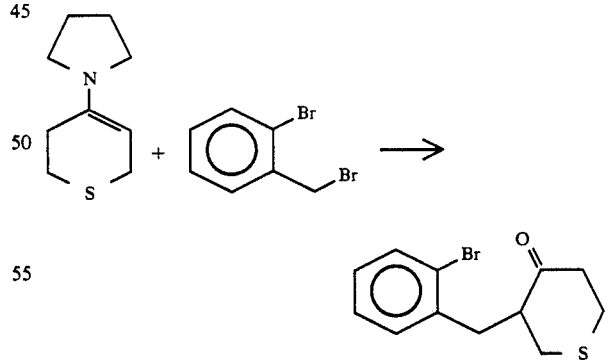

3-[(2-Bromophenyl)methyl]tetrahydro-4H-thiopyran-4-one

In a manner similar to that described in Example 82, 1-(3,6-dihydro-2H-thiopyran-4-yl)-pyrrolidine (25.0 g, 0.15 mole) or as is in dioxane (100 ml) was treated with 2-bromobenzyl bromide (40.0 g, 0.16 mol) to give the title compound as a clear oil (16.3 g, 15%).

EXAMPLE 98

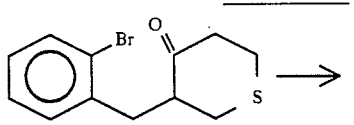

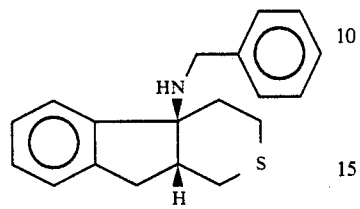

(±)-Cis-3,4,9,9a-tetrahydro-N-(phenylmethyl)-
indeno[2,1-c]-thiopyran-4a(1H)-amine
monohydrochloride In a manner similar to that described in Example 83 the product of Example 97 (6.70 g, 23 mmol) in toluene (120 ml) was treated with benzylamine (2.7 g, 25 mmol) and tosic acid (75 mg) to produce the imine (8.25 g). To a solution of the imine (8.25 g, 22 mmol) in tetrahydrofuran (50 ml) was added t-BuLi (1.7M in pentane) (14.1 ml, 24 mmol) to produce the free base of the amine as an oil (3.2 g, 49%). A sample was converted to give the title compound as a white solid, mp 214°–215° C.

EXAMPLE 99

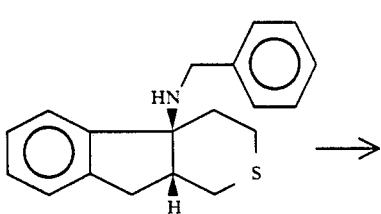

(±)-Cis-3,4,9,9a-tetrahydroindeno[2,1-c]thiopyran-
4a(1H)-amine

To a solution of the benzylamine (1.0 g, 3.4 mmol) from Example 98 in acetonitrile/water (7:3) is added 9,10-dicyanoanthracene. The reaction is irradiated as described in *Tetrahedron Letters* 29, 4157 (1988). The reaction yields the primary amine which is converted to the title compound.

EXAMPLE 100

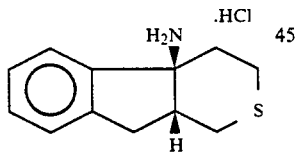

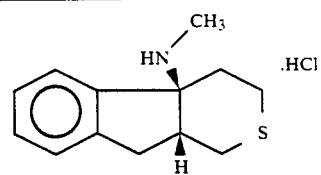

(±)-Cis-3,4,9,9a-tetrahydro-N-methyl-indeno[2,1-c]-
thiopyran-4a(1H)-amine monohydrochloride To a solution of the ketone (1.0 g, 3.5 mmol) from Example 97 in benzene (10 ml) is added an excess of methyl amine in a sealed tube and reacted as described in *J. Org. Chem.*, 28, 1112 (1963). The benzene is removed in vacuo and the imine is treated with t-BuLi as described in Example 83. The product is purified by column chromatography to yield the methyl amine as a oil, which was converted to the title compound with isopropanolic hydrogen chloride.

EXAMPLE 101

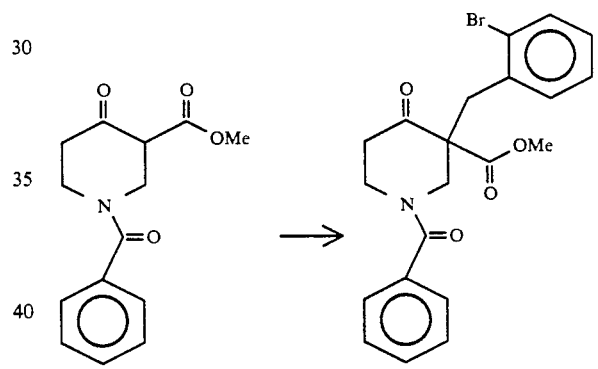

Methyl
1-(benzoyl)-3-(2-bromophenyl)methyl]-4-oxo-3-
piperidinecarboxylic acid

To a solution of potassium t-butoxide (16.8 g, 0.15 mol) in t-butanol (300 ml) was added methyl 1-benzoyl-4-oxo-3-piperidinecarboxylic acid (36.1 g, 0.146 mol) according to the method of G. Stork, *J. Am. Chem. Soc.* 68, 1053 (1946). The mixture was stirred 1 hour and 2-bromobenzyl bromide was added dropwise in a solution of t-butanol. The reaction was heated to reflux for 2 days, cooled and filtered. The salts were washed with ether and the organic filtrate was washed with 5% hydrochloric acid (100 ml), saturated sodium bicarbonate (100 ml), water (100 ml) and saturated sodium chloride (100 ml). The organic layer was dried (MgSO$_4$), filtered, and concentrated to yield a crude oil. The material was recrystallized from isopropyl ether to yield a pale yellow solid (23.4 g, 37%) An additional recrystallization produced the title compound a white solid, mp 105°–107° C.

EXAMPLE 102

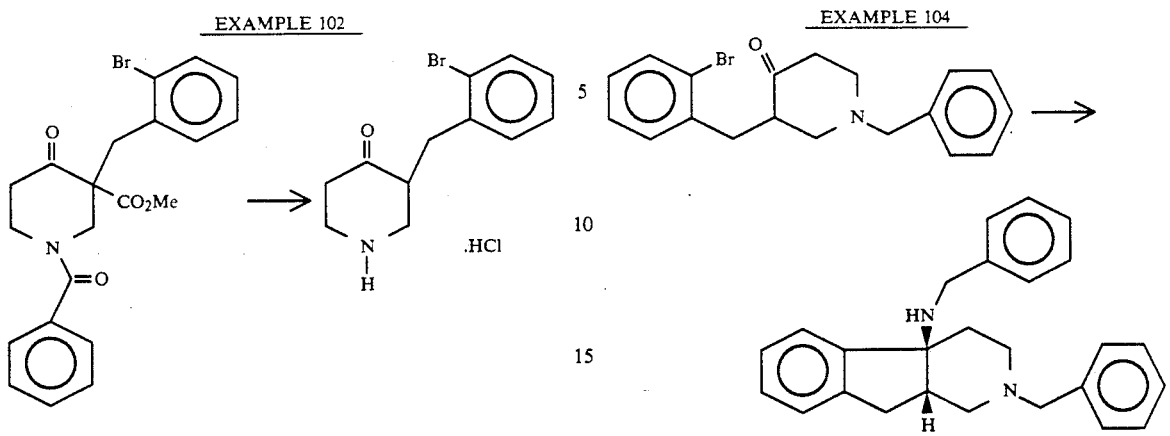

3-[(2-Bromophenyl)methyl]-4-piperidinone monohydrochloride

The ketoester (18.5 g, 0.043 mol) from Example 101 was suspended in 6N hydrochloric acid and refluxed for 18 hours. The reaction was cooled and the benzoic acid was filtered and washed with water.

The filtrate was washed with ether (2×75 ml) and the aqueous layer was concentrated under reduced pressure. The crude residue was crystallized from ethanol and ethyl ether to produce the title compound (10.1 g, 77%) as a white solid, mp 198°–200° C.

EXAMPLE 103

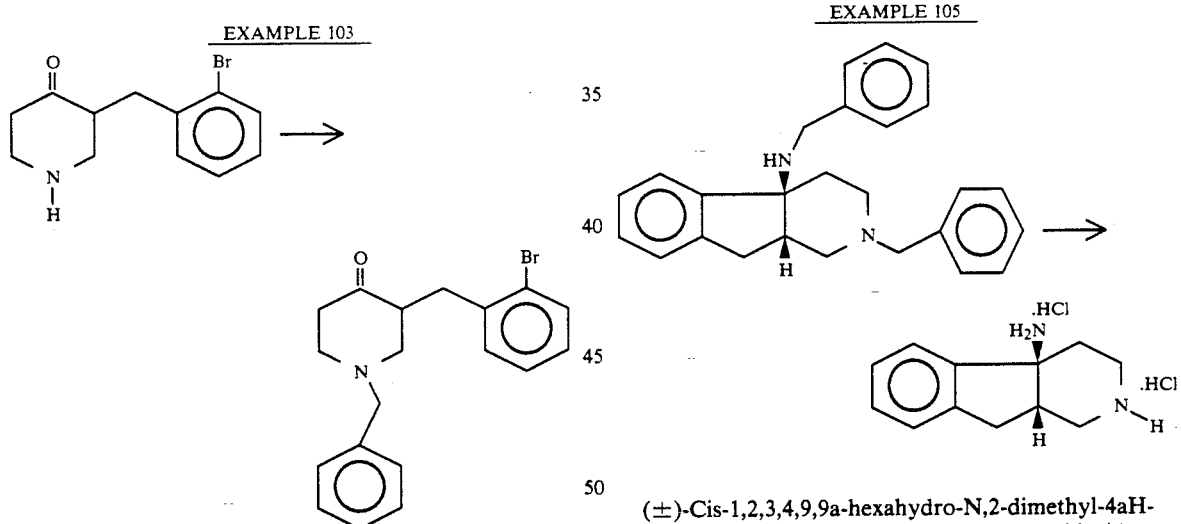

3-[(2-Bromophenyl)methyl]-1-(phenylmethyl)-4-piperidinone

The amine (7.0 g, 23 mmol) from Example 102 and sodium carbonate (4.88 g, 46 mmol) were slurried in ethanol (50 ml). Benzyl bromide was added and the reaction was stirred for 18 hours at 25° C. The reaction was filtered and concentrated. The residue was partitioned between water and dichloromethane. The dichloromethane layer was dried (MgSO$_4$), filtered, and concentrated to yield a crude yellow residue which was chromatographed on a silica gel column eluted initially with dichloromethane followed by methanol/dichloromethane (1:99). The title compound was eluted as a pale yellow oil (7.2 g, 88%).

EXAMPLE 104

(±)-Cis-1,2,3,4,9,9a-hexahydro-N,2-bis(phenylmethyl)-4aH-indeno[2,1-c]-pyridin-4a-amine In a manner similar to that described in Example 83, the ketone (6.21 g, 17 mmol) from Example 103 in toluene (50 ml) was treated with benzyl amine (2.5 g, 23 mmol) and tosic acid (50 mg) to produce the imine (6.93 g). To a solution of the imine in tetrahydrofuran (100 ml) was added tBuLi (1.7M) (10 ml, 17 mmol) to produce the title compound as a yellow oil (1.2 g, 23%) after silica gel chromatography.

EXAMPLE 105

(±)-Cis-1,2,3,4,9,9a-hexahydro-N,2-dimethyl-4aH-indeno[2,1-c]pyridin-4a-amine dihydrochloride In a manner similar to that described in present Example 84, the benzylamine product of Example 104 (0.8 g, 2.0 mmol) is reduced to give the title compound.

EXAMPLE 106

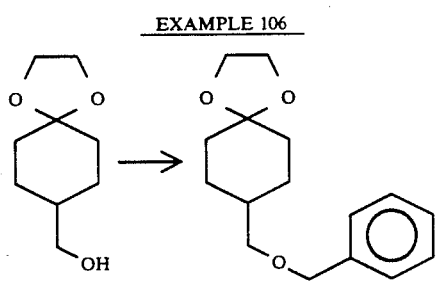

8-[(Phenylmethoxy)methyl]-1,4-dioxospiro[4.5]decane

To a solution of sodium hydride (2.5 g, 105 mmole) in dry tetrahydrofuran (150 ml) was added via an addition funnel a solution of the 1,4-dioxaspiro[4.5]decan-7-methanol (Berkowitz, W. F., et al, *J. Org. Chem.*, 1987, 52, 1119), (15 g, 87.1 mmol) and dry tetrahydrofuran (25 ml). After stirring 30 minutes, benzylbromide (11.4 ml, 95.8 mmol) was added. The mixture was stirred for 4 days at room temperature. The reaction mixture was poured onto water and the organics layered with ether. The ether layer was dried (MgSO4), concentrated in vacuo, and chromatographed to give 19.4 g (85% yield) of the title compound as a colorless oil.

EXAMPLE 107

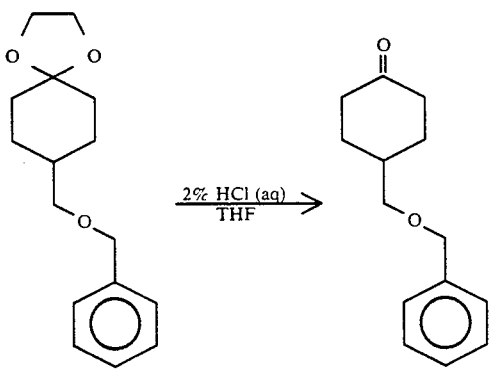

4-[(phenylmethoxy)methyl]cyclohexanone

A solution of the compound of Example 106 (18.43 g, 70.2 mmol) in tetrahydrofuran (400 ml) was added 50 ml of a 2% aqueous HCl solution and stirred for 24 hours. The mixture was concentrated in vacuo and the residual solution layered with ether. The ether layer was dried (MgSO4), concentrated in vacuo, then chromatographed to give 11.16 g (73% yield) of the title compound as a colorless oil.

EXAMPLE 108

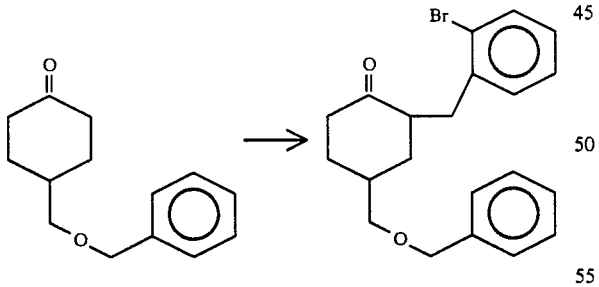

2-[(2-bromophenyl)methyl]-4-[(phenylmethoxy)methyl]-cyclohexanone

To a 0° C. of N,N-diisopropylamine (6.1 ml, 43.4 mmole) in dry tetrahydrofuran (50 ml) was added n-butyllithium (1.6M in hexane), (27 ml, 43.4 mmol). This solution was added slowly to a cold (−78° C.) solution of the product of Example 107. After stirring 30 minutes a solution of 2-bromobenzyl bromide (8.3 g, 33.4 mmol) was added. The mixture stirred for 6 hours at 0° C. and was poured onto water. The organics were layered with ether (500 ml). The ether layer was dried (MgSO4), concentrated in vacuo, then chromatographed to give 2.94 g (23% yield) of the title compound as a light yellow oil.

EXAMPLE 109

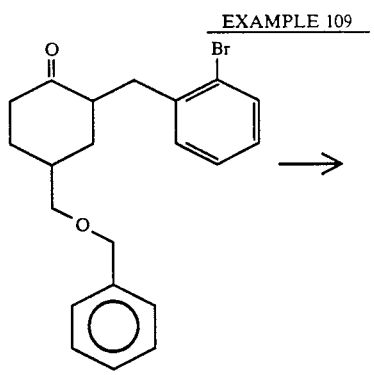

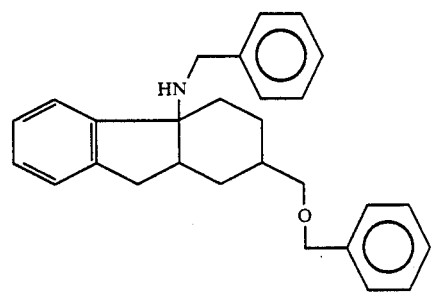

(±)-cis-1,2,3,4,9,,9a-hexahydro-2-[(phenylmethoxy)-methyl]-N-(phenylmethyl)-4aH-flouren-4a-amine The ketone (1.73 g, 4.5 mmol) from Example 108 was converted to the cyclized product in a manner similar to the procedure as described in Example 93. The product was chromatographed to give 0.37 g (21% yield) of the title compound as a thick colorless oil.

EXAMPLE 110

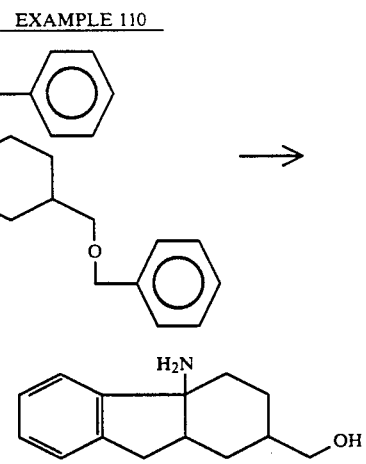

(±)-Cis-4a-amino-2,3,4,4a,9,9a-hexahydro-1H-flourene-2-methanol monohydrochloride The compound of Example 109 (0.71 g, 1.8 mmol) was subjected to the hydrogenation conditions in a manner similar to that described in Example 84. The product obtained was chromatographed to give 0.32 g (58% yield) of the N-debenzylated material. The benzyl ether (0.32 g, 1.04 mmol) in dichloromethane (5 ml) was added trimethylsilyliodide (0.74 ml, 5.2 mmol). The mixture stirred at room temperature for 24 hours. An additional 200 ml of dichoromethane was added and the organics washed with water. The dichloromethane layer was dried (MgSO₄) then concentrated in vacuo. The colorless oil was converted to the hydrochloride salt with isopropanolic HCl to give 180 mg (68% yield) of the title compound as a white solid mp 259° C.

EXAMPLE 111

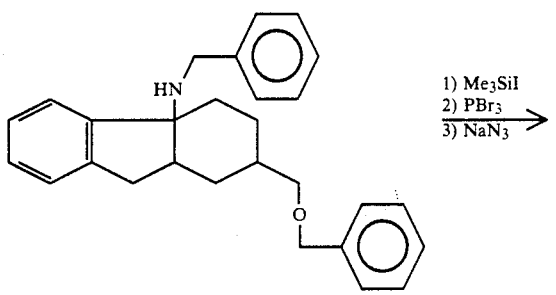

(±)-cis-2-(azidomethyl)-1,2,3,4,9,9a-hexahydro-N-(phenylmethyl)-4aH-flouren-4a-amine A solution of the compound of Example 109 in dichloromethane is treated with trimethylsilyl iodide. The solution is stirred at room temperature for 24 hours. The reaction is diluted with dichloromethane and washed with water. The dichloromethane layer is dried (MgSO₄), concentrated in vacuo, then chromatographed. The alcohol is taken up in ether and treated with phosphorus tribromide. After stirring for 8 hours the reaction is diluted with ether. The ether layer is washed with water. The ether layer is dried (MgSO₄), concentrated in vacuo. The product is taken up in tetrahydrofuran. Sodium azide (5 equivalents) is added and the mixture refluxed for hours. After cooling the salts are removed by suction filtration. The resulting solution is concentrated in vacuo and chromatographed to give the title compound.

EXAMPLE 112

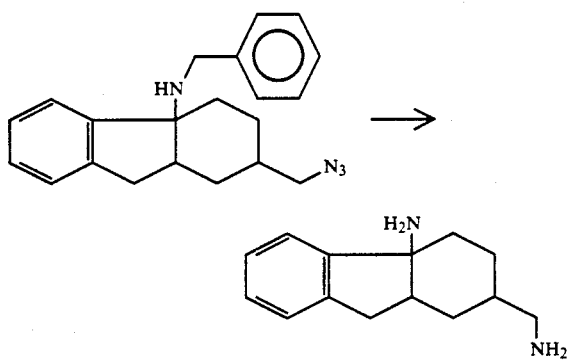

(±)-Cis-4a-amino-2,3,4,4a,9,9a-hexahydro-1H-flourene-2-methanamine dihydrochloride The compound of Example 111 is hydrogenated in a manner similar to that described in Example 84. The diamine is chromatographed. The product is taken up in ethanol and treated with isopropanolic HCl to give the title compound.

EXAMPLE 113

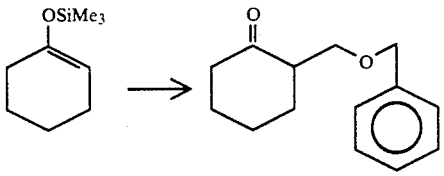

2-[(phenylmethoxy)methyl]cyclohexanone

A solution of 1-cyclohexenyloxytimethylsilane in dry tetrahydrofuran is treated with n-butyllithium (1.6M in hexane), (1.1 equivalents). After stirring 45 minutes the solution is cooled to 0° C. and a solution of zinc chloride (0.5 equivalents) in tetrahydrofuran is added dropwise. The mixture is stirred for 30 minutes followed by addition of choromethylbenzyl ether (1.2 equivalents) as a solution in tetrahydrofuran. After stirring for 6 hours, water is added. The organics are layered with ether, dried (MgSO₄), concentrated in vacuo, then chromatographed to give the title compound.

EXAMPLE 114

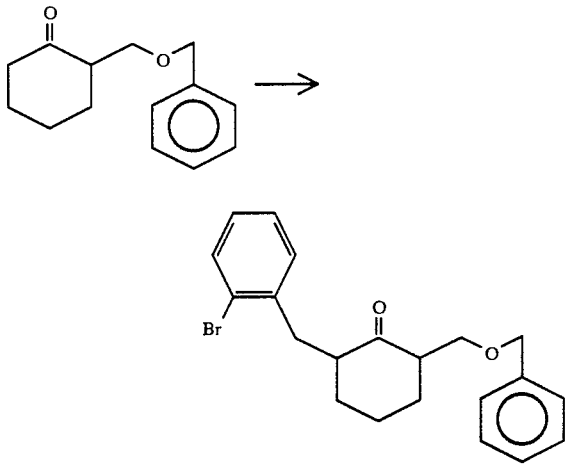

2-[(2-Bromophenyl)methyl]-6-[(phenylmethoxy)methyl]-cyclohexanone

To a solution of the ketone of Example 113 in benzene is added pyrrolidine (4 equivalents). The mixture is heated to reflux for 24 hours removing the water formed by use of a Dean-Stark type aparatus. The reaction mixture is concentrated in vacuo. The organics are dissolved in dioxane followed by addition of 2-bromobenzyl bromide (1.5 equivalents). The mixture is heated to reflux for 6 hours. Water is added and the refluxing continued for 3 hours. The solution is concentrated in vacuo to dryness. The remaining organics are partitioned between ether and water. The ether layer is dried (MgSO4), concentrated in vacuo, then chromatographed to give the title compound.

EXAMPLE 115

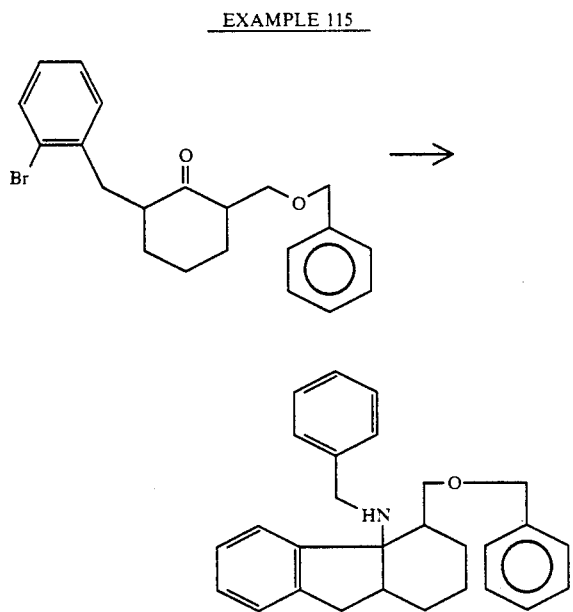

(±)-Cis-1,2,3,4,9,9a-hexahydro-4-[(phenylmethoxy)-methyl]-4aH-flourene-4a-amine

The compound of Example 114 is cyclized in a manner similar to that described for Example 109. The product is chromatographed to give the title compound.

EXAMPLE 116

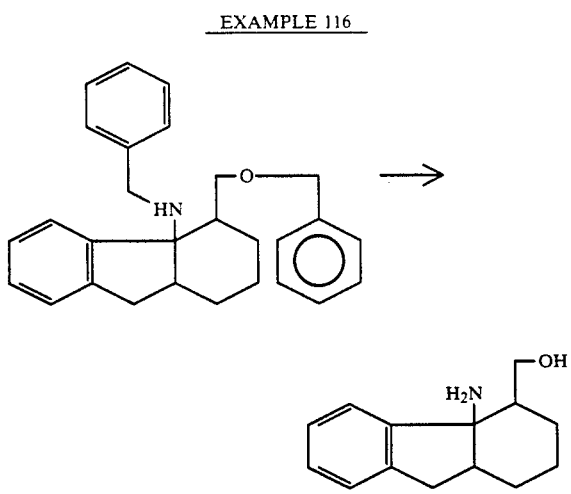

(±)-Cis-4a-amino-2,3,4,4a,9,9a-hexahydro-1H-fluorene-4-methanol monohydrochloride The compound of Example 115 is hydrogenated in a manner similar to that described for Example 84. The product is chromatographed. The product is dissolved in ether and treated with isopropanolic HCl to give the title compound.

EXAMPLE 117

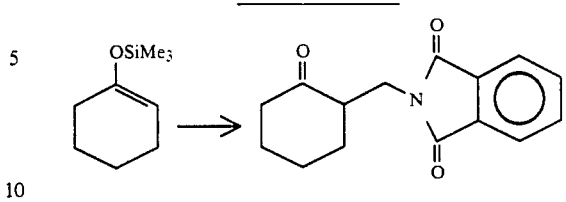

2-[(2-Oxocyclohexyl)methyl]-1H-isoindole-1,3(2H)-one

To a solution of 1-cyclohexenyloxytrimethylsilane in dry tetrahydrofuran is added n-butyllithium (1.6M in hexane), (1.1 equivalents). After stirring at room temperature for 45 minutes the reaction is cooled to 0° C. and a solution of zinc chloride (0.5 equivalents) in tetrahydrofuran is added dropwise. The reaction mixture is stirred for 30 minutes followed by addition of a solution of N-(bromomethyl)phthalimide in tetrahydrofuran. The mixture is warmed to room temperature and stirred for 24 hours. The reaction is partitioned between water and ethyl acetate. The ethyl acetate layer is dried (MgSO4), concentrated in vacuo, then chromatographed to give the title compound.

EXAMPLE 118

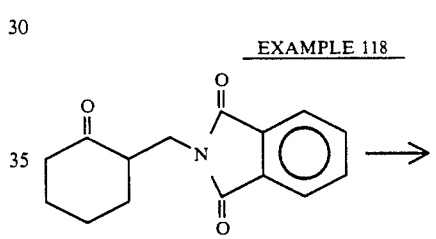

2-[[3-[(2-Bromophenyl)methyl]-2-oxocyclohexyl]methyl]-1H-isoindole-1,3(2H)-dione To the compound of Example 117 in benzene is added pyrrolidine (4 equivalents). The mixture is heated to reflux for 48 hours removing the water formed using a Dean-Stark apparatus. The reaction mixture is concentrated in vacuo. The organics are dissolved in dioxane and 2-bromobenzyl bromide (1.5 equivalents) is added. The mixture is heated to reflux for 18 hours. Water is added and the refluxing is continued for an additional 3 hours. The solution is concentrated in vacuo and the remaining organics partitioned between ethyl acetate and water. The ethyl acetate layer is dried (MgSO4), concentrated in vacuo, then chromatographed to give the title compound.

EXAMPLE 119

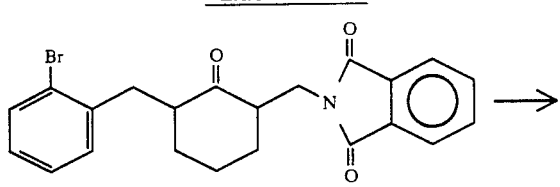

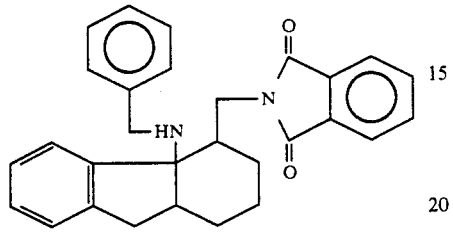

2-[2,3,4,4a,9,9a-hexahydro-4a-[(phenylmethyl)amino]-1H-flouren-4-yl]-1H-isoindole-1,3(2H)-dione The compound of Example 118 is cyclized in a manner similar to the method described in Example 93. The product is chromatographed to give the title compound.

EXAMPLE 120

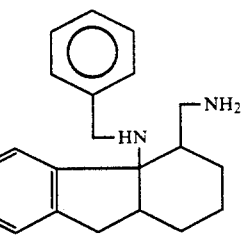

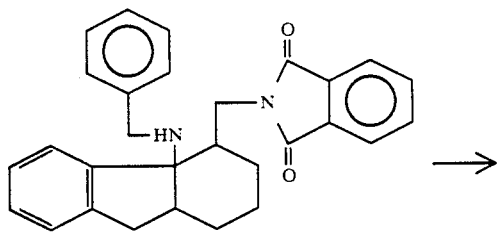

(±)-cis-2,3,4,4a,9,9a-hexahydro-4a-[(phenylmethyl)-amino]-1H-flourene-4-methanamine The compound of Example 119 is dissolved in toluene. To this solution is added hydrazine monohydrate (1.2 equivalents). The mixture is refluxed for 8 hours. The solution is filtered to remove the precipitate. The toluene layer is concentrated in vacuo and the resulting organics chromatographed to give the title compound.

EXAMPLE 121

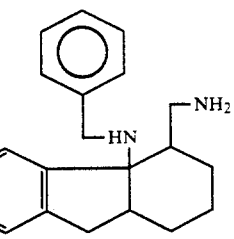

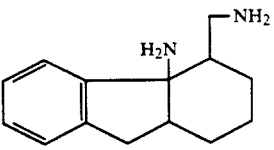

(±)-cis-4a-amino-1,2,3,4a,9,9a-hexahydro-4H-flourene-4-methanamine dihydrochloride The compound of Example 120 is hydrogenated in a manner similar to the method described in Example 84. The product is chromatographed then dissolved in ethanol. The solution is treated with isopropanolic HCl to give the title compound.

EXAMPLE 123

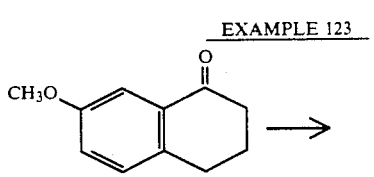

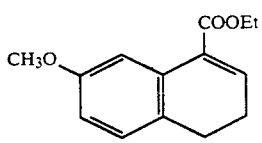

Ethyl 1,2,3,4-dihydro-7-methoxy-1-napthalenecarboxylate

In a manner similar to that described in Example 15, 7-methoxy-1-tetralone (80.7 g) was reacted to give the title compound as an oil (45 g, 45%).

EXAMPLE 124A

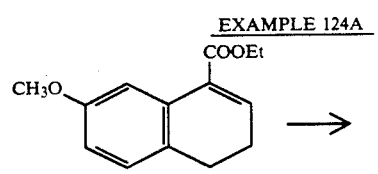

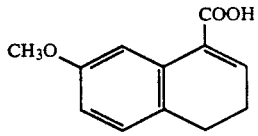

3,4-Dihydro-7-methoxy-1-napthlenecarboxylic acid

A solution of the product from Example 123 (45 g) in 500 ml of aqueous 1N NaOH solution was heated at reflux for 18 hours. The reaction mixture was cooled to room temperature and diluted with H₂O (500 ml). The aqueous phase was extracted with CH₂Cl₂ (5×25 ml) and acidified with aqueous HCl solution. The solution was cooled in an ice bath and the solid which precipitated was collected and dried in vacuo at 60° C. to give the title compound as a solid (39.5 g, 99%), mp 115° C.

EXAMPLE 124B

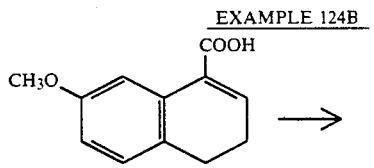

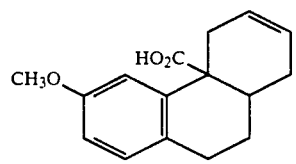

(±)-Cis-1,9,10,10a-tetrahydro-6-methoxy-1-napthylenecarboxylic acid

In a manner similar to that described in Example 16, the product of Example 123 (35.9 g) was reacted with butadiene to give the title compound as a white solid (22 g, 44%), mp 125° C.

EXAMPLE 125

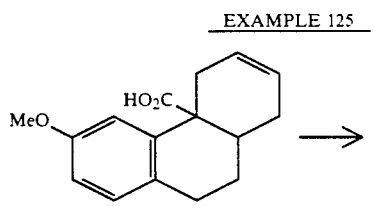

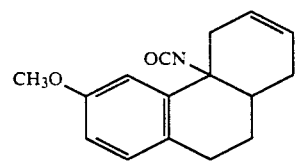

(±)-cis-1,4,4a,9,10,10a-hexahydro-4a-isocyanato-6-methoxy-phenanthrene

To a solution of the product from Example 124B (5.0 g) in dry benzene (150 ml) was added diphenylphosphoryl azide (5.2 g) and triethylamine (2.3 g). The solution was refluxed under a nitrogen atmosphere for 24 hours, cooled and washed with water and dried (Na₂SO₄). Evaporation of the solvent afforded a oil which was purified by chromatography on silica gel (9:1 heptane/EtOAc) to afford the title compound as a yellow oil (3.2 g, 65%)

EXAMPLE 126

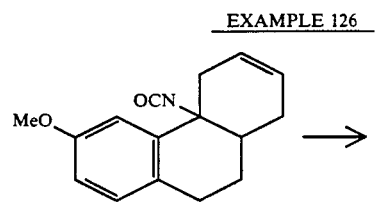

-continued
EXAMPLE 126

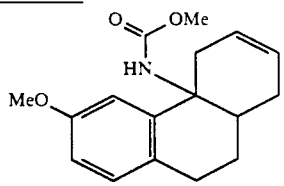

Methyl (±)-cis-(1,9,10,10a-tetrahydro-6-methoxy-4a(4H)-phenanthrenyl)carbamate

In a manner similar to that described in Example 23, the product of Example 125 (1.5 g) was converted to the title compound as a white solid (1.75 g, quantative) mp 120°–122° C.

EXAMPLE 127

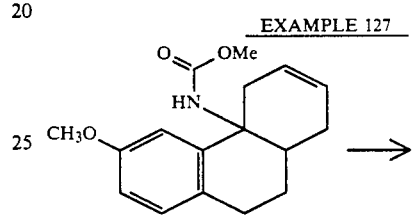

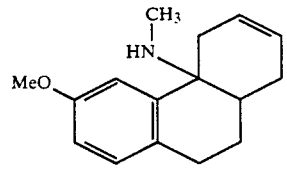

(±)-Cis-1,9,10,10a-tetrahydro-6-methoxy-N-methyl-4a(4H)-phenanthreneamine

In a manner similar to Example 4, the product of Example 126 (1.7 g) was converted to give the title compound as a white solid (1.4 g, 85%) mp 252° C.

EXAMPLE 128

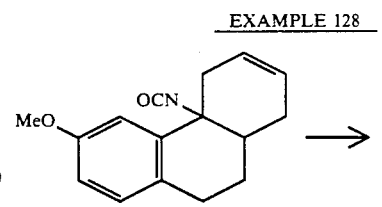

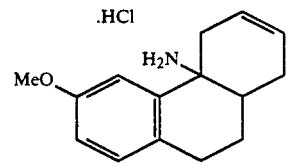

(±)-Cis-1,9,10,10a-tetrahydro-6-methoxy-4a(4H)-phenanthreneamine monohydrochloride To a solution of the product from Example 125 (1.5 g) in benzene (10 ml) was added 50% aqueous KOH solution and a trace of 18-crown-6. The solution was stirred at room temperature for 96 hours. The reaction was treated with aqueous 3N HCl solution (300 ml) and extracted into ether (2×50 ml), dried and concentrated.

The residue was converted to give the title compound as a white solid (0.83 g, 53%) mp 270° C.

EXAMPLE 129

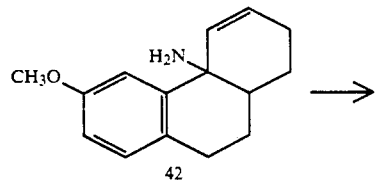

(±)-Cis-4b,5,8,8a,9,10-hexahydro-4b-amino-3-phenanthrenol.

To a solution of the product from Example 128 (0.20 g) in CH$_2$Cl$_2$ (10 ml) was added BBr$_3$ (2 ml of a 1.0M solution in CH$_2$Cl$_2$. The reaction was stirred at room temperature for 18 hours and quenched by the addition of water. Additional CH$_2$Cl$_2$ (10 ml) and 1N HCl (20 ml) was added. The aqueous phase was separated, and made basic (pH=10) by the addition of NaHCO$_3$. The aqueous phase was extracted with EtOAc (5×10 ml). The combined organic phases were dried over MgSO$_4$, filtered and concentrated. The residue was dissolved in 0.5N HCl and freeze dried to give the title compound as a white solid (90 mg, 41%), mp 156°-161° C.

EXAMPLE 130

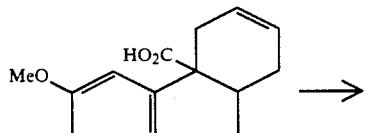

(±)-Cis-1,3,4,9,10,10a-tetrahydro-6-methoxy-4a(2H)-phenanthrenecarboxylic acid

In a manner similar to that described in Example 20 the product of Example 124A (3.03 g) was converted to the title compound as a white solid (2.5 g, 83%), mp 171°-173° C.

EXAMPLE 131

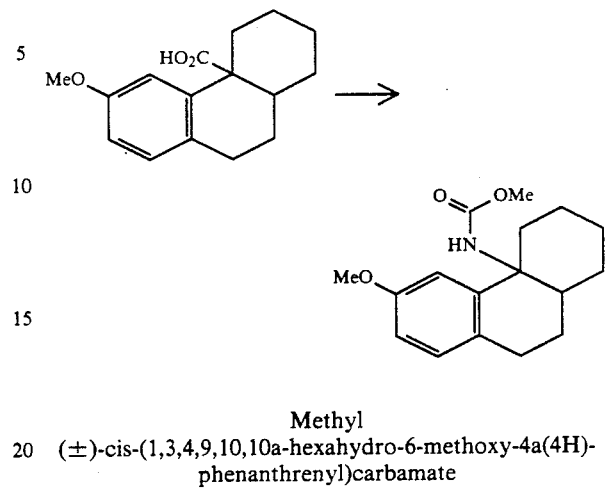

Methyl (±)-cis-(1,3,4,9,10,10a-hexahydro-6-methoxy-4a(4H)-phenanthrenyl)carbamate In a manner similar to that described in Example 23 the product of Example 130 (2.9 g) was converted to give the title compound as a white solid (1.76 g, 53%), mp 96°-99° C.

EXAMPLE 132

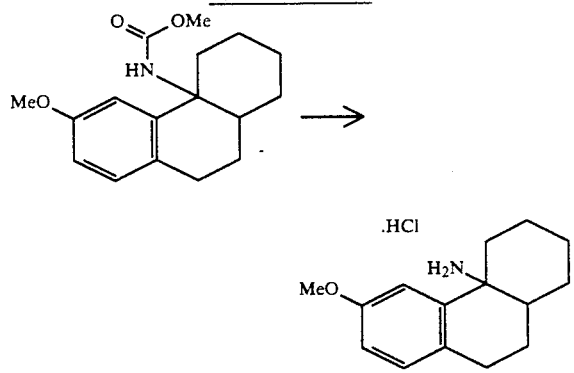

(±)-Cis-1,3,4,9,10,10a-hexahydro-6-methoxy-4a(2H)-phenanthreneamine

To a solution of the product from Example 131 (1.76 g) in dry THF (40 ml) was added potassium trimethylsilanolate (2.0 g). The resulting solution was heated at reflux for 7 hours. The reaction mixture was cooled to room temperature and poured into 1N HCl solution. The resulting solution was extracted with ether. The aqueous phase was separated and basified with solid NaOH. The basic solution was extracted with ether (3×25 ml) and the combined organic extracts were dried (MgSO$_4$), filtered and treated with isopropanolic HCl. The white solid obtained was dried in vacuo to give the title compound (0.30 g, 18%), mp 256°-263° C.

EXAMPLE 133

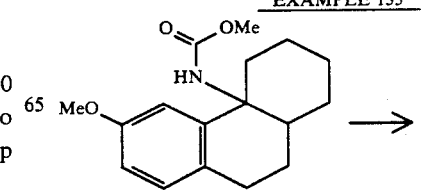

EXAMPLE 133

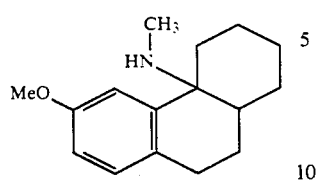

(±)-Cis-1,3,4,9,10,10a-hexahydro-6-methoxy-N-methyl-4a(2H)-phenanthreneamine

In a manner similar to that described in Example 4 the product of Example 131 (1.66 g) was reduced to the title compound as a white solid (1.3 g, mp 263°–265° C.

EXAMPLE 134

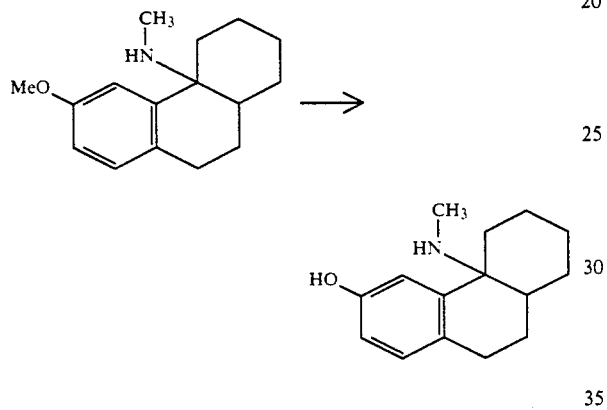

(±)-Cis-4b,5,6,7,8,8a,9,10-octahydro-4b-(methylamino)-2-phenanthreneol

A solution of the product from Example 133 (150 mg) in 48% aqueous HBr was heated at reflux for 2.5 hours. The reaction mixture was poured into cold aqueous NH₄OH solution. The resulting solution was extracted with ethyl acetate (3×25 ml), dried (MgSO₄) and filtered. Evaporation of the solvent and drying in vacuo afforded the title compound as a tan solid (90 mg, 74%), mp 191° C.

EXAMPLE 135

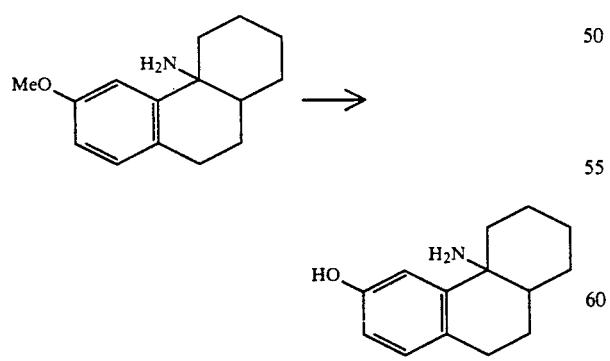

(±)-Cis-4b,5,6,7,8,8a,9,10-octahydro-4b-amino-3-phenanthrenol

In a manner similar to that described in example the product of Example 132 (0.28 g) was converted to the title compound as a white solid (88 mg, 33%), mp 198°–200° C. (dec.).

EXAMPLE 136

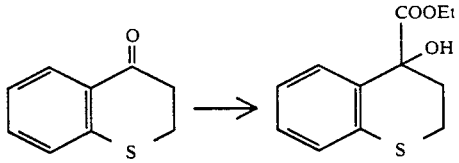

Ethyl 3,4-dihydro-4-hydroxy-2H-1-benzothiopyran-4-carboxylate

In a manner similar to that described in Example 123, thiochromanone (34.4 g) was converted to the title compound as a solid (17.5 g, 34%), mp 117°–119° C.

EXAMPLE 137

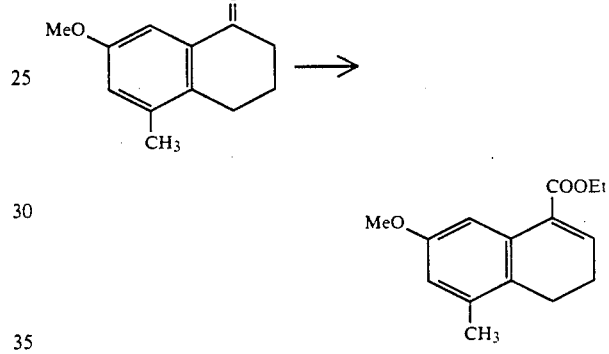

Ethyl 3,4-dihydro-7-methoxy-5-methyl-1-napthlenecarboxylate

In a manner similar to that described in Example 123, 3,4-dihydro-7-methoxy-5-methyl-1(2H)-naphthalenone(4) (*J. Org. Chem.*, 1962, 27, 2015) (43.5 g) was converted to the title compound as a yellow oil (17.0 g, 30%).

EXAMPLE 138

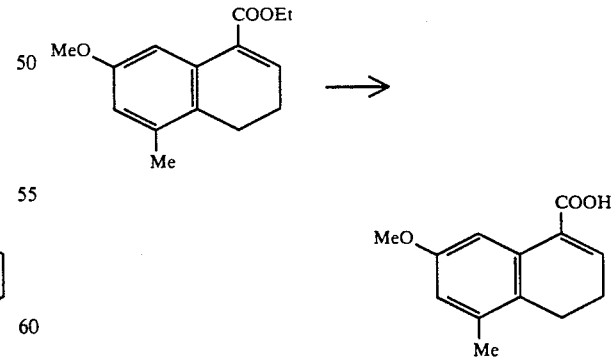

3,4-Dihydro-7-methoxy-5-methyl-1-napthalenecarboxylic acid

In a manner similar to that described in Example 19, the product of Example 137 (17.0 g,) was converted to the title compound which was recrystallized from diisopropyl ether/THF to give the title compound as a white solid (10.2 g, 68%), mp 149°–150° C.

EXAMPLE 139

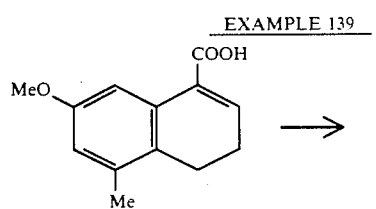

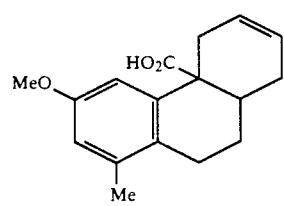

(±)-Cis-1,9,10,10a-tetrahydro-6-methoxy-8-methyl-4a(4H)-phenanthrenecarboxylic acid In a manner similar to that described in Example 16 the product of Example 138 (10.2 g) was converted to the title compound as an oil (3.5 g, 28%).

EXAMPLE 140

EXAMPLE 141

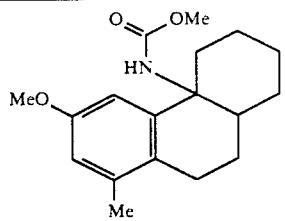

Methyl (±)-cis-(1,9,10,10a-tetrahydro-6-methoxy-4a(4H)-phenanthrenyl)carbamate

In a manner similar to that described in Example 23, the product of Example 139 (0.55 g) was converted to the title compound as a white solid (440 mg, 73%).

EXAMPLE 141

Methyl (±)-cis-(1,3,4,9,10,10a-hexahydro-6-methoxy-8-methyl-4a(2H)-phenathrenyl)carbamate In a manner similar to that described in Example 20 the product from Example 140 is hydrogenated to give the title compound.

EXAMPLE 142

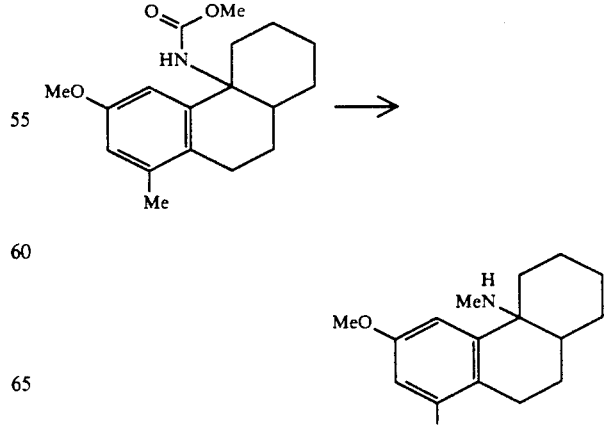

(±)-Cis-1,9,10,10a-tetrahydro-6-methoxy-N,8-dimethyl-4a(4H)-phenanthrenamine

In a manner similar to that described in Example 4, the product of Example 140 (0.38 g) was reduced to give the title compound as a yellow oil (0.30 g, 92%).

EXAMPLE 143

(±)-cis-1,3,4,9,10,10a-hexahydro-6-methoxy-N,8-dimethyl-4a(2H)-phenanthreneamine In a manner similar to that described in Example 4 the product of Example 141 is reduced to give the title compound.

EXAMPLE 144

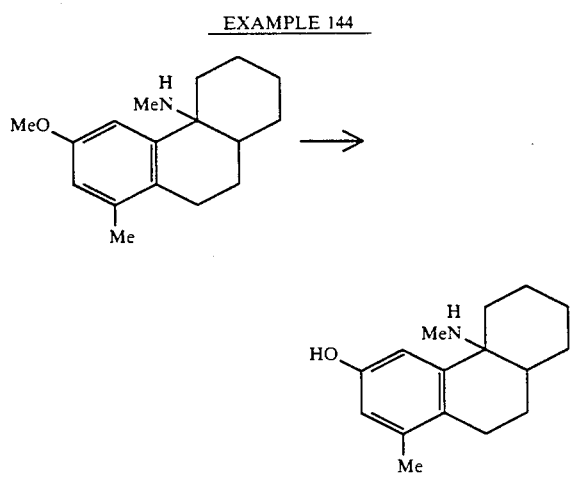

(±)-Cis-4b,5,6,7,8,8a,9,10-octahydro-1-methyl-4b-(methylamino)-3-phenanthrenol

In a manner similar to that described in Example 134, the product of Example 143 is converted to the title compound.

EXAMPLE 145

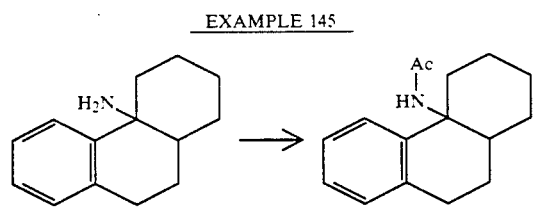

(±)-Cis-(1,3,4,9,10,10a-hexahydro-4a(2H)-phenanthrenyl)acetamide

To a solution of the compound from Example 2 (0.23 g) in CH$_2$Cl$_2$ (10 ml) was treated with acetyl chloride (0.91 g). The reaction mixture was heated at reflux for 15 minutes. Water (5 ml) was added and heating continued for an additional 15 min. The reaction mixture was cooled to room temperature and the organic layer was separated. The aqueous layer was extracted with CH$_2$Cl$_2$ (3×10 ml) and the combined organic phases were dried (MgSO$_4$), filtered and concentrated to give the title compound as a white solid (0.26 g, 97%), mp 177° C.

EXAMPLE 146

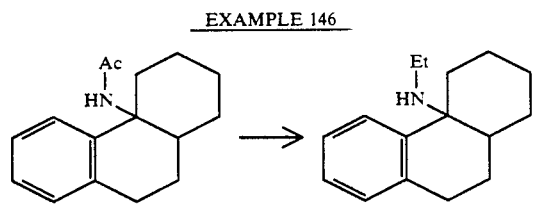

(±)-Cis-1,3,4,9,10,10a-hexahydro-N-ethyl-4a(2H)-phenanthrenamine

In a manner similar to that described in Example 22, the compound from Example 145 (0.26 g) was converted to the title compound as a white solid (0.24 g, 95%), mp 235°–237° C.

EXAMPLE 147

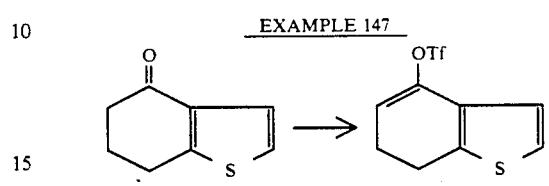

6,7-Dihydrobenzo[b]thien-4-yl triflouromethanesulfonate

To a solution of 4-keto-4,5,6,7-tetrahydrothianapthene (33.7 g) in CH$_2$Cl$_2$ (800 ml) at 0° C. was added tryflic anhydride (70 g). The resulting solution was allowed to stir at 0° C. for 30 min and was warmed to room temperature. The resulting brown solution was concentrated and the residue was taken up in 1:1 heptane/ethyl acetate (1l) and the resulting suspension filtered. The filtrate was concentrated and the residue was filtered thru a plug of silica gel (9:1 heptane/ethyl acetate). The eluent was concentrated to give the title compound as a oil (55.8 g, 89%).

EXAMPLE 148

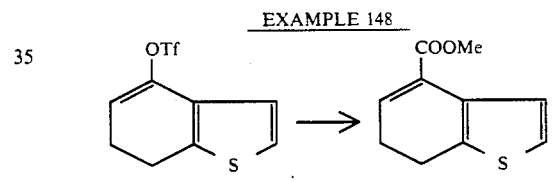

Methyl 6,7-dihydrobenzo[b]thiophene-4-carboxylate

A solution of the compound from Example 147 (55.5 g), palladium acetate (1.3 g), and triphenylphosphine (3.3 g) in DMF (1000 ml), methanol (360 ml), and triethylamine (57 ml) was vigorously stirred under a carbon monoxide atmosphere for 3 hours. The reaction mixture was concentrated and the residue was taken up in ether (500 ml) and washed with water (50 ml). The organic phase was dried (MgSO$_4$), filtered and concentrated. Chromatography of the residue (silica gel, 9:1 heptane/ethyl acetate) afforded the title compound as a colorless oil (17.9g, 47%).

EXAMPLE 149

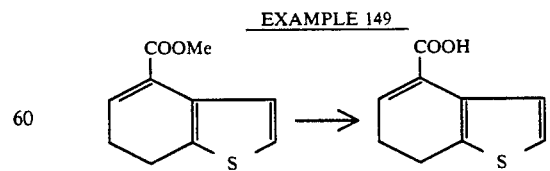

6,7-Dihydrobenzo[b]thiophene-4-carboxylic acid

In a manner similar to that described in Example 19, the product from Example 148 (22.5 g) was converted to the title compound as a solid (10.4 g, 50%).

EXAMPLE 150

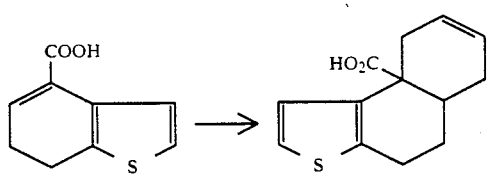

(±)-Cis-4,5,5a,6-tetrahydronaptho2,1-b]thiophene-9a(9H)-carboxylic acid

In a manner similar to that described in Example 16, the product from Example 149 (10.0 g) was converted to the title compound as a white solid (2.26 g, 17%).

EXAMPLE 151

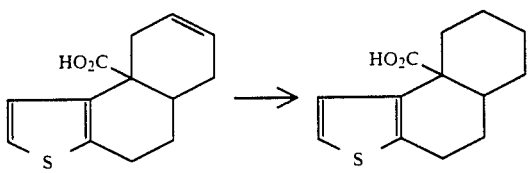

(±)-cis-5,5a,6,7,8,9-hexahydronaptho2,1-b]thiophene-9a(4H)-carboxylic acid

In a manner similar to that described in Example 20, the product of Example 150 (1.89 g) was converted to the title compound (0.98 g, 51%).

EXAMPLE 152

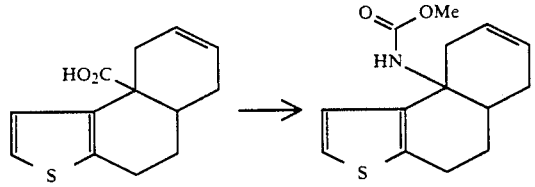

Methyl (±)-cis-4,5,5a,6-tetrahydronaptho[2,1-b]-thien-9a(9H)-yl carbamate

In a manner similar to that described in Example 20 the product of Example 150 (0.37 g) was converted to the title compound as a white solid (0.18 g, 43%).

EXAMPLE 153

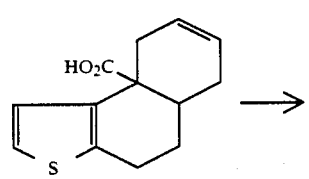

-continued
EXAMPLE 153

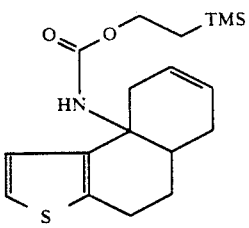

2-(Trimethylsilyl)ethyl (±)-cis-4,5,5a,6-tetrahydronaptho[2,1-b]thien-9a(9H)-ylcarbamate In a manner similar to that described in Example 21 the product of Example 150 (0.47 g) was converted to the title compound as a waxy solid (0.45 g, 67%).

EXAMPLE 154

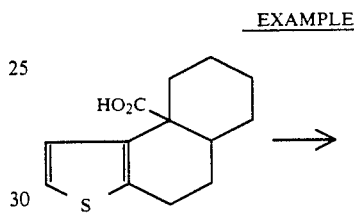

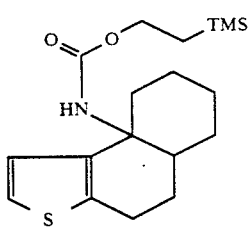

2-(Trimethylsilyl)ethyl (±)-cis-5,5a,6,7,8,9-hexahydronaptho[2,1-b]thiophene-9a(4H)-ylcarbamate In a manner similar to that described in Example 21, the product of Example 151 (0.72 g) was converted to the title compound as an oil (0.33 g, 31%).

EXAMPLE 155

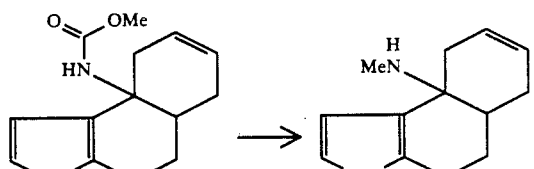

(±)-cis-4,5,5a,6-tetrahydro-N-methylnaptho[2,1-b]-thiophen-9a(9H)-amine

In a manner similar to that described in Example 23 the product of Example 152 (0.15 g) was reduced to give the title compound as a white solid (60 mg, 41%), mp 189°–190° C.

EXAMPLE 156

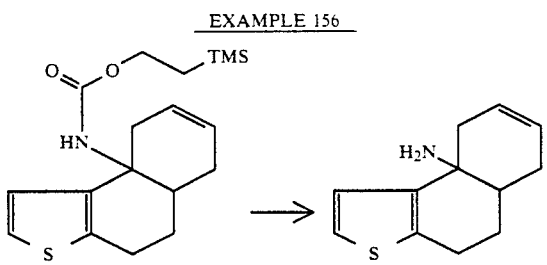

(±)-Cis-4,5,5a,6-tetrahydronaptho[2,1-b]thiophen-9a(9H)-amine

In a manner similar to that described in Example 25 the product of Example 153 (0.42 g) was converted to give the title compound as a white solid (0.16 g, 53%), mp 214°-216° C.

EXAMPLE 157

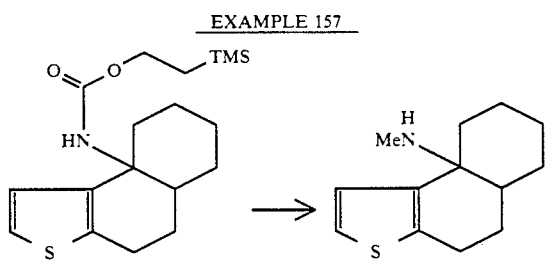

(±)-Cis-5,5a,6,7,8,9-hexahydro-N-methylnaptho[2,1b]-thiophene-ga(4H)-amine

In a manner similar to that described in Example 24, the product of Example 154 (0.33 g) was reduced to give the title compound as a white solid (0.11 g, 46%), mp 185°-187° C.

EXAMPLE 158

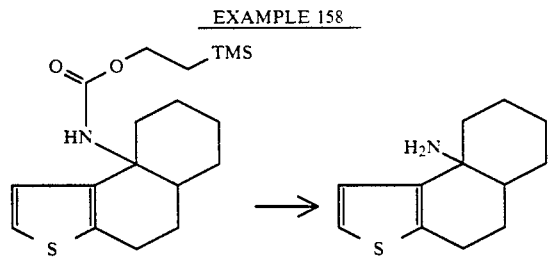

(±)-Cis-5,5a,6,7,8,9-hexahydronaptho2,1-b]thiophene-9a(4H)-amine

In a manner similar to that described in Example 25, the product of Example 154 (0.33 g) was converted to the title compound as a white solid (0.10 g, 45%), mp 189°-192° C.

EXAMPLE 163

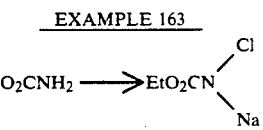

Ethyl chlorocarbamate sodium salt

To an ice cold solution of urethane (8.9 g, 0.1 mole) in methanol (100 ml) is added a solution of t-butyl hypochlorite (10.9 g, 0.1 mole). After 15 minutes, a solution of sodium methoxide (5.4 g, 0.1 mole) in methanol (100 ml) is added dropwise. The solution is evaporated in vacuo and the title compound is isolated as the residual white solid which is washed with dry ether and dried at room temperature.

EXAMPLE 164

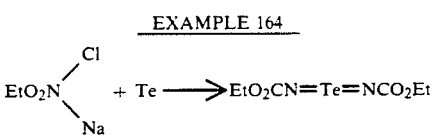

N,N'-bis(ethoxycarbonyl)tellurium diimide

To a suspension of tellurium powder (6.38 g, 50 mmol) in dry acetonitrile (100 ml) under a nitrogen atmosphere, is added in portions, ethyl N-chloro-N-sodiocarbamate (14.55 g, 0.1 mole). After vigorous stirring for 1 hour, the suspension/solution of the title compound is used without further isolation.

EXAMPLE 165

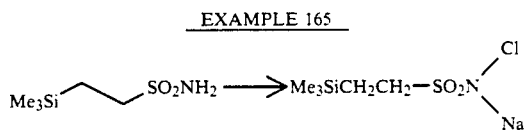

N-chloro-2-(trimethylsilyl)ethanesulfonamide sodium salt

In a manner similar to that described in Example 163, 2-trimethylsilylethylcarbamate (which may be prepared by the method of B. Leov and M. F. Kormendy in *J. Org. Chem.*, 1963, 28, 3421) is reacted with t-butyl hypochlorite and sodium methoxide to give as a white powder the title compound.

EXAMPLE 166

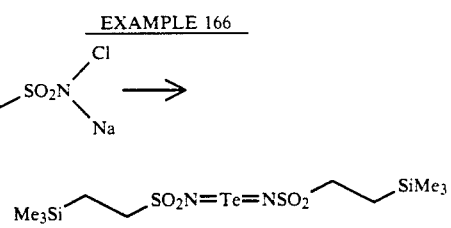

N,N'-bis[[2-(trimethylsilyl)ethyl]-sulfonyl]tellurium diimide

In a manner similar to that described in Example 164, tellurium powder (0.1 mole) is reacted with N-chloro-2-(trimethylsilyl)ethanesulfonamide sodium salt to afford the title compound which was also used without further isolation.

EXAMPLE 167

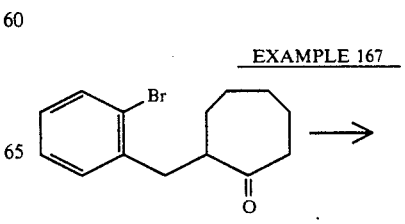

EXAMPLE 167 (continued)

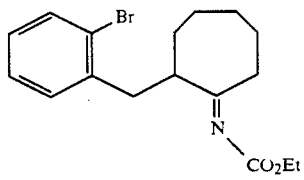

Ethyl [2-[(2-bromophenyl)methyl]cycloheptylidene]-carbamate

To a suspension/solution of N,N-di-ethoxycarbonyl tellurium diimide in acetonitrile (15 g), prepared in Example 166 is added a solution of 2-[(2-bromophenyl)methyl]cycloheptanone (26.7 g, 0.1 mole). The solution is stirred at room temperature for 24 hours, then filtered and the solvent removed under vacuo to give the title imine which is used without further purification.

EXAMPLE 168

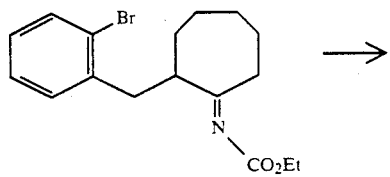

Ethyl [6,7,8,9,9a,10-hexahydrobenz[a]azulen-4b(5H)-yl]carbamate

To a solution of the N-ethoxycarbonylimine (3.38 g, 0.1 mole) from Example 167 in dry tetrahydrofuran (100 ml) cooled to −78° C. is treated with t-butyllithium in a similar manner to that described in Example 83 to afford after workup the title compound.

EXAMPLE 169

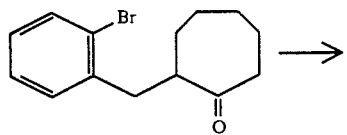

N-[2-[(2-bromophenyl)methyl]cycloheptylidene]-2-(trimethylsilyl)ethanesulfonamide In a manner similar to that described in Example 167, an acetonitrile suspension/solution of N,N-di-(2-trimethylsilylethylsulfonyl) tellurium diimide is treated with a solution of 2-[(2-bromophenyl)methyl]cyclohepta- none. The resulting title compound is also used without additional purification.

EXAMPLE 170

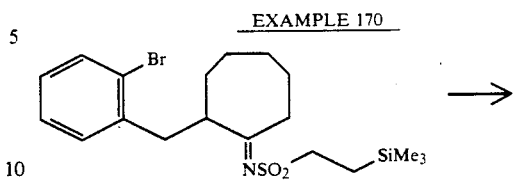

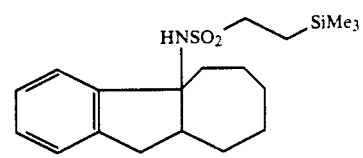

N-(6,7,8,9,9a,10-hexahydrobenz[a]azulen-4b(5H)-yl)-2-(trimethylsilyl)ethanesulfonamide In a manner similar to that described in Example 168, the product from Example 169 is cyclized to give the title compound.

EXAMPLE 171

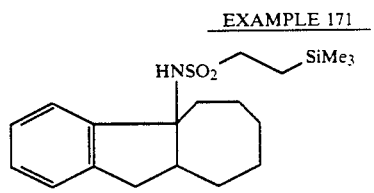

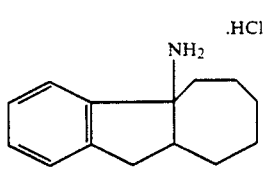

Preparation of (±)-Cis-6,7,8,9,9a,10-hexahydrobenz[a]azulen-4-b(5H)-amine monohydrochloride To a solution of the product from Example 170, in dry tetrahydrofuran is added a solution of tetrabutylammonium fluoride in tetrahydrofuran (1.1 equivalents). The solution is refluxed for 30 minutes and worked up in a manner similar to that described for Example 25 to afford the title compound as a white solid.

I claim:
1. A compound of formula

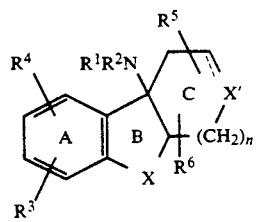

or a pharmaceutically acceptable salt thereof wherein:
$R^1$ and $R^2$ are each independently hydrogen or lower-alkyl;
$R^3$ and $R^4$ are each hydrogen;

$R^5$ and $R^6$ are each independently hydrogen, loweralkyl, loweralkoxy; the—in ring C is an optional double bond, X' is —$CH_2$—, or —CH—;

n is 1; and

X is —$OCHR^7$—, wherein $R^7$ is hydrogen.

2. A compound according to claim 1 wherein the point of fusion of rings B and C is cis or trans.

3. A compound of Formula I

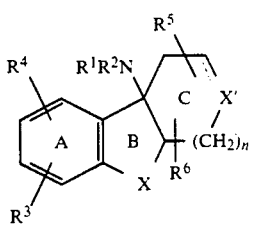

or a pharmaceutically acceptable salt thereof wherein $R^1$ and $R^2$ are each independently hydrogen or methyl;

$R^3$ and $R^4$ are each hydrogen;

$R^5$ and $R^6$ are each independently hydrogen, loweralkyl, or loweralkoxy;

n is 1;

X' is —$CH_2$— or —CH—,

X is —$OCHR^7$—, wherein $R^7$ is hydrogen, the—in ring C is an optional double bond.

4. A compound of Formula I

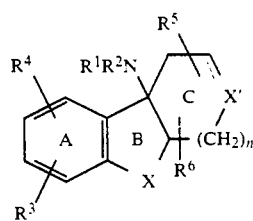

or a pharmaceutically salt thereof wherein $R^1$ and $R^2$ are each independently hydrogen or methyl;

$R^3$ and $R^4$ are each hydrogen;

$R^5$ and $R^6$ are each independently hydrogen, loweralkyl, or loweralkoxy;

X' is —$CH_2$—;

n is 1; and

X is—$OCHR^7$ wherein $R^7$ is hydrogen; and the—in ring C is a single bond.

5. A compound of Formula I

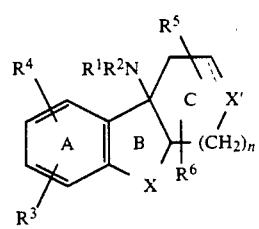

or a pharmaceutically salt thereof wherein $R^1$ and $R^2$ are each independently hydrogen, or methyl;

$R^3$ and $R^4$ are each hydrogen;

$R^5$ and $R^6$ are each hydrogen,

X' is —$CH_2$— n is 1; and X is —$OCHR^7$— wherein $R^7$ is hydrogen; and the in ring C is a single bond.

6. A compound selected from the group consisting of:
6,6a,7,8,9,10-hexahydro-10aH-dibenzo[b,d]-pyran-10a-amine, and
6,6a,7,8,9,10-hexahydro-N-methyl-10aH-dibenzo[b,d]pyran-10a-amine.

7. The compound 6,6a,7,10-tetrahydro-N-methyl-10aH-dibenzo-[b,d]pyran-10a-amine.

8. A pharmaceutical composition for treating cerebrovascular disorders comprising an amount effective for treating cerebrovascular disorders of a compound according to claim 1 together with a pharmaceutically acceptable carrier.

* * * * *